US012802797B2

(12) United States Patent
Mason

(10) Patent No.: US 12,802,797 B2
(45) Date of Patent: Nov. 17, 2026

(54) METHOD AND SYSTEM FOR USING SENSOR DATA TO DETECT JOINT MISALIGNMENT OF A USER USING A TREATMENT DEVICE TO PERFORM A TREATMENT PLAN

(71) Applicant: ROM TECHNOLOGIES, INC., Brookfield, CT (US)

(72) Inventor: Steven Mason, Las Vegas, NV (US)

(73) Assignee: ROM Technologies, Inc., Brookfield, CT (US)

(*) Notice: Subject to any disclaimer, the term of this patent is extended or adjusted under 35 U.S.C. 154(b) by 569 days.

(21) Appl. No.: 17/929,237

(22) Filed: Sep. 1, 2022

(65) Prior Publication Data

US 2023/0058605 A1 Feb. 23, 2023

Related U.S. Application Data

(63) Continuation-in-part of application No. 17/736,891, filed on May 4, 2022, now Pat. No. 12,347,543, (Continued)

(51) Int. Cl.
*G16H 20/30* (2018.01)
*A63B 24/00* (2006.01)
*G16H 50/30* (2018.01)

(52) U.S. Cl.
CPC ......... *G16H 20/30* (2018.01); *A63B 24/0062* (2013.01); *G16H 50/30* (2018.01); *A63B 2024/0065* (2013.01)

(58) Field of Classification Search
CPC ........ G16H 20/30; G16H 50/30; G16H 15/00; G16H 40/63; G16H 40/67; G16H 50/20; (Continued)

(56) References Cited

U.S. PATENT DOCUMENTS 823,712 A 6/1906 Uhlmann
4,499,900 A 2/1985 Petrofsky et al.
(Continued)

FOREIGN PATENT DOCUMENTS

CA 3193419 A1 3/2022
CN 2885238 Y 4/2007
(Continued)

OTHER PUBLICATIONS

Ahmed et al., "Artificial Intelligence With Multi-Functional Machine Learning Platform Development for Better Healthcare and Precision Medicine," Database (Oxford), 2020, pp. 1-35, vol. 2020.
(Continued)

*Primary Examiner* — Eliza A Lam
(74) *Attorney, Agent, or Firm* — Dickinson Wright PLLC; Jonathan H. Harder; Stephen A. Mason

(57) ABSTRACT

A method that includes receiving treatment data associated with a user capable of using a treatment device to perform a treatment plan. The method also includes receiving user related data (URD) associated with the use and receiving alignment data associated with the user while the user engages in at least one activity. The method also includes identifying, based on at least the treatment data, the URD, and the alignment data, at least one alignment characteristic associated with the user and modifying at least one aspect of the treatment plan in response to receiving, from a healthcare professional, treatment plan input including at least one modification to the at least one aspect of the treatment plan.

20 Claims, 12 Drawing Sheets

Related U.S. Application Data which is a continuation-in-part of application No. 17/379,542, filed on Jul. 19, 2021, now Pat. No. 11,328,807, which is a continuation of application No. 17/146,705, filed on Jan. 12, 2021, now Pat. No. 12,191,018, which is a continuation-in-part of application No. 17/021,895, filed on Sep. 15, 2020, now Pat. No. 11,071,597.

(60) Provisional application No. 63/240,636, filed on Sep. 3, 2021, provisional application No. 63/113,484, filed on Nov. 13, 2020, provisional application No. 62/910,232, filed on Oct. 3, 2019.

(58) Field of Classification Search

CPC .... G16H 50/70; G16H 80/00; A63B 24/0062; A63B 2024/0065; A63B 2022/0652; A63B 21/00178; A63B 21/00181; A63B 21/0058; A63B 22/0605; A63B 24/0087; A63B 2022/0623; A63B 2024/0093; A63B 2071/063; A63B 2071/0652; A63B 2071/0655; A63B 2071/0663; A63B 2071/068; A63B 2071/0683; A63B 2220/13; A63B 2220/16; A63B 2220/30; A63B 2220/51; A63B 2220/52; A63B 2225/20; A63B 2225/50; A63B 2230/06; A63B 2230/202; A63B 2230/207; A63B 2230/30; A63B 2230/42; A63B 2230/50; A63B 24/0075; A61H 2230/06; A61H 2230/202; A61H 2230/207; A61H 2230/30; A61H 2230/42; A61H 2201/1215; A61H 2201/1261; A61H 2201/1633; A61H 2201/164; A61H 2201/1642; A61H 2201/1671; A61H 2201/501; A61H 2201/5012; A61H 2201/5043; A61H 2201/5046; A61H 2201/5048; A61H 2201/5061; A61H 2201/5064; A61H 2201/5069; A61H 2201/5071; A61H 2201/5092; A61H 2201/5097; A61H 2203/0431; A61H 2205/10; A61H 1/024; A61H 1/0214

See application file for complete search history.

(56) References Cited

U.S. PATENT DOCUMENTS

| | | | |
|---|---|---|---|
| 4,822,032 | A | 4/1989 | Whitmore et al. |
| 4,860,763 | A | 8/1989 | Schminke |
| 4,869,497 | A | 9/1989 | Stewart et al. |
| 4,932,650 | A | 6/1990 | Bingham et al. |
| 5,137,501 | A | 8/1992 | Mertesdorf |
| 5,161,430 | A | 11/1992 | Febey |
| 5,202,794 | A | 4/1993 | Schnee et al. |
| 5,240,417 | A | 8/1993 | Smithson et al. |
| 5,247,853 | A | 9/1993 | Dalebout |
| 5,256,117 | A | 10/1993 | Potts et al. |
| D342,299 | S | 12/1993 | Birrell et al. |
| 5,282,748 | A | 2/1994 | Little |
| 5,284,131 | A | 2/1994 | Gray |
| 5,316,532 | A | 5/1994 | Butler |
| 5,318,487 | A | 6/1994 | Golen |
| 5,324,241 | A | 6/1994 | Artigues et al. |
| 5,336,147 | A | 8/1994 | Sweeney, III |
| 5,338,272 | A | 8/1994 | Sweeney, III |
| 5,356,356 | A | 10/1994 | Hildebrandt |
| 5,361,649 | A | 11/1994 | Slocum, Jr. |
| D359,777 | S | 6/1995 | Hildebrandt |
| 5,429,140 | A | 7/1995 | Burdea et al. |
| 5,458,022 | A | 10/1995 | Mattfeld et al. |
| 5,487,713 | A | 1/1996 | Butler |
| 5,566,589 | A | 10/1996 | Buck |
| 5,580,338 | A | 12/1996 | Scelta et al. |
| 5,676,349 | A | 10/1997 | Wilson |
| 5,685,804 | A | 11/1997 | Whan-Tong et al. |
| 5,738,636 | A | 4/1998 | Saringer et al. |
| 5,860,941 | A | 1/1999 | Saringer et al. |
| 5,950,813 | A | 9/1999 | Hoskins et al. |
| 6,007,459 | A | 12/1999 | Burgess |
| D421,075 | S | 2/2000 | Hildebrandt |
| 6,053,847 | A | 4/2000 | Stearns et al. |
| 6,077,201 | A | 6/2000 | Cheng |
| 6,102,834 | A | 8/2000 | Chen |
| 6,110,130 | A | 8/2000 | Kramer |
| 6,155,958 | A | 12/2000 | Goldberg |
| 6,162,189 | A | 12/2000 | Girone et al. |
| 6,182,029 | B1 | 1/2001 | Friedman |
| D438,580 | S | 3/2001 | Shaw |
| 6,253,638 | B1 | 7/2001 | Bermudez |
| 6,267,735 | B1 | 7/2001 | Blanchard et al. |
| 6,273,863 | B1 | 8/2001 | Avni et al. |
| D450,100 | S | 11/2001 | Hsu |
| D450,101 | S | 11/2001 | Hsu |
| D451,972 | S | 12/2001 | Easley |
| D452,285 | S | 12/2001 | Easley |
| D454,605 | S | 3/2002 | Lee |
| 6,371,891 | B1 | 4/2002 | Speas |
| D459,776 | S | 7/2002 | Lee |
| 6,413,190 | B1 | 7/2002 | Wood et al. |
| 6,430,436 | B1 | 8/2002 | Richter |
| 6,436,058 | B1 | 8/2002 | Krahner et al. |
| 6,450,923 | B1 | 9/2002 | Vatti |
| 6,474,193 | B1 | 11/2002 | Farney |
| 6,491,649 | B1 | 12/2002 | Ombrellaro |
| 6,514,085 | B2 | 2/2003 | Slattery et al. |
| 6,535,861 | B1 | 3/2003 | OConnor et al. |
| 6,543,309 | B2 | 4/2003 | Heim |
| 6,589,139 | B1 | 7/2003 | Butterworth |
| 6,601,016 | B1 | 7/2003 | Brown et al. |
| 6,602,191 | B2 | 8/2003 | Quy |
| 6,613,000 | B1 | 9/2003 | Reinkensmeyer et al. |
| 6,626,800 | B1 | 9/2003 | Casler |
| 6,626,805 | B1 | 9/2003 | Lightbody |
| 6,640,122 | B2 | 10/2003 | Manoli |
| 6,640,662 | B1 | 11/2003 | Baxter |
| 6,652,425 | B1 | 11/2003 | Martin et al. |
| 6,659,946 | B1 | 12/2003 | Batchelor et al. |
| 6,820,517 | B1 | 11/2004 | Farney |
| 6,865,969 | B2 | 3/2005 | Stevens |
| 6,890,312 | B1 | 5/2005 | Priester et al. |
| 6,895,834 | B1 | 5/2005 | Baatz |
| 6,902,513 | B1 | 6/2005 | McClure |
| 7,058,453 | B2 | 6/2006 | Nelson et al. |
| 7,063,643 | B2 | 6/2006 | Arai |
| 7,156,665 | B1 | 1/2007 | OConnor et al. |
| 7,156,780 | B1 | 1/2007 | Fuchs et al. |
| 7,169,085 | B1 | 1/2007 | Killin et al. |
| 7,204,788 | B2 | 4/2007 | Andrews |
| 7,209,886 | B2 | 4/2007 | Kimmel |
| 7,226,394 | B2 | 6/2007 | Johnson |
| RE39,904 | E | 10/2007 | Lee |
| 7,406,003 | B2 | 7/2008 | Burkhardt et al. |
| 7,507,188 | B2 | 3/2009 | Nurre |
| 7,594,879 | B2 | 9/2009 | Johnson |
| 7,628,730 | B1 | 12/2009 | Watterson et al. |
| D610,635 | S | 2/2010 | Hildebrandt |
| 7,778,851 | B2 | 8/2010 | Schoenberg et al. |
| 7,809,601 | B2 | 10/2010 | Shaya et al. |
| 7,815,551 | B2 | 10/2010 | Merli |
| 7,833,135 | B2 | 11/2010 | Radow et al. |
| 7,837,472 | B1 | 11/2010 | Elsmore et al. |
| 7,890,342 | B1 | 2/2011 | Yruko |
| 7,955,219 | B2 | 6/2011 | Birrell et al. |
| 7,969,315 | B1 | 6/2011 | Ross et al. |
| 7,988,599 | B2 | 8/2011 | Ainsworth et al. |
| 8,007,405 | B2 | 8/2011 | Burnfield |
| 8,012,107 | B2 | 9/2011 | Einav et al. |
| 8,021,270 | B2 | 9/2011 | D'Eredita |
| 8,038,578 | B2 | 10/2011 | Olrik et al. |
| 8,079,937 | B2 | 12/2011 | Bedell |

(56) References Cited

U.S. PATENT DOCUMENTS

| | | | | |
|---|---|---|---|---|
| 8,113,991 | B2 | 2/2012 | Kutliroff | |
| 8,172,724 | B2 | 5/2012 | Solomon | |
| 8,177,732 | B2 | 5/2012 | Einav et al. | |
| 8,244,566 | B1 | 8/2012 | Coley | |
| 8,287,434 | B2 | 10/2012 | Zavadsky et al. | |
| 8,298,123 | B2 | 10/2012 | Hickman | |
| 8,371,990 | B2 | 2/2013 | Shea | |
| 8,396,804 | B1 | 3/2013 | Dala | |
| 8,419,593 | B2 | 4/2013 | Ainsworth et al. | |
| 8,465,398 | B2 | 6/2013 | Lee et al. | |
| 8,503,086 | B2 | 8/2013 | French | |
| 8,506,458 | B2 | 8/2013 | Dugan | |
| 8,515,777 | B1 | 8/2013 | Rajasenan | |
| 8,540,515 | B2 | 9/2013 | Williams et al. | |
| 8,540,516 | B2 | 9/2013 | Williams et al. | |
| 8,556,778 | B1 | 10/2013 | Dugan | |
| 8,607,465 | B1 | 12/2013 | Edwards | |
| 8,613,689 | B2 | 12/2013 | Dyer et al. | |
| 8,615,529 | B2 | 12/2013 | Reiner | |
| 8,672,812 | B2 | 3/2014 | Dugan | |
| 8,751,264 | B2 | 6/2014 | Beraja et al. | |
| 8,784,273 | B2 | 7/2014 | Dugan | |
| 8,818,496 | B2 | 8/2014 | Dziubinski et al. | |
| 8,823,448 | B1 | 9/2014 | Shen | |
| 8,845,493 | B2 | 9/2014 | Watterson et al. | |
| 8,849,681 | B2 | 9/2014 | Hargrove et al. | |
| 8,864,628 | B2 | 10/2014 | Boyette et al. | |
| 8,893,287 | B2 | 11/2014 | Gjonej et al. | |
| 8,911,327 | B1 | 12/2014 | Boyette | |
| 8,979,711 | B2 | 3/2015 | Dugan | |
| 9,004,598 | B2 | 4/2015 | Weber | |
| 9,044,630 | B1 | 6/2015 | Lampert et al. | |
| 9,167,281 | B2 | 10/2015 | Petrov et al. | |
| D744,050 | S | 11/2015 | Colburn | |
| 9,248,071 | B1 | 2/2016 | Brenda | |
| 9,256,711 | B2 | 2/2016 | Horseman | |
| 9,272,091 | B2 * | 3/2016 | Skelton | A61M 5/1723 |
| 9,272,185 | B2 | 3/2016 | Dugan | |
| 9,283,434 | B1 | 3/2016 | Wu | |
| 9,295,878 | B2 | 3/2016 | Corbalis et al. | |
| 9,311,789 | B1 | 4/2016 | Gwin | |
| 9,312,907 | B2 | 4/2016 | Auchinleck et al. | |
| 9,367,668 | B2 | 6/2016 | Flynt et al. | |
| 9,409,054 | B2 | 8/2016 | Dugan | |
| 9,443,205 | B2 | 9/2016 | Wall | |
| 9,474,935 | B2 | 10/2016 | Abbondanza et al. | |
| 9,480,873 | B2 | 11/2016 | Chuang | |
| 9,481,428 | B2 | 11/2016 | Gros | |
| 9,514,277 | B2 | 12/2016 | Hassing et al. | |
| 9,566,472 | B2 | 2/2017 | Dugan | |
| 9,579,056 | B2 | 2/2017 | Rosenbek et al. | |
| 9,629,558 | B2 | 4/2017 | Yuen et al. | |
| 9,640,057 | B1 | 5/2017 | Ross | |
| 9,707,147 | B2 | 7/2017 | Levital et al. | |
| 9,713,744 | B2 | 7/2017 | Suzuki | |
| D794,142 | S | 8/2017 | Zhou | |
| 9,717,947 | B2 | 8/2017 | Lin | |
| 9,737,761 | B1 | 8/2017 | Govindarajan | |
| 9,757,612 | B2 | 9/2017 | Weber | |
| 9,773,330 | B1 | 9/2017 | Douglas | |
| 9,782,621 | B2 | 10/2017 | Chiang et al. | |
| 9,802,076 | B2 | 10/2017 | Murray et al. | |
| 9,802,081 | B2 | 10/2017 | Ridgel et al. | |
| 9,813,239 | B2 | 11/2017 | Chee et al. | |
| 9,827,445 | B2 | 11/2017 | Marcos et al. | |
| 9,849,337 | B2 | 12/2017 | Roman et al. | |
| 9,868,028 | B2 | 1/2018 | Shin | |
| 9,872,087 | B2 | 1/2018 | DelloStritto et al. | |
| 9,872,637 | B2 | 1/2018 | Kording et al. | |
| 9,914,053 | B2 | 3/2018 | Dugan | |
| 9,919,198 | B2 | 3/2018 | Romeo et al. | |
| 9,937,382 | B2 | 4/2018 | Dugan | |
| 9,939,784 | B1 | 4/2018 | Berardinelli | |
| 9,974,478 | B1 * | 5/2018 | Brokaw | A61B 5/486 |
| 9,977,587 | B2 | 5/2018 | Mountain | |
| 9,993,181 | B2 | 6/2018 | Ross | |
| 9,997,082 | B2 | 6/2018 | Kaleal | |
| 10,004,946 | B2 | 6/2018 | Ross | |
| 10,026,052 | B2 | 7/2018 | Brown et al. | |
| D826,349 | S | 8/2018 | Oblamski | |
| 10,055,550 | B2 | 8/2018 | Goetz | |
| 10,058,473 | B2 | 8/2018 | Oshima et al. | |
| 10,074,148 | B2 | 9/2018 | Cashman et al. | |
| 10,089,443 | B2 | 10/2018 | Miller et al. | |
| 10,111,643 | B2 | 10/2018 | Shulhauser et al. | |
| 10,130,311 | B1 | 11/2018 | De Sapio et al. | |
| 10,137,328 | B2 | 11/2018 | Baudhuin | |
| 10,143,395 | B2 | 12/2018 | Chakravarthy et al. | |
| 10,155,134 | B2 | 12/2018 | Dugan | |
| 10,159,872 | B2 | 12/2018 | Sasaki et al. | |
| 10,173,094 | B2 | 1/2019 | Gomberg | |
| 10,173,095 | B2 | 1/2019 | Gomberg et al. | |
| 10,173,096 | B2 | 1/2019 | Gomberg et al. | |
| 10,173,097 | B2 | 1/2019 | Gomberg et al. | |
| 10,198,928 | B1 | 2/2019 | Ross et al. | |
| 10,226,663 | B2 | 3/2019 | Gomberg et al. | |
| 10,231,664 | B2 | 3/2019 | Ganesh | |
| 10,244,990 | B2 | 4/2019 | Hu et al. | |
| 10,258,823 | B2 | 4/2019 | Cole | |
| 10,322,315 | B2 | 6/2019 | Foley et al. | |
| 10,325,070 | B2 | 6/2019 | Beale et al. | |
| 10,327,697 | B1 | 6/2019 | Stein et al. | |
| 10,362,940 | B2 * | 7/2019 | Tran | G08B 25/016 |
| 10,369,021 | B2 | 8/2019 | Zoss et al. | |
| 10,380,866 | B1 | 8/2019 | Ross et al. | |
| 10,413,222 | B1 | 9/2019 | Kayyall | |
| 10,413,238 | B1 | 9/2019 | Cooper | |
| 10,424,033 | B2 | 9/2019 | Romeo | |
| 10,430,552 | B2 | 10/2019 | Mihai | |
| D866,957 | S | 11/2019 | Ross et al. | |
| 10,468,131 | B2 | 11/2019 | Macoviak et al. | |
| 10,475,323 | B1 | 11/2019 | Ross | |
| 10,475,537 | B2 | 11/2019 | Purdie et al. | |
| 10,492,977 | B2 | 12/2019 | Kapure et al. | |
| 10,507,358 | B2 | 12/2019 | Kinnunen et al. | |
| 10,542,914 | B2 | 1/2020 | Forth et al. | |
| 10,546,467 | B1 | 1/2020 | Luciano, Jr. et al. | |
| 10,569,122 | B2 | 2/2020 | Johnson | |
| 10,572,626 | B2 | 2/2020 | Balram | |
| 10,576,331 | B2 | 3/2020 | Kuo | |
| 10,581,896 | B2 | 3/2020 | Nachenberg | |
| 10,625,114 | B2 | 4/2020 | Ercanbrack | |
| 10,646,746 | B1 | 5/2020 | Gomberg et al. | |
| 10,660,534 | B2 | 5/2020 | Lee et al. | |
| 10,678,890 | B2 | 6/2020 | Bitran et al. | |
| 10,685,092 | B2 | 6/2020 | Paparella et al. | |
| 10,741,285 | B2 | 8/2020 | Moturu | |
| 10,777,200 | B2 | 9/2020 | Will et al. | |
| D899,605 | S | 10/2020 | Ross et al. | |
| 10,792,495 | B2 | 10/2020 | Izvorski et al. | |
| 10,814,170 | B2 | 10/2020 | Wang et al. | |
| 10,857,426 | B1 | 12/2020 | Neumann | |
| 10,867,695 | B2 | 12/2020 | Neagle | |
| 10,874,905 | B2 | 12/2020 | Belson et al. | |
| D907,143 | S | 1/2021 | Ach et al. | |
| 10,881,911 | B2 | 1/2021 | Kwon et al. | |
| 10,902,944 | B1 | 1/2021 | Casey | |
| 10,918,332 | B2 | 2/2021 | Belson et al. | |
| 10,931,643 | B1 | 2/2021 | Neumann | |
| 10,987,176 | B2 | 4/2021 | Poltaretskyi et al. | |
| 10,991,463 | B2 | 4/2021 | Kutzko et al. | |
| 11,000,735 | B2 | 5/2021 | Orady et al. | |
| 11,045,709 | B2 | 6/2021 | Putnam | |
| 11,065,170 | B2 | 7/2021 | Yang et al. | |
| 11,065,527 | B2 | 7/2021 | Putnam | |
| 11,069,436 | B2 | 7/2021 | Mason et al. | |
| 11,071,597 | B2 | 7/2021 | Posnack et al. | |
| 11,075,000 | B2 | 7/2021 | Mason et al. | |
| D928,635 | S | 8/2021 | Hacking et al. | |
| 11,087,865 | B2 | 8/2021 | Mason et al. | |
| 11,094,400 | B2 | 8/2021 | Riley et al. | |
| 11,101,028 | B2 | 8/2021 | Mason et al. | |
| 11,107,591 | B1 | 8/2021 | Mason | |
| 11,139,060 | B2 | 10/2021 | Mason et al. | |

(56) References Cited

U.S. PATENT DOCUMENTS

| | | | |
|---|---|---|---|
| 11,185,735 | B2 | 11/2021 | Arn et al. |
| 11,185,738 | B1 | 11/2021 | McKirdy et al. |
| D939,096 | S | 12/2021 | Lee |
| D939,644 | S | 12/2021 | Ach et al. |
| D940,797 | S | 1/2022 | Ach et al. |
| D940,891 | S | 1/2022 | Lee |
| 11,229,727 | B2 | 1/2022 | Tatonetti |
| 11,229,788 | B1 | 1/2022 | John |
| 11,265,234 | B2 | 3/2022 | Guaneri et al. |
| 11,270,795 | B2 | 3/2022 | Mason et al. |
| 11,272,879 | B2 | 3/2022 | Wiedenhoefer et al. |
| 11,278,766 | B2 | 3/2022 | Lee |
| 11,282,599 | B2 | 3/2022 | Mason et al. |
| 11,282,604 | B2 | 3/2022 | Mason et al. |
| 11,282,608 | B2 | 3/2022 | Mason et al. |
| 11,284,797 | B2 | 3/2022 | Mason et al. |
| D948,639 | S | 4/2022 | Ach et al. |
| 11,295,848 | B2 | 4/2022 | Mason et al. |
| 11,298,284 | B2 | 4/2022 | Bayerlein |
| 11,309,085 | B2 | 4/2022 | Mason et al. |
| 11,317,975 | B2 | 5/2022 | Mason et al. |
| 11,325,005 | B2 | 5/2022 | Mason et al. |
| 11,328,807 | B2 | 5/2022 | Mason et al. |
| 11,331,537 | B1 | 5/2022 | Ketchell |
| 11,337,648 | B2 | 5/2022 | Mason |
| 11,347,829 | B1 | 5/2022 | Sclar et al. |
| 11,348,683 | B2 | 5/2022 | Guaneri et al. |
| 11,370,328 | B2 | 6/2022 | Main |
| 11,376,470 | B2 | 7/2022 | Weldemariam |
| 11,404,150 | B2 | 8/2022 | Guaneri et al. |
| 11,410,768 | B2 | 8/2022 | Mason et al. |
| 11,422,841 | B2 | 8/2022 | Jeong |
| 11,437,137 | B1 | 9/2022 | Harris |
| 11,495,355 | B2 | 11/2022 | McNutt et al. |
| 11,508,258 | B2 | 11/2022 | Nakashima et al. |
| 11,508,482 | B2 | 11/2022 | Mason et al. |
| 11,515,021 | B2 | 11/2022 | Mason |
| 11,515,028 | B2 | 11/2022 | Mason |
| 11,524,210 | B2 | 12/2022 | Kim et al. |
| 11,527,326 | B2 | 12/2022 | McNair et al. |
| 11,532,402 | B2 | 12/2022 | Farley et al. |
| 11,534,654 | B2 | 12/2022 | Silcock et al. |
| D976,339 | S | 1/2023 | Li |
| 11,541,274 | B2 | 1/2023 | Hacking |
| 11,553,969 | B1 | 1/2023 | Lang et al. |
| 11,621,067 | B1 | 4/2023 | Nolan |
| 11,636,944 | B2 | 4/2023 | Hanrahan et al. |
| 11,654,327 | B2 | 5/2023 | Phillips et al. |
| 11,663,673 | B2 | 5/2023 | Pyles |
| 11,673,024 | B2 | 6/2023 | Omid-Zohoor |
| 11,701,548 | B2 | 7/2023 | Posnack et al. |
| 11,756,666 | B2 | 9/2023 | Rosenberg |
| 11,776,676 | B2 | 10/2023 | Savolainen |
| 11,944,579 | B2 * | 4/2024 | Sankai .................. A61B 5/395 |
| 11,957,960 | B2 | 4/2024 | Bissonnette et al. |
| 12,004,871 | B1 | 6/2024 | Fazeli |
| 12,020,511 | B1 | 6/2024 | Denton et al. |
| 12,042,714 | B1 | 7/2024 | Campbell |
| 12,057,210 | B2 | 8/2024 | Akinola et al. |
| 12,176,091 | B2 | 12/2024 | Rosenberg |
| 12,205,704 | B2 | 1/2025 | Hosoi et al. |
| 2001/0044573 | A1 | 11/2001 | Manoli |
| 2002/0010596 | A1 | 1/2002 | Matory |
| 2002/0072452 | A1 | 6/2002 | Torkelson |
| 2002/0123715 | A1 | 9/2002 | Sorenson |
| 2002/0143279 | A1 | 10/2002 | Porter et al. |
| 2002/0160883 | A1 | 10/2002 | Dugan |
| 2002/0183599 | A1 | 12/2002 | Castellanos |
| 2003/0013072 | A1 | 1/2003 | Thomas |
| 2003/0036683 | A1 | 2/2003 | Kehr et al. |
| 2003/0064860 | A1 | 4/2003 | Yamashita et al. |
| 2003/0064863 | A1 | 4/2003 | Chen |
| 2003/0083596 | A1 | 5/2003 | Kramer et al. |
| 2003/0092536 | A1 | 5/2003 | Romanelli et al. |
| 2003/0181832 | A1 | 9/2003 | Carnahan et al. |
| 2004/0072652 | A1 | 4/2004 | Alessandri et al. |
| 2004/0102931 | A1 | 5/2004 | Ellis et al. |
| 2004/0106502 | A1 | 6/2004 | Sher |
| 2004/0147969 | A1 | 7/2004 | Mann et al. |
| 2004/0172093 | A1 | 9/2004 | Rummerfield |
| 2004/0194572 | A1 | 10/2004 | Kim |
| 2004/0197727 | A1 | 10/2004 | Sachdeva et al. |
| 2004/0204959 | A1 | 10/2004 | Moreano et al. |
| 2005/0015118 | A1 | 1/2005 | Davis et al. |
| 2005/0020411 | A1 | 1/2005 | Andrews |
| 2005/0043145 | A1 | 2/2005 | Anderson |
| 2005/0043153 | A1 | 2/2005 | Krietzman |
| 2005/0049122 | A1 | 3/2005 | Vallone et al. |
| 2005/0085346 | A1 | 4/2005 | Johnson |
| 2005/0085353 | A1 | 4/2005 | Johnson |
| 2005/0115561 | A1 | 6/2005 | Stahmann |
| 2005/0143641 | A1 | 6/2005 | Tashiro |
| 2005/0274220 | A1 | 12/2005 | Reboullet |
| 2006/0003871 | A1 | 1/2006 | Houghton et al. |
| 2006/0046905 | A1 | 3/2006 | Doody, Jr. et al. |
| 2006/0058648 | A1 | 3/2006 | Meier |
| 2006/0064136 | A1 | 3/2006 | Wang |
| 2006/0064329 | A1 | 3/2006 | Abolfathi et al. |
| 2006/0129432 | A1 | 6/2006 | Choi et al. |
| 2006/0199700 | A1 | 9/2006 | LaStayo et al. |
| 2006/0247095 | A1 | 11/2006 | Rummerfield |
| 2006/0277074 | A1 | 12/2006 | Einav |
| 2007/0042868 | A1 | 2/2007 | Fisher et al. |
| 2007/0118389 | A1 | 5/2007 | Shipon |
| 2007/0118406 | A1 | 5/2007 | Killin et al. |
| 2007/0136099 | A1 | 6/2007 | Neligh |
| 2007/0137307 | A1 | 6/2007 | Gruben et al. |
| 2007/0173392 | A1 | 7/2007 | Stanford |
| 2007/0184414 | A1 | 8/2007 | Perez |
| 2007/0194939 | A1 | 8/2007 | Alvarez et al. |
| 2007/0219059 | A1 | 9/2007 | Schwartz |
| 2007/0271065 | A1 | 11/2007 | Gupta et al. |
| 2007/0287597 | A1 | 12/2007 | Cameron |
| 2008/0021834 | A1 | 1/2008 | Holla et al. |
| 2008/0077619 | A1 | 3/2008 | Gilley et al. |
| 2008/0082356 | A1 | 4/2008 | Friedlander et al. |
| 2008/0096726 | A1 | 4/2008 | Riley et al. |
| 2008/0103023 | A1 | 5/2008 | Chung |
| 2008/0153592 | A1 | 6/2008 | James-Herbert |
| 2008/0161166 | A1 | 7/2008 | Lo |
| 2008/0161733 | A1 | 7/2008 | Einav et al. |
| 2008/0183500 | A1 | 7/2008 | Banigan |
| 2008/0281633 | A1 | 11/2008 | Burdea et al. |
| 2008/0300914 | A1 | 12/2008 | Karkanias et al. |
| 2008/0312040 | A1 | 12/2008 | Ochi |
| 2008/0319330 | A1 | 12/2008 | Juntunen |
| 2009/0011907 | A1 | 1/2009 | Radow et al. |
| 2009/0037334 | A1 | 2/2009 | Hsu |
| 2009/0058635 | A1 | 3/2009 | LaLonde et al. |
| 2009/0070138 | A1 | 3/2009 | Langheier et al. |
| 2009/0157617 | A1 | 6/2009 | Herlocker |
| 2009/0211395 | A1 | 8/2009 | Mule |
| 2009/0270227 | A1 | 10/2009 | Ashby et al. |
| 2009/0287503 | A1 | 11/2009 | Angell et al. |
| 2009/0299766 | A1 | 12/2009 | Friedlander et al. |
| 2010/0048358 | A1 | 2/2010 | Tchao et al. |
| 2010/0062818 | A1 | 3/2010 | Haughay, Jr. |
| 2010/0076786 | A1 | 3/2010 | Dalton et al. |
| 2010/0121160 | A1 | 5/2010 | Stark et al. |
| 2010/0173747 | A1 | 7/2010 | Chen et al. |
| 2010/0216168 | A1 | 8/2010 | Heinzman et al. |
| 2010/0234184 | A1 | 9/2010 | Le Page et al. |
| 2010/0248899 | A1 | 9/2010 | Bedell et al. |
| 2010/0248905 | A1 | 9/2010 | Lu |
| 2010/0262052 | A1 | 10/2010 | Lunau et al. |
| 2010/0268304 | A1 | 10/2010 | Matos |
| 2010/0293003 | A1 | 11/2010 | Abbo |
| 2010/0298102 | A1 | 11/2010 | Bosecker et al. |
| 2010/0326207 | A1 | 12/2010 | Topel |
| 2010/0332583 | A1 | 12/2010 | Szabo |
| 2011/0010188 | A1 | 1/2011 | Yoshikawa et al. |
| 2011/0047108 | A1 | 2/2011 | Chakrabarty et al. |
| 2011/0082007 | A1 | 4/2011 | Birrell |
| 2011/0087137 | A1 | 4/2011 | Hanoun |

(56) References Cited

U.S. PATENT DOCUMENTS

2011/0119212 A1 5/2011 De Bruin et al.
2011/0172059 A1 7/2011 Watterson et al.
2011/0195819 A1 8/2011 Shaw et al.
2011/0218462 A1 9/2011 Smith
2011/0218814 A1 9/2011 Coats
2011/0275483 A1 11/2011 Dugan
2011/0281249 A1 11/2011 Gammell et al.
2011/0306846 A1 12/2011 Osorio
2012/0041771 A1 2/2012 Cosentino et al.
2012/0065987 A1 3/2012 Farooq et al.
2012/0116258 A1 5/2012 Lee
2012/0130196 A1 5/2012 Jain et al.
2012/0130197 A1 5/2012 Kugler et al.
2012/0167709 A1 7/2012 Chen et al.
2012/0183939 A1 7/2012 Aragones et al.
2012/0190502 A1 7/2012 Paulus et al.
2012/0232438 A1 9/2012 Cataldi et al.
2012/0248346 A1 10/2012 Chowdhary
2012/0253241 A1 10/2012 Levital
2012/0259648 A1 10/2012 Mallon et al.
2012/0259649 A1 10/2012 Mallon et al.
2012/0278759 A1 11/2012 Curl et al.
2012/0295240 A1 11/2012 Walker et al.
2012/0296455 A1 11/2012 Ohnemus et al.
2012/0310667 A1 12/2012 Altman et al.
2013/0066647 A1 3/2013 Andrie
2013/0079925 A1 3/2013 Alaklabi et al.
2013/0083054 A1 4/2013 Bayouk
2013/0108594 A1 5/2013 Martin-Rendon et al.
2013/0110545 A1 5/2013 Smallwood
2013/0123071 A1 5/2013 Rhea
2013/0123667 A1 5/2013 Komatireddy et al.
2013/0137550 A1 5/2013 Skinner et al.
2013/0137552 A1 5/2013 Kemp et al.
2013/0158368 A1 6/2013 Pacione
2013/0165195 A1 6/2013 Watterson
2013/0171599 A1 7/2013 Bleich
2013/0173305 A1 7/2013 Hyde
2013/0178334 A1 7/2013 Brammer
2013/0211281 A1 8/2013 Ross et al.
2013/0211774 A1 8/2013 Bentley
2013/0253943 A1 9/2013 Lee et al.
2013/0274069 A1 10/2013 Watterson et al.
2013/0296987 A1 11/2013 Rogers et al.
2013/0318027 A1 11/2013 Almogy et al.
2013/0332616 A1 12/2013 Landwehr
2013/0345025 A1 12/2013 van der Merwe
2014/0006042 A1 1/2014 Keefe et al.
2014/0011640 A1 1/2014 Dugan
2014/0031174 A1 1/2014 Huang
2014/0038781 A1 2/2014 Foley et al.
2014/0062900 A1 3/2014 Kaula et al.
2014/0074179 A1 3/2014 Heldman et al.
2014/0089836 A1 3/2014 Damani et al.
2014/0108035 A1 4/2014 Akbay
2014/0113261 A1 4/2014 Akiba
2014/0113768 A1 4/2014 Lin et al.
2014/0135173 A1 5/2014 Watterson
2014/0149129 A1 5/2014 Getchius
2014/0155129 A1 6/2014 Dugan
2014/0163439 A1 6/2014 Uryash et al.
2014/0170607 A1 6/2014 Hsiao
2014/0172442 A1 6/2014 Broderick
2014/0172460 A1 6/2014 Kohli
2014/0172514 A1 6/2014 Schumann et al.
2014/0188009 A1 7/2014 Lange et al.
2014/0194250 A1 7/2014 Reich et al.
2014/0194251 A1 7/2014 Reich et al.
2014/0200414 A1 7/2014 Osorio
2014/0207264 A1 7/2014 Quy
2014/0207486 A1 7/2014 Carty et al.
2014/0228649 A1 8/2014 Rayner et al.
2014/0246499 A1 9/2014 Proud et al.
2014/0256511 A1 9/2014 Smith
2014/0257837 A1 9/2014 Walker et al.
2014/0274565 A1 9/2014 Boyette et al.
2014/0274622 A1 9/2014 Leonhard
2014/0275816 A1 9/2014 Sandmore
2014/0303540 A1 10/2014 Baym
2014/0309083 A1 10/2014 Dugan
2014/0322686 A1 10/2014 Kang
2014/0347265 A1 11/2014 Aimone et al.
2014/0371816 A1 12/2014 Matos
2014/0372133 A1 12/2014 Austrum et al.
2015/0025816 A1 1/2015 Ross
2015/0045700 A1 2/2015 Cavanagh et al.
2015/0046192 A1 2/2015 Raduchel
2015/0051721 A1 2/2015 Cheng
2015/0065213 A1 3/2015 Dugan
2015/0073814 A1 3/2015 Linebaugh
2015/0088544 A1 3/2015 Goldberg
2015/0094192 A1 4/2015 Skwortsow et al.
2015/0099458 A1 4/2015 Weisner et al.
2015/0099952 A1 4/2015 Lain et al.
2015/0111644 A1 4/2015 Larson
2015/0112230 A1 4/2015 Iglesias
2015/0112702 A1 4/2015 Joao et al.
2015/0130830 A1 5/2015 Nagasaki
2015/0141200 A1 5/2015 Murray et al.
2015/0142142 A1 5/2015 Campana Aguilera et al.
2015/0149217 A1 5/2015 Kaburagi
2015/0151162 A1 6/2015 Dugan
2015/0157918 A1 6/2015 Tracy
2015/0157938 A1 6/2015 Domansky et al.
2015/0161331 A1 6/2015 Oleynik
2015/0161876 A1 6/2015 Castillo
2015/0174446 A1 6/2015 Chiang
2015/0196804 A1 7/2015 Koduri
2015/0196805 A1 7/2015 Koduri
2015/0199494 A1 7/2015 Koduri
2015/0217056 A1 8/2015 Kadavy et al.
2015/0251074 A1 9/2015 Ahmed et al.
2015/0257679 A1 9/2015 Ross
2015/0265209 A1 9/2015 Zhang
2015/0273272 A1 10/2015 Wang
2015/0290061 A1 10/2015 Stafford et al.
2015/0331997 A1 11/2015 Joao
2015/0335950 A1 11/2015 Eder
2015/0335951 A1 11/2015 Eder
2015/0339442 A1 11/2015 Oleynik
2015/0341812 A1 11/2015 Dion et al.
2015/0351664 A1 12/2015 Ross
2015/0351665 A1 12/2015 Ross
2015/0359467 A1 12/2015 Tran
2015/0360069 A1 12/2015 Marti et al.
2015/0379232 A1 12/2015 Mainwaring et al.
2015/0379430 A1 12/2015 Dirac et al.
2016/0004820 A1 1/2016 Moore
2016/0007885 A1 1/2016 Basta
2016/0009338 A1 1/2016 Biderman
2016/0015995 A1 1/2016 Leung et al.
2016/0023081 A1 1/2016 Popa-Simil et al.
2016/0045170 A1 2/2016 Migita
2016/0081594 A1 3/2016 Gaddipati
2016/0084869 A1 3/2016 Yuen
2016/0086500 A1 3/2016 Kaleal, III
2016/0096073 A1 4/2016 Rahman et al.
2016/0117471 A1 4/2016 Belt et al.
2016/0132643 A1 5/2016 Radhakrishna et al.
2016/0140319 A1 5/2016 Stark
2016/0143593 A1 5/2016 Fu et al.
2016/0151670 A1 6/2016 Dugan
2016/0158534 A1 6/2016 Guarraia et al.
2016/0166833 A1 6/2016 Burn
2016/0166881 A1 6/2016 Ridgel et al.
2016/0193306 A1 7/2016 Rabovsky et al.
2016/0197918 A1 7/2016 Turgeman et al.
2016/0213924 A1 7/2016 Coleman
2016/0232321 A1 8/2016 Silverman
2016/0250519 A1 9/2016 Watterson
2016/0275259 A1 9/2016 Nolan et al.
2016/0287166 A1 10/2016 Tran
2016/0294837 A1 10/2016 Turgeman
2016/0302666 A1 10/2016 Shaya

(56) References Cited

U.S. PATENT DOCUMENTS

| | | | |
|---|---|---|---|
| 2016/0302721 | A1 | 10/2016 | Wiedenhoefer et al. |
| 2016/0317869 | A1 | 11/2016 | Dugan |
| 2016/0322078 | A1 | 11/2016 | Bose et al. |
| 2016/0325140 | A1 | 11/2016 | Wu |
| 2016/0332028 | A1 | 11/2016 | Melnik |
| 2016/0345841 | A1 | 12/2016 | Jang et al. |
| 2016/0354636 | A1 | 12/2016 | Jang |
| 2016/0361025 | A1 | 12/2016 | Reicher et al. |
| 2016/0361597 | A1 | 12/2016 | Cole et al. |
| 2016/0373477 | A1 | 12/2016 | Moyle |
| 2017/0000422 | A1 | 1/2017 | Moturu et al. |
| 2017/0004260 | A1 | 1/2017 | Moturu et al. |
| 2017/0011179 | A1 | 1/2017 | Arshad et al. |
| 2017/0017760 | A1 | 1/2017 | Freese et al. |
| 2017/0032092 | A1 | 2/2017 | Mink et al. |
| 2017/0033375 | A1 | 2/2017 | Ohmori et al. |
| 2017/0042467 | A1 | 2/2017 | Herr et al. |
| 2017/0043160 | A1 | 2/2017 | Goodall et al. |
| 2017/0046488 | A1 | 2/2017 | Pereira |
| 2017/0065851 | A1 | 3/2017 | Deluca et al. |
| 2017/0069223 | A1 | 3/2017 | Cramer et al. |
| 2017/0080281 | A1 | 3/2017 | Hartman |
| 2017/0080320 | A1 | 3/2017 | Smith |
| 2017/0091422 | A1 | 3/2017 | Kumar et al. |
| 2017/0095670 | A1 | 4/2017 | Ghaffari et al. |
| 2017/0095692 | A1 | 4/2017 | Chang et al. |
| 2017/0095693 | A1 | 4/2017 | Chang et al. |
| 2017/0097964 | A1 | 4/2017 | Sorrentino |
| 2017/0100637 | A1 | 4/2017 | Princen et al. |
| 2017/0106242 | A1 | 4/2017 | Dugan |
| 2017/0113092 | A1 | 4/2017 | Johnson |
| 2017/0128769 | A1 | 5/2017 | Long et al. |
| 2017/0132947 | A1 | 5/2017 | Maeda et al. |
| 2017/0136296 | A1 | 5/2017 | Barrera et al. |
| 2017/0136297 | A1 | 5/2017 | Penie |
| 2017/0136298 | A1 | 5/2017 | Bae |
| 2017/0143261 | A1 | 5/2017 | Wiedenhoefer et al. |
| 2017/0143262 | A1 | 5/2017 | Kurunmaki |
| 2017/0147752 | A1 | 5/2017 | Toru |
| 2017/0147789 | A1 | 5/2017 | Wiedenhoefer et al. |
| 2017/0148297 | A1 | 5/2017 | Ross |
| 2017/0168555 | A1 | 6/2017 | Munoz et al. |
| 2017/0169177 | A1 | 6/2017 | Beale |
| 2017/0173391 | A1 | 6/2017 | Wiebe |
| 2017/0181698 | A1 | 6/2017 | Wiedenhoefer et al. |
| 2017/0190052 | A1 | 7/2017 | Jaekel et al. |
| 2017/0200264 | A1 | 7/2017 | Park |
| 2017/0202724 | A1 | 7/2017 | De Rossi |
| 2017/0203157 | A1 | 7/2017 | Volkerink |
| 2017/0209766 | A1 | 7/2017 | Riley et al. |
| 2017/0220751 | A1 | 8/2017 | Davis |
| 2017/0228517 | A1 | 8/2017 | Saliman et al. |
| 2017/0235882 | A1 | 8/2017 | Orlov et al. |
| 2017/0235906 | A1 | 8/2017 | Dorris et al. |
| 2017/0243028 | A1 | 8/2017 | LaFever et al. |
| 2017/0258370 | A1 | 9/2017 | Plotnik-Peleg et al. |
| 2017/0262604 | A1 | 9/2017 | Francois |
| 2017/0265800 | A1 | 9/2017 | Auchinleck et al. |
| 2017/0266501 | A1 | 9/2017 | Sanders et al. |
| 2017/0270260 | A1 | 9/2017 | Shetty |
| 2017/0277841 | A1 | 9/2017 | Shankar et al. |
| 2017/0278209 | A1 | 9/2017 | Olsen et al. |
| 2017/0282015 | A1 | 10/2017 | Wicks et al. |
| 2017/0283508 | A1 | 10/2017 | Demopulos et al. |
| 2017/0286621 | A1 | 10/2017 | Cox |
| 2017/0291067 | A1 | 10/2017 | Jang et al. |
| 2017/0296861 | A1 | 10/2017 | Burkinshaw |
| 2017/0300654 | A1 | 10/2017 | Stein et al. |
| 2017/0304024 | A1 | 10/2017 | Nobrega |
| 2017/0312614 | A1 | 11/2017 | Tran et al. |
| 2017/0323481 | A1 | 11/2017 | Tran et al. |
| 2017/0329917 | A1 | 11/2017 | McRaith et al. |
| 2017/0329933 | A1 | 11/2017 | Brust |
| 2017/0333755 | A1 | 11/2017 | Rider |
| 2017/0337033 | A1 | 11/2017 | Duyan et al. |
| 2017/0337334 | A1 | 11/2017 | Stanczak |
| 2017/0344726 | A1 | 11/2017 | Duffy et al. |
| 2017/0347923 | A1 | 12/2017 | Roh |
| 2017/0352157 | A1 | 12/2017 | Madabhushi |
| 2017/0360586 | A1 | 12/2017 | Dempers et al. |
| 2017/0361165 | A1 | 12/2017 | Miller et al. |
| 2017/0367606 | A1 | 12/2017 | Lee |
| 2017/0368413 | A1 | 12/2017 | Shavit |
| 2018/0017806 | A1 | 1/2018 | Wang et al. |
| 2018/0028896 | A1 | 2/2018 | Ray |
| 2018/0036591 | A1 | 2/2018 | King et al. |
| 2018/0036593 | A1 | 2/2018 | Ridgel et al. |
| 2018/0052962 | A1 | 2/2018 | Van Der Koijk et al. |
| 2018/0052968 | A1 | 2/2018 | Hickle et al. |
| 2018/0056104 | A1 | 3/2018 | Cromie et al. |
| 2018/0056130 | A1 | 3/2018 | Bitran et al. |
| 2018/0060494 | A1 | 3/2018 | Dias et al. |
| 2018/0070864 | A1 | 3/2018 | Schuster |
| 2018/0071565 | A1 | 3/2018 | Gomberg et al. |
| 2018/0071566 | A1 | 3/2018 | Gomberg et al. |
| 2018/0071569 | A1 | 3/2018 | Gomberg et al. |
| 2018/0071570 | A1 | 3/2018 | Gomberg et al. |
| 2018/0071571 | A1 | 3/2018 | Gomberg et al. |
| 2018/0071572 | A1 | 3/2018 | Gomberg et al. |
| 2018/0071583 | A1 | 3/2018 | Paiz |
| 2018/0075205 | A1 | 3/2018 | Moturu et al. |
| 2018/0078149 | A1 | 3/2018 | Fonte et al. |
| 2018/0078182 | A1 | 3/2018 | Chen |
| 2018/0078843 | A1 | 3/2018 | Tran et al. |
| 2018/0085615 | A1 | 3/2018 | Astolfi et al. |
| 2018/0085630 | A1 | 3/2018 | Capell |
| 2018/0089385 | A1 | 3/2018 | Gupta |
| 2018/0096111 | A1 | 4/2018 | Wells et al. |
| 2018/0099178 | A1 | 4/2018 | Schaefer et al. |
| 2018/0102190 | A1 | 4/2018 | Hogue et al. |
| 2018/0103859 | A1 | 4/2018 | Provenzano |
| 2018/0108430 | A1 | 4/2018 | Vo |
| 2018/0113985 | A1 | 4/2018 | Gandy et al. |
| 2018/0116741 | A1 | 5/2018 | Garcia Kilroy et al. |
| 2018/0117417 | A1 | 5/2018 | Davis |
| 2018/0130555 | A1 | 5/2018 | Chronis et al. |
| 2018/0133551 | A1 | 5/2018 | Chang |
| 2018/0140927 | A1 | 5/2018 | Kito |
| 2018/0146870 | A1 | 5/2018 | Shemesh |
| 2018/0169476 | A1 | 6/2018 | Shimada et al. |
| 2018/0177612 | A1 | 6/2018 | Trabish et al. |
| 2018/0178061 | A1 | 6/2018 | O'larte et al. |
| 2018/0199855 | A1 | 7/2018 | Odame et al. |
| 2018/0200577 | A1 | 7/2018 | Dugan |
| 2018/0214729 | A1 | 8/2018 | Rubin |
| 2018/0220935 | A1 | 8/2018 | Tadano et al. |
| 2018/0228682 | A1 | 8/2018 | Bayerlein et al. |
| 2018/0232492 | A1 | 8/2018 | Al-Alul et al. |
| 2018/0236307 | A1 | 8/2018 | Hyde et al. |
| 2018/0240552 | A1 | 8/2018 | Tuyl et al. |
| 2018/0250075 | A1 | 9/2018 | Cho |
| 2018/0253991 | A1 | 9/2018 | Tang et al. |
| 2018/0255110 | A1 | 9/2018 | Dowlatkhah et al. |
| 2018/0256079 | A1 | 9/2018 | Yang et al. |
| 2018/0256939 | A1 | 9/2018 | Malcolm |
| 2018/0263530 | A1 | 9/2018 | Jung |
| 2018/0263535 | A1 | 9/2018 | Cramer |
| 2018/0263552 | A1 | 9/2018 | Graman et al. |
| 2018/0264312 | A1 | 9/2018 | Pompile et al. |
| 2018/0271432 | A1 | 9/2018 | Auchinleck et al. |
| 2018/0272184 | A1 | 9/2018 | Vassilaros et al. |
| 2018/0272190 | A1 | 9/2018 | Miura |
| 2018/0280784 | A1 | 10/2018 | Romeo et al. |
| 2018/0285463 | A1 | 10/2018 | Choi et al. |
| 2018/0290017 | A1 | 10/2018 | Fung |
| 2018/0296143 | A1 | 10/2018 | Anderson et al. |
| 2018/0296157 | A1 | 10/2018 | Bleich et al. |
| 2018/0318122 | A1 | 11/2018 | LeCursi et al. |
| 2018/0326243 | A1 | 11/2018 | Badi et al. |
| 2018/0330058 | A1 | 11/2018 | Bates |
| 2018/0330810 | A1 | 11/2018 | Gamarnik |
| 2018/0330824 | A1 | 11/2018 | Athey et al. |
| 2018/0348759 | A1 | 12/2018 | Freeman |
| 2018/0353812 | A1 | 12/2018 | Lannon et al. |

(56) References Cited

U.S. PATENT DOCUMENTS

2018/0358119 A1 12/2018 Bhushan
2018/0360340 A1 12/2018 Rehse et al.
2018/0361203 A1 12/2018 Wang
2018/0366225 A1 12/2018 Mansi et al.
2018/0373844 A1 12/2018 Ferrandez-Escamez et al.
2019/0005195 A1 1/2019 Peterson
2019/0009135 A1 1/2019 Wu
2019/0009136 A1 1/2019 Lee
2019/0019163 A1 1/2019 Batey et al.
2019/0019573 A1 1/2019 Lake et al.
2019/0019578 A1 1/2019 Vaccaro
2019/0025995 A1 1/2019 Williams
2019/0030415 A1 1/2019 Volpe, Jr.
2019/0031284 A1 1/2019 Fuchs
2019/0046794 A1 2/2019 Goodall et al.
2019/0060708 A1 2/2019 Fung
2019/0065970 A1 2/2019 Bonutti et al.
2019/0066832 A1 2/2019 Kang et al.
2019/0076701 A1 3/2019 Dugan
2019/0080802 A1 3/2019 Ziobro et al.
2019/0083846 A1 3/2019 Eder
2019/0088356 A1 3/2019 Oliver et al.
2019/0090744 A1 3/2019 Mahfouz
2019/0096534 A1 3/2019 Joao
2019/0105551 A1 4/2019 Ray
2019/0108912 A1 4/2019 Spurlock, III
2019/0111299 A1 4/2019 Radcliffe et al.
2019/0115097 A1 4/2019 Macoviak et al.
2019/0117156 A1 4/2019 Howard et al.
2019/0118038 A1 4/2019 Tana et al.
2019/0118066 A1 4/2019 Cardona
2019/0122770 A1 4/2019 Pengetnze
2019/0126099 A1 5/2019 Hoang
2019/0132948 A1 5/2019 Longinotti-Buitoni et al.
2019/0134308 A1 5/2019 Newberry
2019/0134454 A1 5/2019 Mahoney et al.
2019/0137988 A1 5/2019 Cella et al.
2019/0143191 A1 5/2019 Ran et al.
2019/0143193 A1 5/2019 Kim
2019/0145774 A1 5/2019 Ellis
2019/0146740 A1 5/2019 Yuen
2019/0163876 A1 5/2019 Remme et al.
2019/0167988 A1 6/2019 Shahriari et al.
2019/0172587 A1 6/2019 Park et al.
2019/0175988 A1 6/2019 Volterrani et al.
2019/0183715 A1 6/2019 Kapure et al.
2019/0192880 A1 6/2019 Hibbard
2019/0200920 A1 7/2019 Tien et al.
2019/0209022 A1 7/2019 Sobol
2019/0209891 A1 7/2019 Fung
2019/0214119 A1 7/2019 Wachira et al.
2019/0223797 A1 7/2019 Tran
2019/0224528 A1 7/2019 Omid-Zohoor et al.
2019/0228856 A1 7/2019 Leifer
2019/0232108 A1 8/2019 Kovach et al.
2019/0240103 A1 8/2019 Hepler et al.
2019/0240541 A1 8/2019 Denton et al.
2019/0244540 A1 8/2019 Errante et al.
2019/0247718 A1 8/2019 Blevins
2019/0251456 A1 8/2019 Constantin
2019/0251723 A1 8/2019 Coppersmith
2019/0261959 A1 8/2019 Frankel
2019/0262084 A1 8/2019 Roh
2019/0269343 A1 9/2019 Ramos Murguialday et al.
2019/0274523 A1 9/2019 Bates et al.
2019/0275368 A1 9/2019 Maroldi
2019/0283247 A1 9/2019 Chang
2019/0290191 A1 9/2019 Leppäluoto et al.
2019/0304584 A1 10/2019 Savolainen
2019/0307983 A1 10/2019 Goldman
2019/0314681 A1 10/2019 Yang
2019/0344123 A1 11/2019 Rubin et al.
2019/0354632 A1 11/2019 Mital et al.
2019/0362242 A1 11/2019 Pillai et al.
2019/0366146 A1 12/2019 Tong et al.
2019/0371472 A1 12/2019 Blanchard
2019/0385199 A1 12/2019 Bender et al.
2019/0388728 A1 12/2019 Wang et al.
2019/0392936 A1 12/2019 Arric et al.
2019/0392939 A1 12/2019 Basta et al.
2020/0005928 A1 1/2020 Daniel
2020/0015736 A1 1/2020 Alhathal
2020/0034665 A1 1/2020 Ghanta
2020/0034707 A1 1/2020 Kivatinos et al.
2020/0038703 A1 2/2020 Cleary et al.
2020/0051446 A1 2/2020 Rubinstein et al.
2020/0054922 A1 2/2020 Azaria
2020/0066390 A1 2/2020 Svendrys et al.
2020/0085300 A1 3/2020 Kwatra et al.
2020/0090802 A1 3/2020 Maron
2020/0093418 A1 3/2020 Kluger et al.
2020/0098463 A1 3/2020 Arunachalam et al.
2020/0121987 A1 4/2020 Loh
2020/0129237 A1 4/2020 Erdem
2020/0129808 A1 4/2020 Fomin
2020/0139194 A1 5/2020 Min
2020/0143922 A1 5/2020 Chekroud et al.
2020/0151595 A1 5/2020 Jayalath et al.
2020/0151646 A1 5/2020 De La Fuente Sanchez
2020/0152339 A1 5/2020 Pulitzer et al.
2020/0160044 A1 5/2020 Sur
2020/0160198 A1 5/2020 Reeves et al.
2020/0170876 A1 6/2020 Kapure et al.
2020/0176098 A1 6/2020 Lucas et al.
2020/0188774 A1 6/2020 Fung
2020/0197744 A1 6/2020 Schweighofer
2020/0221975 A1 7/2020 Basta et al.
2020/0237291 A1 7/2020 Raja
2020/0237452 A1 7/2020 Wolf et al.
2020/0254310 A1 8/2020 Triplett
2020/0261763 A1 8/2020 Park
2020/0267487 A1 8/2020 Siva
2020/0275886 A1 9/2020 Mason
2020/0289045 A1 9/2020 Hacking et al.
2020/0289046 A1 9/2020 Hacking et al.
2020/0289879 A1 9/2020 Hacking et al.
2020/0289880 A1 9/2020 Hacking et al.
2020/0289881 A1 9/2020 Hacking et al.
2020/0289889 A1 9/2020 Hacking et al.
2020/0293712 A1 9/2020 Potts et al.
2020/0303063 A1 9/2020 Sharma et al.
2020/0312447 A1 10/2020 Bohn et al.
2020/0320454 A1 10/2020 Almashor
2020/0334972 A1 10/2020 Gopalakrishnan
2020/0338394 A1 10/2020 Neumann
2020/0346072 A1 11/2020 Shah
2020/0350076 A1 11/2020 Brown
2020/0353314 A1 11/2020 Messinger
2020/0357299 A1 11/2020 Patel et al.
2020/0365256 A1 11/2020 Hayashitani et al.
2020/0376327 A1 12/2020 Bissonnette
2020/0391080 A1 12/2020 Powers
2020/0395112 A1 12/2020 Ronner
2020/0398083 A1 12/2020 Adelsheim
2020/0401224 A1 12/2020 Cotton
2020/0402638 A1 12/2020 Song et al.
2020/0402662 A1 12/2020 Esmailian et al.
2020/0410374 A1 12/2020 White
2020/0410385 A1 12/2020 Otsuki
2020/0410893 A1 12/2020 Ridington
2020/0411162 A1 12/2020 Lien et al.
2020/0411170 A1 12/2020 Brown
2021/0005224 A1 1/2021 Rothschild et al.
2021/0005319 A1 1/2021 Otsuki et al.
2021/0008413 A1 1/2021 Asikainen et al.
2021/0015560 A1 1/2021 Boddington et al.
2021/0027889 A1 1/2021 Neil et al.
2021/0035674 A1 2/2021 Volosin et al.
2021/0050086 A1 2/2021 Rose et al.
2021/0065855 A1 3/2021 Pepin et al.
2021/0074178 A1 3/2021 Ilan et al.
2021/0076981 A1 3/2021 Hacking et al.
2021/0077860 A1 3/2021 Posnack et al.
2021/0077884 A1 3/2021 De Las Casas Zolezzi et al.

(56) References Cited

U.S. PATENT DOCUMENTS

2021/0082554 A1 3/2021 Kalia et al.
2021/0093891 A1 4/2021 Sheng
2021/0098099 A1 4/2021 Neumann
2021/0098129 A1 4/2021 Neumann
2021/0101051 A1 4/2021 Posnack et al.
2021/0106899 A1 4/2021 Willardson
2021/0113890 A1 4/2021 Posnack et al.
2021/0125696 A1 4/2021 Liu et al.
2021/0127974 A1 5/2021 Mason et al.
2021/0128080 A1 5/2021 Mason et al.
2021/0128255 A1 5/2021 Mason et al.
2021/0128978 A1 5/2021 Gilstrom et al.
2021/0134412 A1 5/2021 Guaneri et al.
2021/0134425 A1 5/2021 Mason et al.
2021/0134427 A1 5/2021 Mason et al.
2021/0134428 A1 5/2021 Mason et al.
2021/0134429 A1 5/2021 Mason
2021/0134430 A1 5/2021 Mason et al.
2021/0134432 A1 5/2021 Mason et al.
2021/0134456 A1 5/2021 Posnack et al.
2021/0134457 A1 5/2021 Mason et al.
2021/0134458 A1 5/2021 Mason et al.
2021/0134463 A1 5/2021 Mason et al.
2021/0138304 A1 5/2021 Mason et al.
2021/0142875 A1 5/2021 Mason et al.
2021/0142893 A1 5/2021 Guaneri et al.
2021/0142898 A1 5/2021 Mason et al.
2021/0142903 A1 5/2021 Mason et al.
2021/0144074 A1 5/2021 Guaneri et al.
2021/0186419 A1 6/2021 Van Ee et al.
2021/0187348 A1 6/2021 Phillips et al.
2021/0202090 A1 7/2021 ODonovan et al.
2021/0202103 A1 7/2021 Bostic et al.
2021/0205660 A1 7/2021 Shavit
2021/0217516 A1 7/2021 Nash
2021/0236020 A1 8/2021 Matijevich et al.
2021/0236903 A1 8/2021 Briel
2021/0240853 A1 8/2021 Carlson
2021/0241137 A1 8/2021 Jain et al.
2021/0244998 A1 8/2021 Hacking et al.
2021/0245003 A1 8/2021 Turner
2021/0251562 A1 8/2021 Jain
2021/0272677 A1 9/2021 Barbee
2021/0275025 A1 9/2021 Hickle
2021/0291010 A1 9/2021 Miller
2021/0338469 A1 11/2021 Dempers
2021/0343384 A1 11/2021 Purushothaman et al.
2021/0345879 A1 11/2021 Mason et al.
2021/0345975 A1 11/2021 Mason et al.
2021/0350888 A1 11/2021 Guaneri et al.
2021/0350898 A1 11/2021 Mason et al.
2021/0350899 A1 11/2021 Mason et al.
2021/0350901 A1 11/2021 Mason et al.
2021/0350902 A1 11/2021 Mason et al.
2021/0350914 A1 11/2021 Guaneri et al.
2021/0350926 A1 11/2021 Mason et al.
2021/0354002 A1 11/2021 Schaefer
2021/0361514 A1 11/2021 Choi et al.
2021/0366587 A1 11/2021 Mason et al.
2021/0369536 A1 12/2021 Mooney
2021/0375425 A1 12/2021 Zhang
2021/0383008 A1 12/2021 Manasse
2021/0383909 A1 12/2021 Mason et al.
2021/0387054 A1 12/2021 Schaefer
2021/0391091 A1 12/2021 Mason
2021/0394011 A1 12/2021 Neuhaus et al.
2021/0398668 A1 12/2021 Chock et al.
2021/0406738 A1 12/2021 O'Donncha et al.
2021/0407670 A1 12/2021 Mason et al.
2021/0407681 A1 12/2021 Mason et al.
2022/0000556 A1 1/2022 Casey et al.
2022/0015838 A1 1/2022 Posnack et al.
2022/0016480 A1 1/2022 Bissonnette et al.
2022/0016482 A1 1/2022 Bissonnette
2022/0016484 A1* 1/2022 Bissonnette ....... A63B 23/0417
2022/0016485 A1 1/2022 Bissonnette et al.
2022/0016486 A1 1/2022 Bissonnette
2022/0020469 A1 1/2022 Tanner
2022/0028511 A1 1/2022 Neumann
2022/0044806 A1 2/2022 Sanders et al.
2022/0047921 A1 2/2022 Bissonnette et al.
2022/0066548 A1 3/2022 Helot
2022/0079690 A1 3/2022 Mason et al.
2022/0080256 A1 3/2022 Arn et al.
2022/0080265 A1 3/2022 Watterson
2022/0096006 A1 3/2022 Wu et al.
2022/0105384 A1 4/2022 Hacking et al.
2022/0105385 A1 4/2022 Hacking et al.
2022/0105390 A1 4/2022 Yuasa
2022/0115133 A1 4/2022 Mason et al.
2022/0117514 A1 4/2022 Kuhn et al.
2022/0118218 A1 4/2022 Bense et al.
2022/0122724 A1 4/2022 Durlach et al.
2022/0126169 A1 4/2022 Mason
2022/0133576 A1 5/2022 Choi et al.
2022/0148725 A1 5/2022 Mason et al.
2022/0158916 A1 5/2022 Mason et al.
2022/0165398 A1 5/2022 Avila-Hernandez et al.
2022/0176039 A1 6/2022 Lintereur et al.
2022/0181004 A1 6/2022 Zilca et al.
2022/0193491 A1 6/2022 Mason et al.
2022/0230729 A1 7/2022 Mason et al.
2022/0238222 A1 7/2022 Neuberg
2022/0238223 A1 7/2022 Mason et al.
2022/0258935 A1 8/2022 Kraft
2022/0262483 A1 8/2022 Rosenberg et al.
2022/0262504 A1 8/2022 Bratty et al.
2022/0266094 A1 8/2022 Mason et al.
2022/0270738 A1 8/2022 Mason et al.
2022/0273985 A1 9/2022 Jeong et al.
2022/0273986 A1 9/2022 Mason
2022/0288460 A1 9/2022 Mason
2022/0288461 A1 9/2022 Ashley et al.
2022/0288462 A1 9/2022 Ashley et al.
2022/0293257 A1 9/2022 Guaneri et al.
2022/0300787 A1 9/2022 Wall et al.
2022/0304881 A1 9/2022 Choi et al.
2022/0304882 A1 9/2022 Choi
2022/0305291 A1 9/2022 Hibbard
2022/0305328 A1 9/2022 Choi et al.
2022/0314072 A1 10/2022 Bissonnette et al.
2022/0314074 A1 10/2022 Bissonnette
2022/0314075 A1 10/2022 Mason et al.
2022/0323826 A1 10/2022 Khurana
2022/0327714 A1 10/2022 Cook et al.
2022/0327807 A1 10/2022 Cook et al.
2022/0328181 A1 10/2022 Mason et al.
2022/0330823 A1 10/2022 Janssen
2022/0331663 A1 10/2022 Mason
2022/0336077 A1 10/2022 Chen et al.
2022/0338761 A1 10/2022 Maddahi et al.
2022/0339052 A1 10/2022 Kim
2022/0339501 A1 10/2022 Mason et al.
2022/0342969 A1 10/2022 Watterson et al.
2022/0346703 A1 11/2022 Abdo et al.
2022/0370851 A1 11/2022 Guidarelli et al.
2022/0384010 A1 12/2022 Kanayama
2022/0384012 A1 12/2022 Mason
2022/0392591 A1 12/2022 Guaneri et al.
2022/0395232 A1 12/2022 Locke
2022/0401783 A1 12/2022 Choi
2022/0415469 A1 12/2022 Mason
2022/0415471 A1 12/2022 Mason
2023/0001268 A1 1/2023 Bissonnette et al.
2023/0013530 A1 1/2023 Mason
2023/0014598 A1 1/2023 Mason et al.
2023/0022981 A1 1/2023 Bhushan
2023/0029639 A1 2/2023 Roy
2023/0047253 A1 2/2023 Gnanasambandam et al.
2023/0048040 A1 2/2023 Hacking et al.
2023/0051751 A1 2/2023 Hacking et al.
2023/0055078 A1 2/2023 Malcolm
2023/0058605 A1 2/2023 Mason
2023/0060039 A1 2/2023 Mason

(56) References Cited

U.S. PATENT DOCUMENTS

| | | | |
|---|---|---|---|
| 2023/0072368 | A1 | 3/2023 | Mason |
| 2023/0078793 | A1 | 3/2023 | Mason |
| 2023/0119461 | A1 | 4/2023 | Mason |
| 2023/0190100 | A1 | 6/2023 | Stump |
| 2023/0197240 | A1 | 6/2023 | Rosenberg |
| 2023/0201656 | A1 | 6/2023 | Hacking et al. |
| 2023/0207097 | A1 | 6/2023 | Mason |
| 2023/0207124 | A1 | 6/2023 | Walsh et al. |
| 2023/0215539 | A1 | 7/2023 | Rosenberg et al. |
| 2023/0215552 | A1 | 7/2023 | Khotilovich et al. |
| 2023/0218950 | A1 | 7/2023 | Belson et al. |
| 2023/0245747 | A1 | 8/2023 | Rosenberg et al. |
| 2023/0245748 | A1 | 8/2023 | Rosenberg et al. |
| 2023/0245750 | A1 | 8/2023 | Rosenberg et al. |
| 2023/0245751 | A1 | 8/2023 | Rosenberg et al. |
| 2023/0249599 | A1 | 8/2023 | Nicola |
| 2023/0253089 | A1 | 8/2023 | Rosenberg et al. |
| 2023/0255555 | A1 | 8/2023 | Sundaram et al. |
| 2023/0263428 | A1 | 8/2023 | Hull et al. |
| 2023/0274813 | A1 | 8/2023 | Rosenberg et al. |
| 2023/0282329 | A1 | 9/2023 | Mason et al. |
| 2023/0298718 | A1 | 9/2023 | Robinson |
| 2023/0356025 | A1 | 11/2023 | Rosenberg |
| 2023/0364471 | A1 | 11/2023 | Choi et al. |
| 2023/0364472 | A1 | 11/2023 | Posnack |
| 2023/0368886 | A1 | 11/2023 | Rosenberg |
| 2023/0377710 | A1 | 11/2023 | Chen et al. |
| 2023/0377711 | A1 | 11/2023 | Rosenberg |
| 2023/0377712 | A1 | 11/2023 | Rosenberg |
| 2023/0386639 | A1 | 11/2023 | Rosenberg |
| 2023/0390627 | A1 | 12/2023 | Bolton |
| 2023/0395231 | A1 | 12/2023 | Rosenberg |
| 2023/0395232 | A1 | 12/2023 | Rosenberg |
| 2024/0024731 | A1 | 1/2024 | Rosenberg |
| 2024/0029856 | A1 | 1/2024 | Rosenberg |
| 2024/0058651 | A1 | 2/2024 | Bissonnette |
| 2024/0127924 | A1 | 4/2024 | Rosenberg |
| 2024/0136041 | A1 | 4/2024 | Rosenberg |
| 2024/0177846 | A1 | 5/2024 | Gnanasambandam |
| 2024/0203580 | A1 | 6/2024 | Mason |
| 2024/0339192 | A1 | 10/2024 | Rosenberg |

FOREIGN PATENT DOCUMENTS

| | | | |
|---|---|---|---|
| CN | 101964151 | A | 2/2011 |
| CN | 201889024 | U | 7/2011 |
| CN | 202220794 | U | 5/2012 |
| CN | 102670381 | A | 9/2012 |
| CN | 103263336 | A | 8/2013 |
| CN | 103390357 | A | 11/2013 |
| CN | 103473631 | A | 12/2013 |
| CN | 103488880 | A | 1/2014 |
| CN | 103501328 | A | 1/2014 |
| CN | 103721343 | A | 4/2014 |
| CN | 203677851 | U | 7/2014 |
| CN | 104335211 | A | 2/2015 |
| CN | 105263448 | A | 1/2016 |
| CN | 105620643 | A | 6/2016 |
| CN | 105683977 | A | 6/2016 |
| CN | 103136447 | B | 8/2016 |
| CN | 105894088 | A | 8/2016 |
| CN | 105930668 | A | 9/2016 |
| CN | 205626871 | U | 10/2016 |
| CN | 106127646 | A | 11/2016 |
| CN | 106236502 | A | 12/2016 |
| CN | 106510985 | A | 3/2017 |
| CN | 106621195 | A | 5/2017 |
| CN | 106845077 | A | 6/2017 |
| CN | 107066819 | A | 8/2017 |
| CN | 107430641 | A | 12/2017 |
| CN | 107551475 | A | 1/2018 |
| CN | 107736982 | A | 2/2018 |
| CN | 107930021 | A | 4/2018 |
| CN | 108078737 | A | 5/2018 |
| CN | 208224811 | A | 12/2018 |
| CN | 109191954 | A | 1/2019 |
| CN | 109363887 | A | 2/2019 |
| CN | 208573971 | U | 3/2019 |
| CN | 110148472 | A | 8/2019 |
| CN | 110201358 | A | 9/2019 |
| CN | 110215188 | A | 9/2019 |
| CN | 110322957 | A | 10/2019 |
| CN | 110808092 | A | 2/2020 |
| CN | 110931103 | A | 3/2020 |
| CN | 110993057 | A | 4/2020 |
| CN | 111105859 | A | 5/2020 |
| CN | 111111110 | A | 5/2020 |
| CN | 111370088 | A | 7/2020 |
| CN | 111460305 | A | 7/2020 |
| CN | 111790111 | A | 10/2020 |
| CN | 112071393 | A | 12/2020 |
| CN | 212141371 | U | 12/2020 |
| CN | 112289425 | A | 1/2021 |
| CN | 212624809 | U | 2/2021 |
| CN | 112603295 | A | 4/2021 |
| CN | 213190965 | U | 5/2021 |
| CN | 113384850 | A | 9/2021 |
| CN | 113499572 | A | 10/2021 |
| CN | 215136488 | U | 12/2021 |
| CN | 113885361 | A | 1/2022 |
| CN | 114049961 | A | 2/2022 |
| CN | 114203274 | A | 3/2022 |
| CN | 216258145 | U | 4/2022 |
| CN | 114632302 | A | 6/2022 |
| CN | 114694824 | A | 7/2022 |
| CN | 114898832 | A | 8/2022 |
| CN | 114983760 | A | 9/2022 |
| CN | 217472652 | U | 9/2022 |
| CN | 110270062 | B | 10/2022 |
| CN | 218420859 | U | 2/2023 |
| CN | 115954081 | A | 4/2023 |
| DE | 95019 | C | 1/1897 |
| DE | 7628633 | U1 | 12/1977 |
| DE | 8519150 | U1 | 10/1985 |
| DE | 3732905 | A1 | 7/1988 |
| DE | 19619820 | A1 | 12/1996 |
| DE | 29620008 | U1 | 2/1997 |
| DE | 19947926 | A1 | 4/2001 |
| DE | 102018202497 | A1 | 8/2018 |
| DE | 102018211212 | A1 | 1/2019 |
| DE | 102019108425 | B3 | 8/2020 |
| EP | 199600 | A2 | 10/1986 |
| EP | 0383137 | A2 | 8/1990 |
| EP | 634319 | A2 | 1/1995 |
| EP | 0919259 | A1 | 6/1999 |
| EP | 1034817 | A1 | 9/2000 |
| EP | 1159989 | A1 | 12/2001 |
| EP | 1391179 | A1 | 2/2004 |
| EP | 1968028 | | 9/2008 |
| EP | 2564904 | A1 | 3/2013 |
| EP | 2575064 | A1 | 4/2013 |
| EP | 1909730 | B1 | 4/2014 |
| EP | 2815242 | A4 | 12/2014 |
| EP | 2869805 | A | 5/2015 |
| EP | 2997951 | A1 | 3/2016 |
| EP | 2688472 | B1 | 4/2016 |
| EP | 3264303 | A1 | 1/2018 |
| EP | 3323473 | A1 | 5/2018 |
| EP | 3547322 | A1 | 10/2019 |
| EP | 3627514 | A1 | 3/2020 |
| EP | 3671700 | A1 | 6/2020 |
| EP | 3688537 | A1 | 8/2020 |
| EP | 3731733 | A1 | 11/2020 |
| EP | 3984508 | A1 | 4/2022 |
| EP | 3984509 | A1 | 4/2022 |
| EP | 3984510 | A1 | 4/2022 |
| EP | 3984511 | A1 | 4/2022 |
| EP | 3984512 | A1 | 4/2022 |
| EP | 3984513 | A1 | 4/2022 |
| EP | 4054699 | A1 | 9/2022 |
| EP | 4112033 | A1 | 1/2023 |
| FR | 2527541 | A2 | 12/1983 |
| FR | 3127393 | A1 | 3/2023 |
| GB | 141664 | A | 11/1920 |

(56) References Cited

FOREIGN PATENT DOCUMENTS

| | | | |
|---|---|---|---|
| GB | 2336140 | A | 10/1999 |
| GB | 2372459 | A | 8/2002 |
| GB | 2512431 | A | 10/2014 |
| GB | 2591542 | B | 3/2022 |
| IN | 201811043670 | A | 7/2018 |
| JP | 2000005339 | A | 1/2000 |
| JP | 2003225875 | A | 8/2003 |
| JP | 2005227928 | A | 8/2005 |
| JP | 2005227928 | A1 | 8/2005 |
| JP | 2009112336 | A | 5/2009 |
| JP | 2013515995 | A | 5/2013 |
| JP | 2014104139 | A | 6/2014 |
| JP | 3193662 | U | 10/2014 |
| JP | 3198173 | U | 6/2015 |
| JP | 5804063 | B2 | 11/2015 |
| JP | 2018102842 | A | 7/2018 |
| JP | 2019028647 | A | 2/2019 |
| JP | 2019134909 | A | 8/2019 |
| JP | 6573739 | B1 | 9/2019 |
| JP | 6659831 | B2 | 3/2020 |
| JP | 2020057082 | A | 4/2020 |
| JP | 6710357 | B1 | 6/2020 |
| JP | 6775757 | B1 | 10/2020 |
| JP | 2021027917 | A | 2/2021 |
| JP | 6871379 | B2 | 5/2021 |
| JP | 2022521378 | A | 4/2022 |
| JP | 3238491 | U | 7/2022 |
| JP | 7198364 | B2 | 12/2022 |
| JP | 7202474 | B2 | 1/2023 |
| JP | 7231750 | B2 | 3/2023 |
| JP | 7231751 | B2 | 3/2023 |
| JP | 7231752 | B2 | 3/2023 |
| KR | 20020009724 | A | 2/2002 |
| KR | 200276919 | Y1 | 5/2002 |
| KR | 20020065253 | A | 8/2002 |
| KR | 100582596 | B1 | 5/2006 |
| KR | 101042258 | B1 | 6/2011 |
| KR | 101258250 | B1 | 4/2013 |
| KR | 101325581 | B1 | 11/2013 |
| KR | 20140128630 | A | 11/2014 |
| KR | 20150017693 | A | 2/2015 |
| KR | 20150078191 | A | 7/2015 |
| KR | 101580071 | B1 | 12/2015 |
| KR | 101647620 | B1 | 8/2016 |
| KR | 20160093990 | A | 8/2016 |
| KR | 20170038837 | A | 4/2017 |
| KR | 20180004928 | A | 1/2018 |
| KR | 20190029175 | A | 3/2019 |
| KR | 20190056116 | A | 5/2019 |
| KR | 101988167 | B1 | 6/2019 |
| KR | 101969392 | B1 | 8/2019 |
| KR | 102055279 | B1 | 12/2019 |
| KR | 20200019548 | A | 2/2020 |
| KR | 102088333 | B1 | 3/2020 |
| KR | 20200025290 | A | 3/2020 |
| KR | 20200029180 | A | 3/2020 |
| KR | 102097190 | B1 | 4/2020 |
| KR | 102116664 | B1 | 5/2020 |
| KR | 102116968 | B1 | 5/2020 |
| KR | 20200056233 | A | 5/2020 |
| KR | 102120828 | B1 | 6/2020 |
| KR | 102121586 | B1 | 6/2020 |
| KR | 102142713 | B1 | 8/2020 |
| KR | 102162522 | B1 | 10/2020 |
| KR | 20200119665 | A | 10/2020 |
| KR | 102173553 | B1 | 11/2020 |
| KR | 102180079 | B1 | 11/2020 |
| KR | 102188766 | B1 | 12/2020 |
| KR | 102196793 | B1 | 12/2020 |
| KR | 20210006212 | A | 1/2021 |
| KR | 102224188 | B1 | 3/2021 |
| KR | 102224618 | B1 | 3/2021 |
| KR | 102246049 | B1 | 4/2021 |
| KR | 102246050 | B1 | 4/2021 |
| KR | 102246051 | B1 | 4/2021 |
| KR | 102246052 | B1 | 4/2021 |
| KR | 20210052028 | A | 5/2021 |
| KR | 102264498 | B1 | 6/2021 |
| KR | 102352602 | B1 | 1/2022 |
| KR | 102352603 | B1 | 1/2022 |
| KR | 102352604 | B1 | 1/2022 |
| KR | 20220004639 | A | 1/2022 |
| KR | 102387577 | B1 | 4/2022 |
| KR | 102421437 | B1 | 7/2022 |
| KR | 20220102207 | A | 7/2022 |
| KR | 102427545 | B1 | 8/2022 |
| KR | 102467495 | B1 | 11/2022 |
| KR | 102467496 | B1 | 11/2022 |
| KR | 102469723 | B1 | 11/2022 |
| KR | 102471990 | B1 | 11/2022 |
| KR | 20220145989 | A | 11/2022 |
| KR | 20220156134 | A | 11/2022 |
| KR | 102502744 | B1 | 2/2023 |
| KR | 20230019349 | A | 2/2023 |
| KR | 20230019350 | A | 2/2023 |
| KR | 20230026556 | A | 2/2023 |
| KR | 20230026668 | A | 2/2023 |
| KR | 20230040526 | | 3/2023 |
| KR | 20230050506 | A | 4/2023 |
| KR | 20230056118 | A | 4/2023 |
| KR | 102528503 | B1 | 5/2023 |
| KR | 102531930 | B1 | 5/2023 |
| KR | 102532766 | B1 | 5/2023 |
| KR | 102539190 | B1 | 6/2023 |
| RU | 2014131288 | A | 2/2016 |
| RU | 2607953 | C2 | 1/2017 |
| TW | M474545 | U | 3/2014 |
| TW | I442956 | B | 7/2014 |
| TW | M638437 | U | 3/2023 |
| WO | 1998009687 | A1 | 3/1998 |
| WO | 0149235 | A2 | 7/2001 |
| WO | 0151083 | A2 | 7/2001 |
| WO | 2001050387 | A1 | 7/2001 |
| WO | 2001056465 | A1 | 8/2001 |
| WO | 02062211 | A2 | 8/2002 |
| WO | 02093312 | A2 | 11/2002 |
| WO | 2003043494 | A1 | 5/2003 |
| WO | 2005018453 | A1 | 3/2005 |
| WO | 2005074369 | A2 | 8/2005 |
| WO | 2006004430 | A2 | 1/2006 |
| WO | 2006012694 | A1 | 2/2006 |
| WO | 2007102709 | A1 | 9/2007 |
| WO | 2008114291 | A1 | 9/2008 |
| WO | 2008140780 | A1 | 11/2008 |
| WO | 2009003170 | A1 | 12/2008 |
| WO | 2009008968 | A1 | 1/2009 |
| WO | 2010009278 | A2 | 1/2010 |
| WO | 2011025322 | A2 | 3/2011 |
| WO | 2012128801 | A1 | 9/2012 |
| WO | 2013002568 | A2 | 1/2013 |
| WO | 2023164292 | A1 | 3/2013 |
| WO | 2013122839 | A1 | 8/2013 |
| WO | 2014011447 | A1 | 1/2014 |
| WO | 2014163976 | A1 | 10/2014 |
| WO | 2015026744 | A1 | 2/2015 |
| WO | 2015065298 | A1 | 5/2015 |
| WO | 2015082555 | A1 | 6/2015 |
| WO | 2016151364 | A1 | 9/2016 |
| WO | 2016154318 | A1 | 9/2016 |
| WO | 2017030781 | A1 | 2/2017 |
| WO | 2017166074 | A1 | 5/2017 |
| WO | 2017091691 | A1 | 6/2017 |
| WO | 2017165238 | A1 | 9/2017 |
| WO | 2018027080 | A1 | 2/2018 |
| WO | 2018081795 | A1 | 5/2018 |
| WO | 2018171853 | A1 | 9/2018 |
| WO | 2019022706 | A1 | 1/2019 |
| WO | 2019106003 | A1 | 6/2019 |
| WO | 2019143940 | A1 | 7/2019 |
| WO | 2020014710 | A2 | 1/2020 |
| WO | 2020075190 | A1 | 4/2020 |
| WO | 2020130979 | A1 | 6/2020 |
| WO | 2020149815 | A2 | 7/2020 |
| WO | 2020229705 | A1 | 11/2020 |

(56) References Cited

FOREIGN PATENT DOCUMENTS

| | | | |
|---|---|---|---|
| WO | 2020245727 | A1 | 12/2020 |
| WO | 2020249855 | A1 | 12/2020 |
| WO | 2020252599 | A1 | 12/2020 |
| WO | 2020256577 | A1 | 12/2020 |
| WO | 2021021447 | A1 | 2/2021 |
| WO | 2021022003 | A1 | 2/2021 |
| WO | 2021038980 | A1 | 3/2021 |
| WO | 2021055427 | A1 | 3/2021 |
| WO | 2021061061 | A1 | 4/2021 |
| WO | 2021090267 | A1 | 5/2021 |
| WO | 2021138620 | A1 | 7/2021 |
| WO | 2021216881 | A1 | 10/2021 |
| WO | 2021236961 | A1 | 11/2021 |
| WO | 2022047006 | A1 | 3/2022 |
| WO | 2022092493 | A1 | 5/2022 |
| WO | 2022092494 | A1 | 5/2022 |
| WO | 2022212883 | A1 | 10/2022 |
| WO | 2022212921 | A1 | 10/2022 |
| WO | 2022216498 | A1 | 10/2022 |
| WO | 2022251420 | A1 | 12/2022 |
| WO | 2023008680 | A1 | 2/2023 |
| WO | 2023008681 | A1 | 2/2023 |
| WO | 2023022319 | A1 | 2/2023 |
| WO | 2023022320 | A1 | 2/2023 |
| WO | 2023052695 | A1 | 4/2023 |
| WO | 2023091496 | A1 | 5/2023 |
| WO | 2023215155 | A1 | 11/2023 |
| WO | 2023230075 | A1 | 11/2023 |
| WO | 2024013267 | A1 | 1/2024 |
| WO | 2024107807 | A1 | 5/2024 |

OTHER PUBLICATIONS

Davenport et al., "The Potential for Artificial Intelligence in Healthcare," Future Healthcare Journal, 2019, pp. 94-98, vol. 6, No. 2.

Jeong et al., "Remotely controlled biking is associated with improved adherence to prescribed cycling speed," Technology and Health Care 23, 2015, 7 pages.

Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.

Blasiak et al., "curate.ai: Optimizing Personalized Medicine with Artificial Intelligence," Slas Technology: Translating Life Sciences Innovation, 2020, 11 pages.

Amiya et al., "Is Exercise Training Appropriate for Patients With Advanced Heart Failure Receiving Continuous Inotropic Infusion? A Review," 2018, pp. 1-9, vol. 12, Japan.

Chu Hin Yee, "Physical Activity, Sedentary Behaviour and Health: From Measurements to Recommendations," 2018, 255 pages.

Marios et al., "The effect of tele-monitoring on exercise training adherence, functional capacity, quality of life and glycemic control in patients with type II diabetes," Journal of Sports Science and Medicine, Mar. 2012, vol. 11, 6 pages.

"Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12: 1-19. Springer Nature B.V. (Dec. 2017) (Year: 2017)".

Fuller, Carole G.; Diagnosis and treatment considerations with comorbid developmentally disabled populations; Journal of Clinical Psychology 54.1: 1-10. John Wiley and Sons Inc. (Jan. 1998) (Year: 1998).

He, Jianxing et al. The practical implementation of artificial intelligence technologies in medicine. Nature Medicine; New York vol. 25, Iss. 1. Jan. 2019. (Year: 2019).

CG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC.2013.2262913. (Year: 2013).

H. Demirkan, "A Smart Healthcare Systems Framework," in IT Professional, vol. 15, No. 5, pp. 38-45, Sep.-Oct. 2013, doi: 10.1109/MITP.2013.35. (Year: 2013).

W. Rashwan, J. Fowler and A. Arisha, "A Multi-Method Scheduling Framework for Medical Staff," 2018 Winter Simulation Conference (WSC), Gothenburg, Sweden, 2018, pp. 1464-1475, doi: 10.1109/WSC.2018.8632247. (Year: 2018).

Shen et al, "Intelligent inverse treatment planning via deep reinforcement learning, a proof-of-principle study in high dose-rate brachytherapy for cervical cancer," pp. 1-17, May 29, 2019, Phys. Med. Biol. vol. 64, No. 115013.

Fraass et al, "The impact of treatment complexity and computer-control delivery technology on treatment delivery errors," pp. 651-659, Oct. 1, 1998, International Journal of Radiation Oncology Biology Physics, vol. 42, Issue 3, https://doi.org/:10.1016/s0360-3016(98)00244-2. PMID: 9806527.

Marchal-Crespo et al, "Review of control strategies for robotic movement training after neurologic injury," pp. 1-15, Jun. 16, 2009, Journal of NeuroEngineering and Rehabilitation, vol. 6, No. 20, https://doi.org/10.1186/1743-0003-6-20.

Karboub et al, "A Machine Learning Based Discharge Prediction of Cardiovascular Diseases Patients in Intensive Care Units.," pp. 1-23, May 24, 2022, Healthcare (Basel, Switzerland) MDPI, vol. 10(6), No. 966, https://doi.org/10.3390/healthcare10060966.

Chrif et al, "Control design for a lower-limb paediatric therapy device using linear motor technology," pp. 119-127, Jun. 9, 2017, Biomedical Usignal Processing and Control, vol. 38, https://www.sciencedirect.com/science/article/pii/S1746809417301027.

International Preliminary Report on Patentability of International Application No. PCT/2024/022550, Date of Mailing Sep. 20, 2025, 7 pages.

Joudaki et. al., "Using Data Mining to Detect Health Care Fraud and Abuse: A Review of Literature", Global Journal of Health Science, vol. 7, No. 1, 2015 (Year: 2015).

Lown, et al. "Machine Learning Detection of Atrial Fibrillation Using Wearable Technology," Jan. 24, 2020; https://doi.org/10.1371/journal.pen.0227401 (year 2020).

Dzierzanowski et al. 1985, "Gaitspert: An Expert System for the Evaluation of Abnormal Human Locomotion Arising from Stroke," in IEEE Transactions on Biomedical Engineering, vol. BME-32, No. 11, pp. 935-942, Nov. 1985, doi: 10.1109/TBME.1985.325626.

Ona et al. 2018, "Review of Robotics in Neurorehabilitation: Towards an Automated Process for Upper Limb," J Healthc Eng. Apr. 1, 2018;2018:9758939. doi: 10.1155/2018/9758939. PMID: 29707189; PMCID: PMC5901488.

Treadmill Reviews, "All About Using iFit with your Treadmill", (Jul. 9, 2019) (Year: 2019).

Nissim N, Boland MR, Tatonetti NP, Elovici Y, Hripcsak G, Shahar Y, Moskovitch R. Improving condition severity classification with an efficient active learning based framework. J Biomed Inform. Jun. 2016;61 :44-54. doi: 10.1016/j.jbi.2016.03.016. Epub Mar. 22, 2016. PMID: 27016383; PMCID: PMC5486916. (Year: 2016).

Jennie Dusheck, "Wearable sensors can tell when you are getting sick", (Jan. 12, 2017) (Year: 2017).

Anton et al., "A Telerehabilitation System for the Selection, Evaluation and Remote Management of Therapies," Sensors, vol. 18, No. 5, Article 1459 (2018)) (Year: 2018).

Jeong et al., "Computer-assisted upper extremity training using interactive biking exercise (iBikE) platform," Sep. 2012, pp. 1-5, 34th Annual International Conference of the IEEE EMBS.

Gerbild et al., "Physical Activity to Improve Erectile Dysfunction: A Systematic Review of Intervention Studies," Sexual Medicine, 2018, 15 pages.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily

(56) References Cited

OTHER PUBLICATIONS

Living for Telemedical Assessment of Cardiovascular Risk," Article, 2018, 17 pages, Sensors, Poland.
Warburton et al., "International Launch of the Par-•Q+ and ePARmed-•X+ Validation of the PAR-•Q+ and ePARmed••X+," Health & Fitness Journal of Canada, 2011, 9 pages, vol. 4, No. 2.
Barrett et al., "Artificial intelligence supported patient self-care in chronic heart failure: a paradigm shift from reactive to predictive, preventive and personalised care," EPMA Journal (2019), pp. 445-464.
Derkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.
Thomas et al., "Home-Based Cardiac Rehabilitation," Circulation, 2019, pp. e69-e89, vol. 140.
Thomas et al., "Home-Based Cardiac Rehabilitation," Journal of the American College of Cardiology, Nov. 1, 2019, pp. 133-153, vol. 74.
Thomas et al., "Home-Based Cardiac Rehabilitation," HHS Public Access, Oct. 2, 2020, pp. 1-39.
Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.
Chen et al., "Home-based cardiac rehabilitation improves quality of life, aerobic capacity, and readmission rates in patients with chronic heart failure," Medicine, 2018, pp. 1-5 vol. 97:4.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.
Beene et al., "AI and Care Delivery: Emerging Opportunities for Artificial Intelligence to Transform How Care Is Delivered," Nov. 2019, American Hospital Association, pp. 1-12.
Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health Networking, Applications and Services, Columbia, MO, USA, 2011, 6 pages.
Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.
Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.
Zakari et al., "Are There Limitations to Exercise Benefits in Peripheral Arterial Disease?," Frontiers in Cardiovascular Medicine, Nov. 2018, vol. 5, Article 173, 12 pages.
You et al., "Including Blood Vasculature into a Game-Theoretic Model of Cancer Dynamics," Games 2019, 10, 13, 22 pages.
Jeong et al., "Computer-assisted upper extremity training using interactive biking exercise (iBikE) platform," Sep. 2012, 34th Annual International Conference of the IEEE EMBS, 5 pages.
Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.
Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.
Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.
Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.
Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.
Davenport et al., "The Potential for Artificial Intelligence in Healthcare", 2019, Future Healthcare Journal 2019, vol. 6, No. 2: Year: 2019, pp. 1-5.
Ahmed et al., "Artificial Intelligence With Multi-Functional Machine Learning Platform Development for Better Healthcare and Precision Medicine", 2020, Database (Oxford), 2020:baaa010. doi: 10.1093/database/baaa010 (Year: 2020), pp. 1-35.
Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.
De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.
Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.
Yin Chieh et al., "A Virtual Reality-Cycling Training System for Lower Limb Balance Improvement", BioMed Research International, vol. 2016, pp. 1-10.
Capecci et al. 2016, "Physical rehabilitation exercises assessment based on Hidden Semi-Marlkov Model by Kinect v2," 2016 IEEE-EMBS International Conference on Biomedical and Health Informatics (BHI), Las Vegas, NV, USA, 2016, pp. 256-259, doi: 10.1109/BH 1.2016. 7 455883.
Cespedes et al. 2020, "Social Human-Robot Interaction for Gait Rehabilitation," in IEEE Transactions on Neural Systems and Rehabilitation Engineering, vol. 28, No. 6, pp. 1299-1307, Jun. 2020, doi: 10.1109/TNSRE.2020.2987428.
Jamil, Faisal, et al. "Towards secure fitness framework based on IoT-enabled blockchain network integrated with machine learning algorithms." Sensors 21.5 (2021): 1640. (Year: 2021).
International Search Report and Written Opinion for PCT/US2023/014137, dated Jun. 9, 2023, 13 pages.
Website for "Esino 2022 Physical Therapy Equipments Arm Fitness Indoor Trainer Leg Spin Cycle Machine Exercise Bike for Elderly,"

(56) References Cited

OTHER PUBLICATIONS https://www.made-in-china.com/showroom/esinogroup/product-detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform for Personalized Predictive Analytics", ProQuest LLC, Jul. 2017, 185 pages.
Website for "Pedal Exerciser", p. 1, retrieved on Sep. 9, 2022 from https://www.vivehealth.com/collections/physical-therapy-equipment/products/pedalexerciser.
Website for "Functional Knee Brace with ROM", p. 1, retrieved on Sep. 9, 2022 from http://medicalbrace.gr/en/product/functional-knee-brace-with-goniometer-mbtelescopicknee/.
Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.
International Searching Authority, International Preliminary Report on Patentability of International Application No. PCT/US2017/50895, Date of Mailing Dec. 11, 2018, 52 pages.
International Searching Authority, Search Report and Written Opinion for International Application No. PCT/US2017/50895, Date of Mailing Jan. 12, 2018, 6 pages.
International Searching Authority, Search Report and Written Opinion for International Application No. PCT/US2020/021876, Date of Mailing May 28, 2020, 8 pages.
International Searching Authority, Search Report and Written Opinion for International Application No. PCT/US2020/051008, Date of Mailing Dec. 10, 2020, 9 pages.
International Searching Authority, Search Report and Written Opinion for International Application No. PCT/US2020/056661, Date of Mailing Feb. 12, 2021, 12 pages.
International Searching Authority, Search Report and Written Opinion for International Application No. PCT/US2021/032807, Date of Mailing Sep. 6, 2021, 11 pages.
Matrix, R3xm Recumbent Cycle, retrieved on Aug. 4, 2020, 7 pages, https://www.matrixfitness.com/en/cardio/cycles/r3xm-recumbent.
ROM3 Rehab, ROM3 Rehab System, Apr. 20, 2015, retrieved on Aug. 31, 2018, 12 pages, https://vimeo.com/125438463.

* cited by examiner

METHOD AND SYSTEM FOR USING SENSOR DATA TO DETECT JOINT MISALIGNMENT OF A USER USING A TREATMENT DEVICE TO PERFORM A TREATMENT PLAN

CROSS-REFERENCES TO RELATED APPLICATIONS

This application is a continuation-in-part of U.S. patent application Ser. No. 17/736,891, filed May 4, 2022, titled "Systems and Methods for Using Artificial Intelligence to Implement a Cardio Protocol via Relay-Based System," which is a continuation-in-part of U.S. patent application Ser. No. 17/379,542, filed Jul. 19, 2021, now U.S. Pat. No. 11,328,807, titled "System and Method for Using Artificial Intelligence in Telemedicine-Enabled Hardware to Optimize Rehabilitative Routines Capable of Enabling Remote Rehabilitative Compliance," which is a continuation of U.S. patent application Ser. No. 17/146,705, filed Jan. 12, 2021, titled "System and Method for Using Artificial Intelligence in Telemedicine-Enabled Hardware to Optimize Rehabilitative Routines Capable of Enabling Remote Rehabilitative Compliance," which is a continuation-in-part of U.S. patent application Ser. No. 17/021,895, filed Sep. 15, 2020, now U.S. Pat. No. 11,071,597, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes.

The application U.S. patent application Ser. No. 17/146,705 also claims priority to and the benefit of U.S. Provisional Patent Application Ser. No. 63/113,484, filed Nov. 13, 2020, titled "System and Method for Use of Artificial Intelligence in Telemedicine-Enabled Hardware to Optimize Rehabilitative Routines for Enabling Remote Rehabilitative Compliance," the entire disclosures of which are hereby incorporated by reference for all purposes.

This application also claims the benefit of U.S. Patent Application Ser. No. 63/240,636, filed Sep. 3, 2021, titled "Method and System for Using a Sensor Data to Detect Joint Misalignment of a User using a Treatment Device To Perform A Treatment Plan," the entire disclosure of which is hereby incorporated by reference for all purposes.

BACKGROUND

Remote medical assistance, also referred to, inter alia, as remote medicine, telemedicine, telemed, telmed, tel-med, or telehealth, is an at least two-way communication between a healthcare professional or providers, such as a physician or a physical therapist, and a patient using audio and/or audiovisual and/or other sensorial or perceptive (e.g., tactile, gustatory, haptic, pressure-sensing-based or electromagnetic (e.g., neurostimulation) communications (e.g., via a computer, a smartphone, or a tablet).

SUMMARY

Another aspect of the disclosed embodiments includes a method that includes receiving treatment data associated with a user capable of using a treatment device to perform a treatment plan. The treatment data comprises at least one of characteristics of the user, treatment measurement information associated with the user while the user uses the treatment device, one or more characteristics of the treatment device, and at least one aspect of the treatment plan. The method also includes receiving user-related data (URD) associated with the user and, while the user engages in at least one activity, receiving alignment data associated with the user. The method also includes identifying, based on at least the treatment data, the URD, and the alignment data, at least one alignment characteristic associated with the user and modifying at least one aspect of the treatment plan in response to receiving, from a healthcare professional, treatment plan input that includes at least one modification to the at least one aspect of the treatment plan.

Another aspect of the disclosed embodiments includes a system that includes a processing device and a memory communicatively coupled to the processing device and capable of storing instructions. The processing device executes the instructions to perform any of the methods, operations, or steps described herein.

Another aspect of the disclosed embodiments includes a tangible, non-transitory computer-readable medium storing instructions that, when executed, cause a processing device to perform any of the methods, operations, or steps described herein.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

NOTATION AND NOMENCLATURE

Figure 1:
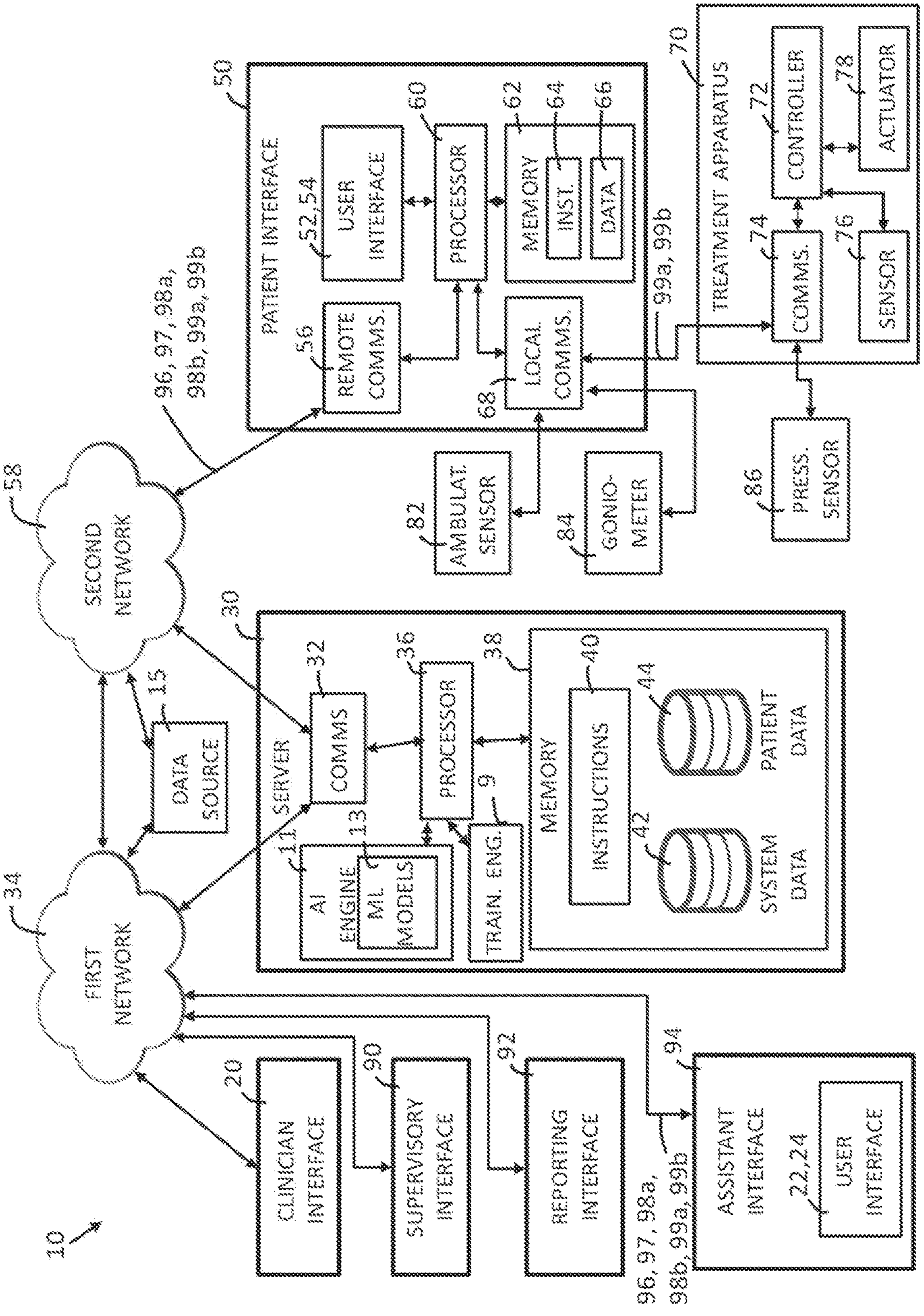
FIG. 1 generally illustrates a block diagram of an embodiment of a computer-implemented system for managing a treatment plan according to the principles of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

The terms telemedicine, telehealth, telemed, teletherapeutic, telemedicine, etc. may be used interchangeably herein.

The term "medical action(s)" may refer to any suitable action performed by the medical professional (e.g., or the healthcare professional), and such action or actions may include diagnoses, prescription of treatment plans, prescription of treatment devices, and the making, composing and/or executing of appointments, telemedicine sessions, prescriptions or medicines, telephone calls, emails, text messages, and the like.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining optimal remote examination procedures to create an optimal treatment plan for a patient having certain characteristics (e.g., vital-sign or other measurements; performance; demographic; psychographic; geographic; diagnostic; measurement- or test-based; medically historic; etiologic; cohort-associative; differentially diagnostic; surgical, physically therapeutic, behavioral, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment device, an amount of force exerted on a portion of the treatment device, a range of motion achieved on the treatment device, a movement speed of a portion of the treatment device, a duration of use of the treatment device, an indication of a plurality of pain levels using the treatment device, or some combination thereof. The measurement information may include, e.g., one or more vital signs of the user, a respiration rate of the user, a heartrate of the user, a temperature of the user, an SpO2-measurement of the blood oxygen level of the user (e.g., oxygen saturation level), a blood pressure of the user, a glucose level of the user, other suitable measurement information of the user, microbiome-related data pertaining to the user, or a combination thereof. It may be desirable to process and analyze the characteristics of a multitude of patients, the treatment plans performed for those patients, and the results of the treatment plans for those patients.

Further, another technical problem may involve distally treating, via a computing device during a telemedicine or telehealth session, a patient from a location different than a location at which the patient is located. An additional technical problem is controlling or enabling the control of, from the different location, a treatment device used by the patient at the location at which the patient is located. Oftentimes, when a patient undergoes rehabilitative surgery (e.g., knee surgery), a healthcare professional may prescribe a treatment device to the patient to use to perform a treatment protocol at their residence or any mobile location or temporary domicile. A healthcare professional may refer to a doctor, physician assistant, nurse, chiropractor, dentist, physical therapist, acupuncturist, physical trainer, coach, personal trainer, neurologist, cardiologist, or the like. A healthcare professional may refer to any person with a credential, license, degree, or the like in the field of medicine, physical therapy, rehabilitation, or the like.

When the healthcare professional is located in a different location from the patient and the treatment device, it may be technically challenging for the healthcare professional to monitor the patient's actual progress (as opposed to relying on the patient's word about their progress) using the treatment device, modify the treatment plan according to the patient's progress, adapt the treatment device to the personal characteristics of the patient as the patient performs the treatment plan, and the like.

Additionally, or alternatively, the patient may have or develop one or more alignment issues, including joint or other alignment issues, such as ankle alignment issues, knee alignment issues, hip alignment issues, spine alignment issues, elbow alignment issues, shoulder alignment issues, wrist alignment issues, and the like. When the healthcare professional is located in a different location from the patient and the treatment device, it may be difficult for the healthcare professional to assess or identify such alignment issues and to take appropriate action. Consequently, the patient may become injured or suffer various side effects of the one or more alignment issues.

Accordingly, systems and methods, such as those described herein, may identify one or more alignment issues of the patient based on data pertaining to a patient or to a user of the treatment device. In some embodiments, the systems and methods described herein may be configured to receive treatment data pertaining to a user capable of using the treatment device to perform the treatment plan. The user may include a patient or a person using the treatment device to perform various exercises. In some embodiments, the systems and methods described herein may be configured to receive the treatment data while the user uses the treatment device. Additionally, or alternatively, the systems and methods described herein may be configured to receive the treatment data while the user uses the treatment device during a telemedicine session.

The treatment plan may include a rehabilitation plan, a prehabilitation plan, an exercise plan, or other suitable treatment plan. The treatment data may include various characteristics of the user, various measurement information pertaining to the user while the user uses the treatment device, various performance measurement information pertaining to the use of the treatment device by the user, various characteristics of the treatment device, the treatment plan, other suitable data, or a combination thereof.

In some embodiments, while the user uses the treatment device to perform the treatment plan, at least some of the treatment data may correspond to sensor data from a sensor configured to sense various characteristics of the treatment device and/or the measurement information of the user. Additionally, or alternatively, while the user uses the treatment device to perform the treatment plan, at least some of the treatment data may correspond to sensor data from a sensor associated with a wearable device configured to sense the measurement information of the user.

The various characteristics of the treatment device may include one or more settings of the treatment device, a current revolutions per time period (e.g., such as one minute) of a rotating member (e.g., such as a wheel) of the treatment device, a resistance setting of the treatment device, other suitable characteristics of the treatment device, or a combination thereof. The measurement information may include one or more vital signs of the user, a respiration rate of the user, a heartrate of the user, a temperature of the user, an SpO2-measurement of the blood oxygen level of the user (e.g., oxygen saturation level), a blood pressure of the user, a glucose level of the user, other suitable measurement information of the user, microbiome-related data pertaining to the user, or a combination thereof.

The various characteristics of the user may include a user age, a user height, a user weight, one or more health-related or other conditions or characteristics of the user, a location of the user, and the like. The various performance measurement information may include, while the user uses the treatment device, at least one of a pedal pressure measurement of a first pedal of the treatment device, a pedal rotational angle of the first pedal of the treatment device, wherein the pedal rotational angle of the first pedal is associated with a respective pedal pressure measurement, a pedal pressure measurement of a second pedal of the treatment device, a pedal rotational angle of the second pedal of the treatment device for a respective pedal pressure measurement, and/or other suitable performance measurement information.

The method also includes receiving user related data (URD) associated with the user. In some embodiments, the systems and methods described herein may be configured to receive URD pertaining to the user. The URD may include at least baseline data (e.g., or previously captured or measured data) for the user during engagement, by the user, in at least one activity.

The systems and methods described herein may be configured to receive alignment data associated with the user while the user engages in at least one activity. The alignment data may be associated with and/or received from various sources, such as one or more goniometers associated with the user, wherein the one or more goniometers are configured to capture goniometric data associated with the user while the user uses the treatment device and/or engages in the at least one activity, one or more pedometers associated with the user, wherein the one or more pedometers are configured to capture pedometer data associated with the user while the user uses the treatment device and/or engages in the at least one activity, one or more pressure sensors associated with the treatment device and/or other suitable device configured to capture pressure data associated with the user while the user uses the treatment device and/or engages in the at least one activity, one or more image capturing device sensors configured to capture image data associated while the user uses the treatment device and/or engages in the at least one activity, other suitable sources, or a combination thereof.

The alignment data my include at least one of relative position data associated with at least one body part associated with the user (e.g., which may indicate a position of the user or a portion of the user, such as a body part of the user, relative to a reference point or plane), relative angle data associated with at least one body part associated with the user (e.g., which may indicate an angle of the at least one body part of the user relative to a reference point or plane), lateral motion data associated with at least one body part associated with the user, pressure data associated with at least one body part associated with the user (e.g., which may indicate an amount of pressure the body part of the user is exerting on a component of the treatment device or other suitable device, mechanism, sensor, and the like), rotational motion data associated with at least one body part associated with the user, other suitable alignment data, or a combination thereof.

The at least one activity may include walking, running, climbing, jumping, cycling, throwing, rolling, squatting, swimming, rowing, any other suitable activity or isometric, isotonic, plyometric, aerobic, anaerobic, or other exercise, or a combination thereof (e.g., including assisted activities (e.g., such as using a treadmill and the like) or unassisted activities). In some embodiments, the at least one activity may include at least one activity that the user previously engaged in while using the treatment device. In some embodiments, the at least one activity may include at least one activity that the user previously engaged in while not using the treatment device.

In some embodiments, the systems and methods described herein may be configured to identify, based on at least the treatment data, the URD, and the alignment data, at least one alignment characteristic associated with the user. The at least one alignment characteristic may include one or more alignment delta values associated with at least one alignment aspect of the user, one or more alignment scores associated with at least one alignment aspect of the user, one or more alignment performance values associated with at least one alignment aspect of the user, other suitable alignment characteristics associated with the user, or a combination thereof.

The alignment delta value may include at least one difference between at least one aspect of the alignment data associated with the user and at least one aspect of the treatment data and/or at least one aspect of the URD. Any difference referenced herein, including, without limitation, the alignment delta value, may be characterized or described by an absolute number or number of units (e.g., “3”, “5 inches”, “25 degrees” “0.15 radians” and the like), by a percentage difference (e.g., “20% more”, “15% less”), by a percentage point difference (e.g., “5.3 percentage points less than (or greater than)), by a parametrically ranked difference (e.g., “2$^{nd}$ highest vs. 5$^{th}$ highest”, therefore 3 ranks higher), by a qualitatively described difference (e.g., “very different”, “somewhat different”, “equal”, “more than”, “better than”, “less than”, “worse than” and the like), or by any other means of expressing or describing a difference). For example, the systems and methods described herein may be configured to compare the at least one aspect of the alignment data to the at least one aspect of the treatment data and/or the at least one aspect of the URD. The alignment data may include, for example, a relative position of a body part of the user, such as a relative angle of a knee of the user. The at least one aspect of the treatment data may include, for example, a pedal pressure measurement that may correspond to a pressure applied, during a telemedicine session or other suitable use of the treatment device, by the user to a first pedal of the treatment device. The at least one aspect of the URD may include a pedal pressure measurement that may correspond to a pressure applied by the user to the first pedal of the treatment device (e.g., which may provide a baseline pedal pressure for the user while using the treatment device). The pedal pressure measurement may include a pedal pressure measurement applied, by the user to the first pedal of the treatment device, during a previous use of the treatment device; an average pedal pressure measurement applied, by the user to the first pedal of the treatment device, over a number of previous uses of the treatment device; or other suitable pedal pressure measurement.

The systems and methods described herein may be configured to determine a difference between the pedal pressure measurement corresponding to the at least one aspect of the treatment data and the pedal pressure measurement corresponding to the at least one aspect of the URD. The systems and methods described herein may be configured to generate delta information based on the difference between the at least one aspect of the treatment data and the at least one aspect of the URD.

The systems and methods described herein may be configured to generate, based on the delta information and the at least one aspect of the alignment data, the alignment delta value. For example, the systems and methods described herein may be configured to determine, based on the delta information, an expected alignment value for the at least one body part of the user. The systems and methods described herein may be configured to determine, based on a difference between the expected alignment value and an alignment value corresponding to the at least one aspect of the alignment data, the alignment delta value. It should be understood that the systems and methods described herein may be configured to generate the alignment delta value using any suitable techniques in addition to or instead of those described herein. Additionally, or alternatively, the systems and methods described herein may be configured to identify any aspect of the at least one alignment characteristic of the user using any suitable technique in addition to or instead of those described herein.

In some embodiments, systems and methods described herein may be configured to provide, to a healthcare professional associated with the user, the treatment data, the URD, the alignment data, and/or the at least one alignment characteristic. In some embodiments, the systems and methods described herein may be configured to communicate with an interface at a computing device of the healthcare professional.

The healthcare professional may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare professional" may be a human being, a robot, a virtual assistant, a virtual assistant in a virtual and/or augmented reality, or an artificially intelligent entity, including a software program, integrated software and hardware, or hardware alone.

The interface may include a graphical user interface configured to provide the treatment data, the URD, the alignment data, and/or the at least one alignment characteristic and to receive input from the healthcare professional. The interface may include one or more interface mechanisms, such as text input fields, dropdown selection input fields, radio button input fields, virtual switch input fields, virtual lever input fields, audio mechanisms, haptic mechanisms, tactile mechanisms, biometric gesture recognition mechanisms, gesture controls, touchless user interfaces (TUIs), kinetic user interfaces (KUIs), tangible user interfaces, wired gloves, depth-aware cameras, stereo cameras, gesture-based controllers, or otherwise activated and/or selected input fields, other suitable input fields, or a combination thereof.

The interface may be configured to receive the information associated with the at least one alignment characteristic. For example, the systems and methods described herein may be configured to store, at a memory, the treatment data, the URD, the alignment data, and/or the at least one alignment characteristic. The interface at the computing device of the healthcare professional may be configured to retrieve from the memory the treatment data, the URD, the alignment data, and/or the at least one alignment characteristic.

The healthcare professional may use at least one artificial intelligence engine configured to use at least one machine learning model that generates, based on the at least one alignment characteristic, treatment plan input. The artificial intelligence engine may be associated with at least one of the treatment device, a remotely located server computing device, the computing device of a healthcare professional, another suitable device or server, or a combination thereof. The healthcare professional may include a human who uses the computing device associated with the healthcare professional to access the artificial intelligence engine, an artificially intelligent entity configured to use the artificial intelligence engine, or a combination thereof. The treatment plan input may include information indicating at least one alignment issue of the user, information indicating at least one modification to the treatment plan, other suitable information indicating other suitable aspects of an analysis performed by the healthcare professional, or a combination thereof.

In some embodiments, the systems and methods describe may be configured to modify at least one aspect of the treatment plan in response to receiving, from the healthcare professional, the treatment plan input, wherein the treatment plan input includes at least one modification to the at least one aspect of the treatment plan. In some embodiments, the systems and methods described herein may be configured to perform, in response to receiving treatment plan input, at least one treatment action indicated by the treatment plan input. The at least one treatment action may include modifying at least one aspect of the treatment plan, controlling (e.g., while the user uses the treatment device) at least one aspect of the treatment device, generating (e.g., based on the treatment plan input) a notification, transmitting (e.g., to at least one of the user and an agent of the user, such as a primary care physician, a physical therapist, a caregiver, any medical, healthcare, therapeutic, personal trainer or other professional, and/or other suitable agent of the user) the notification, any other suitable treatment action, or a combination thereof.

In some embodiments, transmitting the notification may comprise: transmitting the notification to one or more mobile devices associated with the user or the agent of the user, to electronic mail addresses of the user or the agent of the user, to applications associated with the use of the treatment device, to displays of the treatment device, or to other suitable locations. The notification may include at least an indication of one or more alignment issues associated with the user and/or the at least one treatment action. Additionally, or alternatively, the notification may comprise an aspect that includes sound, an aspect that includes a visual display or projection, any other suitable sensorial or other aspect, or a combination thereof.

If the at least one treatment action includes modifying one or more aspects of the treatment plan and/or one or more characteristics of the treatment device, the systems and methods described herein may modify the one or more aspects of the treatment plan and/or the one or more characteristics of the treatment device. For example, the at least one treatment action may indicate an increase or decrease in the resistance setting of the treatment device, or other suitable modification to the one or more characteristics of the treatment device. Additionally, or alternatively, the at least one treatment action may indicate an increase or decrease in an amount of time the user is required to use the treatment device according to the treatment plan, or other suitable modifications to the treatment plan.

The healthcare professional may, while the user uses the treatment device to perform the treatment plan, continuously or periodically receive and/or review treatment data, URD, alignment data, and/or alignment characteristics of the user. Based on one or more trends indicated by the continuously and/or periodically received treatment information, the healthcare professional may determine whether to modify the treatment plan and/or to control the one or more characteristics of the treatment device. For example, the one or more trends may indicate an increase in the relative alignment angle of one or more body parts of the user or other suitable trends, and the trend's indication(s) or trends' indication(s) may themselves indicate that the user is not performing the treatment plan properly and/or that the performance of the treatment plan by the user is not having the desired effect.

Typically, to treat one or more conditions of the patient, the patient, who may be of any age, inclusive from that of a neonate to the limit of the human lifespan, may perform, using the treatment device, various aspects of the treatment plan. For example, the patient may be recovering from an orthopedic surgery, a cardiac surgery, a vascular surgery, a trauma repair or mitigation surgery, a neurological surgery (including, without limitation, spinal or back surgery), a gastrointestinal surgery, a cancer surgery (including, without limitation, surgery for the partial or complete removal or in-body attenuation of neoplasms), a genito-urological surgery, a gynecological surgery, or other surgery and may use the treatment device to rehabilitate one or more affected portions of the patient's body. Alternatively, the patient may be recovering from a neurological surgery or a program to treat mental unwellness and may use the treatment device to rehabilitate neurological or other mental responses or brain functions which have a physical manifestation with regard to one or more directly or indirectly affected portions of the patient's body. Alternatively, the patient may be being treated for physical and/or mental conditions associated with post-traumatic stress disorder (PTSD) and may use the treatment device to rehabilitate neurological or other mental responses or brain functions, wherein the functions are associated with a physical manifestation.

Further, the patient, while recovering from post-traumatic stress disorder, may use the treatment device to improve general mental health (e.g., through exercise, goal-oriented activity and achievement, and the like). Alternatively, the patient may be under treatment for a somatoform disorder associated with PTSD or other trauma, injury, and the like. The patient may use the treatment device to rehabilitate neurological or other mental responses or brain functions, which have a physical manifestation and/or other mental manifestation. Such conditions may be referred to as primary conditions (e.g., conditions for which the patient uses the treatment device to perform the treatment plan). However, the patient may have one or other conditions of which the healthcare provider caring for the patient and/or the patient is unaware. These may be referred to as secondary, comorbid or secondary comorbid conditions (e.g., conditions not currently being treated and/or conditions of which the healthcare provider and/or the patient is unaware). As used herein, "secondary condition" means, without limitation, any condition that is not the primary condition, i.e., a first secondary condition, a second secondary condition, a third secondary condition, etc., or alternatively worded, a secondary condition, a tertiary condition, a quaternary condition, etc.

Similarly, the patient may use the treatment device to perform strength training aspects of the treatment plan or other strength training plan. However, the patient may have one or more secondary and/or comorbid conditions not yet identified by or known to the healthcare provider or the patient. Accordingly, the systems and methods described herein may be configured to identify one or more conditions of the patient based, at least in part, on the use of the treatment device by the patient. In some embodiments, the systems and methods described herein may be configured to determine, using at least the at least one alignment characteristic, whether the at least one alignment characteristic correlates with at least one secondary condition of the user. The at least one secondary condition may include any condition for which the user is not being treated while using the treatment device (e.g., conditions not currently being treated and/or conditions of which the healthcare provider and/or the patient is unaware).

In some embodiments, the systems and methods described herein may be configured to determine whether the at least one alignment characteristic is correlated with the at least one secondary condition, by writing to an associated memory the at least one alignment characteristic. The associated memory may further be configured to be accessed by an artificial intelligence engine. The artificial intelligence engine may be configured to use at least one machine learning model to generate, using the at least one alignment characteristic, at least one of secondary condition output predictions. As used herein, a "secondary condition output prediction" refers to output generated by the machine learning model and/or the artificial intelligence engine. The artificial intelligence engine may include any suitable artificial intelligence engine, including those described herein. The at least one machine learning model may include any suitable machine learning model, including those described herein. For example, the at least one machine learning model may include a deep network comprising multiple levels of non-linear operations or other suitable model. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

In some embodiments, the artificial intelligence engine may be configured to use the at least one machine learning model to generate, further using secondary condition information associated with other users, the at least one of secondary condition output predictions. At least some of the other users may be associated with a cohort to which the user belongs; alternatively, all of the other users may be associated with the cohort to which the user belongs; further alternatively, the other users may be associated with other cohorts; or the other users may not be associated with any identified cohort. In some embodiments, the other users may have characteristics similar to those of the user. In some embodiments, measurements pertaining to the other users may include measurements similar to the at least one measurement pertaining to the user.

The at least one secondary condition output prediction generated by the at least one machine learning model may indicate one or more secondary conditions that may be associated with the patient. For example, the machine learning model may determine, based on the at least one alignment characteristic, that a predicted secondary condition may be affecting the patient. The at least one secondary condition output prediction may include a probabilistic prediction (using, for example and without limitation, parametric, non-parametric, Bayesian and/or Markovian probabilistic methods), a stochastic prediction (using, for example and without limitation, non-deterministic finite state automata), or a deterministic prediction (using, for example and without limitation, finite state automata). The systems and methods described herein may be configured to receive, from the artificial intelligence engine, the at least one secondary condition output prediction.

In some embodiments, the systems and methods described herein may be configured to, in response to a determination that the at least one alignment characteristic is correlated with the at least one at least one secondary condition of the user, generate secondary condition information indicating at least the secondary condition. The systems and methods described herein may be configured to write to the associated memory, for access at the computing device of the healthcare professional, the secondary condition information and/or the secondary condition output prediction.

In some embodiments, the healthcare professional may review at least the secondary condition information and/or the at least one secondary condition output prediction and determine whether to pursue treatment of one or more secondary conditions identified by the secondary condition information and/or the at least one secondary condition output prediction, to modify at least one aspect of the treatment plan, and/or to modify or adjust one or more characteristics of the treatment device. The determination of whether to pursue treatment may be binary (e.g., pursue the treatment, do not pursue the treatment) or probabilistic (e.g., the treatment has a 35% risk of death, the treatment has a 75% chance of producing the desired rehabilitative outcome, etc.), wherein the probability is used by the patient and or the patient's representatives (if the patient is incapacitated) to determine whether to pursue a particular treatment or to determine which of one or more treatments to pursue.

In some embodiments, the systems and methods described herein may be configured to modify at least one aspect of the treatment plan in response to receiving, from a healthcare professional, treatment plan input, as described herein. The treatment plan input may include at least one modification to the at least one aspect of the treatment plan. The treatment plan input may be generated, by the healthcare professional, based on the secondary condition information.

In some embodiments, the systems and methods described herein may be configured to use artificial intelligence and/or machine learning to assign patients to cohorts and to dynamically control a treatment device based on the assignment during an adaptive telemedicine session. In some embodiments, numerous treatment devices may be provided to patients. The treatment devices may be used by the patients to perform treatment plans in their residences, at a gym, at a rehabilitative center, at a hospital, or any suitable location, including permanent or temporary domiciles.

In some embodiments, the treatment devices may be communicatively coupled to a server. Characteristics of the patients, including the treatment data, may be collected before, during, and/or after the patients perform the treatment plans. For example, the personal information, the performance information, and the measurement information may be collected before, during, and/or after the person performs the treatment plans. The results (e.g., improved performance or decreased performance) of performing each exercise may be collected from the treatment device throughout the treatment plan and after the treatment plan is performed. The parameters, settings, configurations, etc. (e.g., position of pedal, amount of resistance, etc.) of the treatment device may be collected before, during, and/or after the treatment plan is performed.

Each characteristic of the patient, each result, and each parameter, setting, configuration, etc. may be timestamped and may be correlated with a particular step in the treatment plan. Such a technique may enable determining which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment devices and/or any suitable computing device (e.g., computing devices where personal information is entered, such as the interface of the computing device described herein, a clinician interface, patient interface, and the like) over time as the patients use the treatment devices to perform the various treatment plans. The data that may be collected may include the characteristics of the patients, the treatment plans performed by the patients, the results of the treatment plans, any of the data described herein, any other suitable data, or a combination thereof.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment device for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment device while the new patient uses the treatment device to perform the treatment plan.

As may be appreciated, the characteristics of the new patient (e.g., a new user) may change as the new patient uses the treatment device to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion.

A different treatment plan may be selected for the new patient, and the treatment device may be controlled, distally (e.g., which may be referred to as remotely) and based on the different treatment plan, the treatment device while the new patient uses the treatment device to perform the treatment plan. Such techniques may provide the technical solution of distally controlling a treatment device.

Further, the systems and methods described herein may lead to faster recovery times and/or better results for the patients because the treatment plan that most accurately fits their characteristics is selected and implemented, in real-time, at any given moment. "Real-time" may also refer to near real-time, which may be less than 10 seconds. As described herein, the term "results" may refer to medical results or medical outcomes. Results and outcomes may refer to responses to medical actions.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may be trained to output treatment plans that are not optimal i.e., sub-optimal, nonstandard, or otherwise excluded (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient. In some embodiments, the artificial intelligence engine may monitor the treatment data received while the patient (e.g., the user) with, for example, high blood pressure, uses the treatment device to perform an appropriate treatment plan and may modify the appropriate treatment plan to include features of an excluded treatment plan that may provide beneficial results for the patient if the treatment data indicates the patient is handling the appropriate treatment plan without aggravating, for example, the high blood pressure condition of the patient.

In some embodiments, the treatment plans and/or excluded treatment plans may be presented, during a telemedicine or telehealth session, to a healthcare professional. The healthcare professional may select a particular treatment plan for the patient to cause that treatment plan to be transmitted to the patient and/or to control, based on the treatment plan, the treatment device. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment device.

In such cases, the recommended treatment plans and/or excluded treatment plans may be presented simultaneously with a video of the patient in real-time or near real-time during a telemedicine or telehealth session on a user interface of a computing device of a healthcare professional. The video may also be accompanied by audio, text and other multimedia information. Real-time may refer to less than or equal to 2 seconds. Real-time may also refer to near real-time, which may be less than 10 seconds or any reasonably proximate different between two different times. Additionally, or alternatively, near real-time may refer to any interaction of a sufficiently short time to enable two individuals to engage in a dialogue via such user interface and will generally be less than 10 seconds but greater than 2 seconds.

Presenting the treatment plans generated by the artificial intelligence engine concurrently with a presentation of the patient video may provide an enhanced user interface because the healthcare professional may continue to visually and/or otherwise communicate with the patient while also reviewing the treatment plans on the same user interface. The enhanced user interface may improve the healthcare professional's experience using the computing device and may encourage the healthcare professional to reuse the user interface. Such a technique may also reduce computing resources (e.g., processing, memory, network) because the healthcare professional does not have to switch to another user interface screen to enter a query for a treatment plan to recommend based on the characteristics of the patient. The artificial intelligence engine may be configured to provide, dynamically on the fly, the treatment plans and excluded treatment plans.

In some embodiments, the treatment device may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare professional may adapt, remotely during a telemedicine session, the treatment device to the needs of the patient by causing a control instruction to be transmitted from a server to treatment device. Such adaptive nature may improve the results of recovery for a patient, furthering the goals of personalized medicine, and enabling personalization of the treatment plan on a per-individual basis.

FIG. 1 generally illustrates a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store (e.g., write to an associated memory) and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36.

The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

Additionally, or alternatively, the characteristics (e.g., personal, performance, measurement, etc.) of the people, the treatment plans followed by the people, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment devices and/or computing devices over time and stored in the database 44. The characteristic data, treatment plan data, and results data may be correlated in the patient-cohort databases in the patient data store 44. The characteristics of the people may include personal information, performance information, and/or measurement information.

In addition to the historical information about other people stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another person in a particular cohort (e.g., cohort A) and the patient may be assigned to that cohort.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their characteristics, select treatment plans using real-time and historical data correlations involving patient cohort-equivalents, and control a treatment device 70, among other things.

The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other suitable computing device, or a combination thereof. The training engine 9 may be cloud-based or a real-time software platform, and it may include privacy software or protocols, and/or security software or protocols.

To train the one or more machine learning models 13, the training engine 9 may use a training data set of a corpus of the characteristics of the people that used the treatment device 70 to perform treatment plans, the details (e.g., treatment protocol including exercises, amount of time to perform the exercises, how often to perform the exercises, a schedule of exercises, parameters/configurations/settings of the treatment device 70 throughout each step of the treatment plan, etc.) of the treatment plans performed by the people using the treatment device 70, and the results of the treatment plans performed by the people. The one or more machine learning models 13 may be trained to match patterns of characteristics of a patient with characteristics of other people assigned to a particular cohort. The term "match" may refer to an exact match, a correlative match, a substantial match, etc. The one or more machine learning models 13 may be trained to receive the characteristics of a patient as input, map the characteristics to characteristics of people assigned to a cohort, and select a treatment plan from that cohort. The one or more machine learning models 13 may also be trained to control, based on the treatment plan, the machine learning apparatus 70.

Different machine learning models 13 may be trained to recommend different treatment plans for different desired results. For example, one machine learning model may be trained to recommend treatment plans for most effective recovery, while another machine learning model may be trained to recommend treatment plans based on speed of recovery.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

As is generally illustrated in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment device 70 configured to be manipulated by the patient and/or to manipulate a body part of the patient for performing activities according to the treatment plan. In some embodiments, the treatment device 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment device 70 may be any suitable medical, rehabilitative, therapeutic, etc. apparatus configured to be controlled distally via another computing device to treat a patient and/or exercise the patient. The treatment device 70 may be an electromechanical machine including one or more weights, an electromechanical bicycle, an electromechanical spin-wheel, a smart-mirror, a treadmill, or the like. The body part may include, for example, a spine, a hand, a foot, a knee, or a shoulder. The body part may include a part of a joint, a bone, or a muscle group, such as one or more vertebrae, a tendon, or a ligament. As is generally illustrated in FIG. 1, the treatment device 70 includes a controller 72, which may include one or more processors, computer memory, and/or other components. The treatment device 70 also includes a fourth communication interface 74 configured to communicate with the patient interface 50 via the local communication interface 68. The treatment device 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment device 70 such as, for example, a force a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment device 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment device 70.

The system 10 generally illustrated in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 generally illustrated in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 generally illustrated in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 generally illustrated in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 generally illustrated in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for a healthcare professional, such as those described herein, to remotely communicate with the patient interface 50 and/or the treatment device 70. Such remote communications may enable the healthcare professional to provide assistance or guidance to a patient using the system 10. More specifically, the assistant interface 94 is configured to communicate a telemedicine signal 96, 97, 98*a*, 98*b*, 99*a*, 99*b* with the patient interface 50 via a network connection such as, for example, via the first network 34 and/or the second network 58. The telemedicine signal 96, 97, 98*a*, 98*b*, 99*a*, 99*b* comprises one of an audio signal 96, an audiovisual signal 97, an interface control signal 98*a* for controlling a function of the patient interface 50, an interface monitor signal 98*b* for monitoring a status of the patient interface 50, an apparatus control signal 99*a* for changing an operating parameter of the treatment device 70, and/or an apparatus monitor signal 99*b* for monitoring a status of the treatment device 70. In some embodiments, each of the control signals 98*a*, 99*a* may be unidirectional, conveying commands from the assistant interface 94 to the patient interface 50. In some embodiments, in response to successfully receiving a control signal 98*a*, 99*a* and/or to communicate successful and/or unsuccessful implementation of the requested control action, an acknowledgement message may be sent from the patient interface 50 to the assistant interface 94. In some embodiments, each of the monitor signals 98*b*, 99*b* may be unidirectional, status-information commands from the patient interface 50 to the assistant interface 94. In some embodiments, an acknowledgement message may be sent from the assistant interface 94 to the patient interface 50 in response to successfully receiving one of the monitor signals 98*b*, 99*b*.

In some embodiments, the patient interface 50 may be configured as a pass-through for the apparatus control signals 99*a* and the apparatus monitor signals 99*b* between the treatment device 70 and one or more other devices, such as the assistant interface 94 and/or the server 30. For example, the patient interface 50 may be configured to transmit an apparatus control signal 99*a* in response to an apparatus control signal 99*a* within the telemedicine signal 96, 97, 98*a*, 98*b*, 99*a*, 99*b* from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98*a*, 98*b*, 99*a*, 99*b* may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the healthcare professional may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the healthcare professional to speak to a patient via the patient interface 50. In some embodiments, assistant input device 22 may be configured to provide voice-based functionalities, with hardware and/or software configured to interpret spoken instructions by the healthcare professional by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the healthcare professional. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the healthcare professional. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for patients and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network.

In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment device 70 may each operate from a patient location geographically separate from a location of the assistant interface 94. For example, the patient interface 50 and the treatment device 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as a healthcare professional remotely from any conventional office infrastructure. Such remote work may be performed, for example, where the assistant interface 94 takes the form of a computer and/or telephone. This remote work functionality may allow for work-from-home arrangements that may include part time and/or flexible work hours for a healthcare professional.

Figure 2:
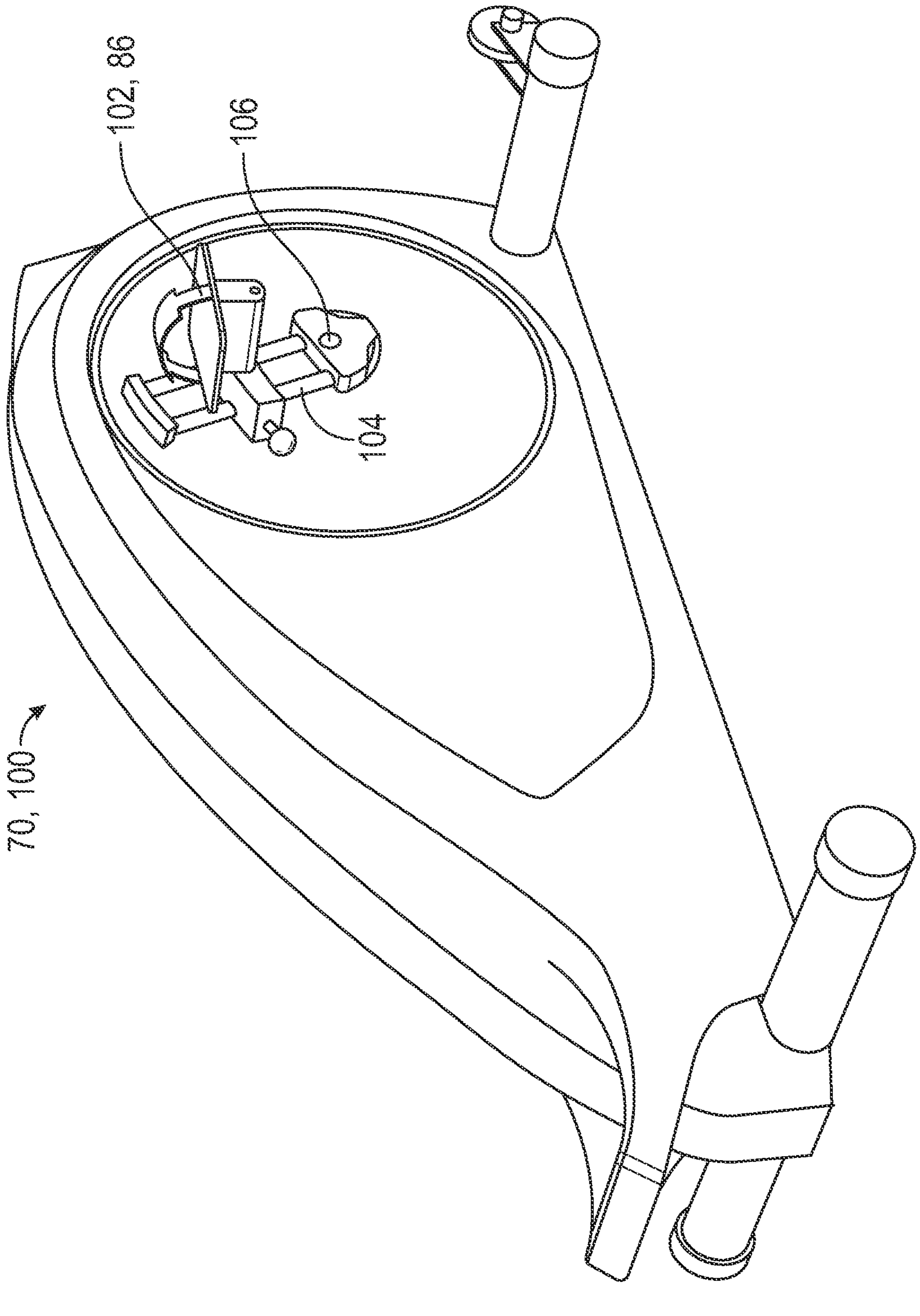
FIG. 2 generally illustrates a perspective view of an embodiment of a treatment device according to the principles of the present disclosure.
Figure 3:
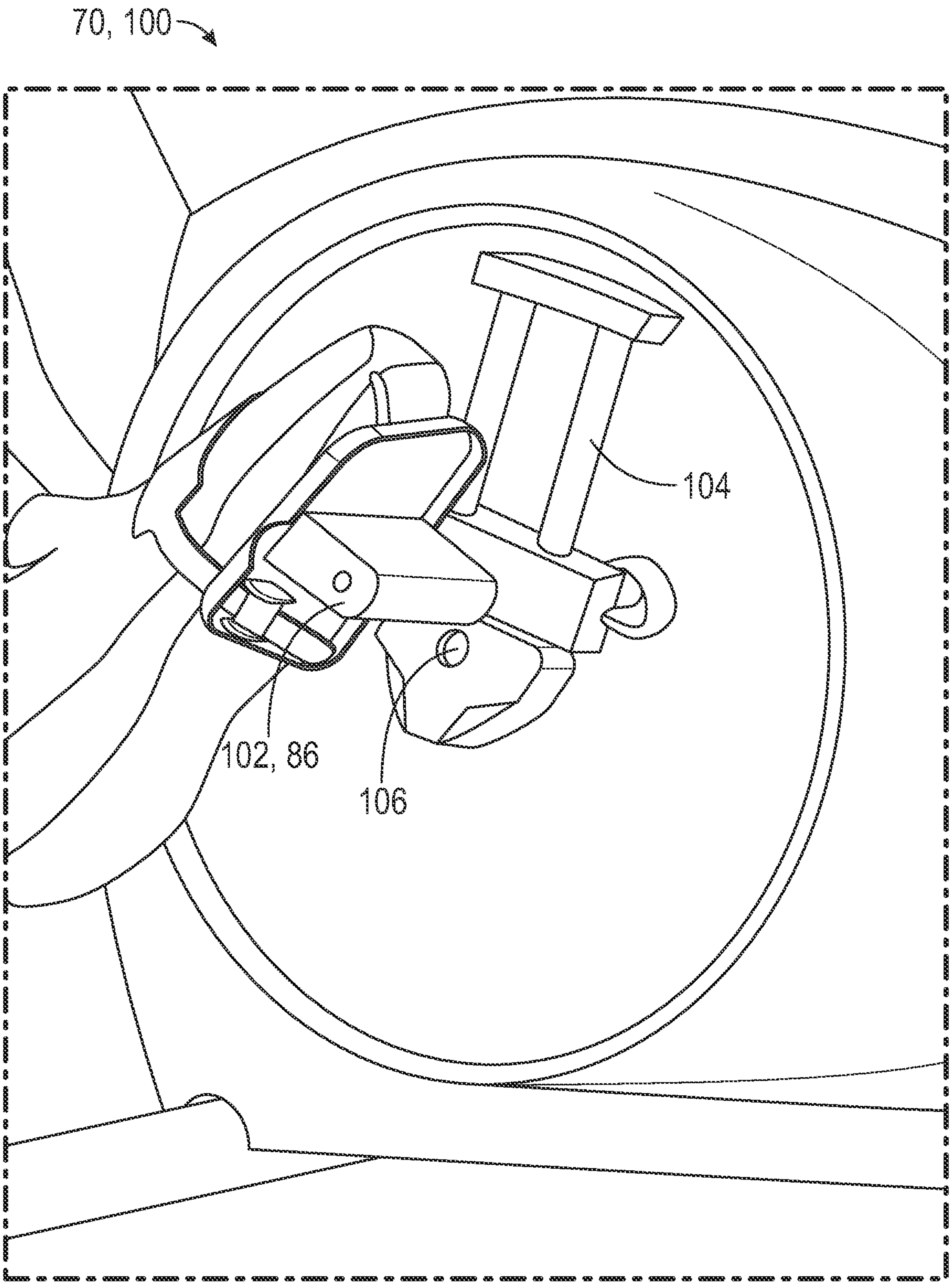
FIG. 3 generally illustrates a perspective view of a pedal of the treatment device of FIG. 2 according to the principles of the present disclosure.

FIGS. 2-3 show an embodiment of a treatment device 70. More specifically, FIG. 2 generally illustrates a treatment device 70 in the form of a stationary cycling machine 100, which may be called a stationary bike, for short. The stationary cycling machine 100 includes a set of pedals 102 each attached to a pedal arm 104 for rotation about an axle 106. In some embodiments, and as is generally illustrated in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment device 70 and/or to the patient interface 50.

Figure 4:
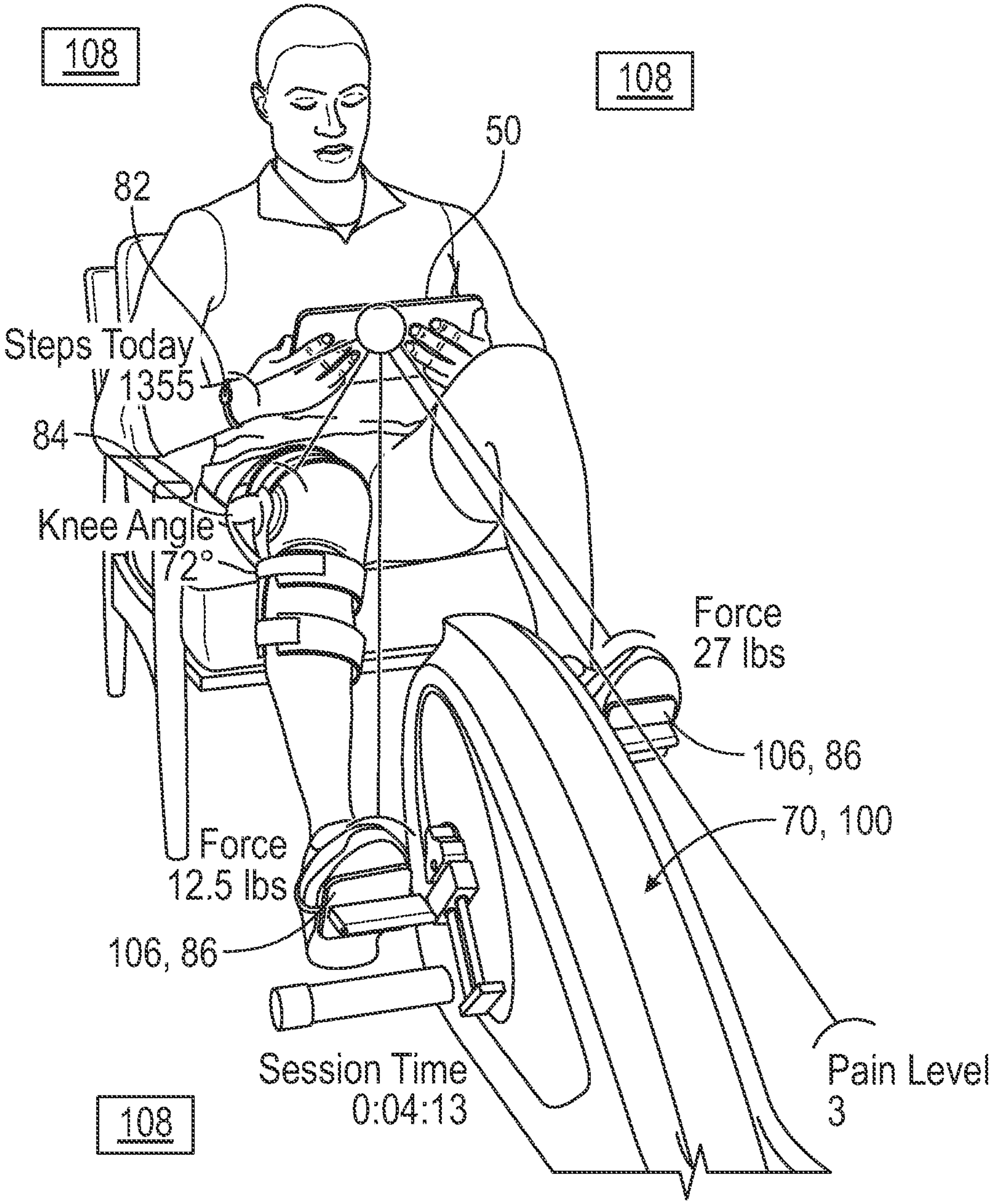
FIG. 4 generally illustrates a perspective view of a person using the treatment device of FIG. 2 according to the principles of the present disclosure.

FIG. 4 generally illustrates a person (a patient) using the treatment device of FIG. 2, and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment device 70.

FIG. 4 generally illustrates the patient wearing the ambulation sensor 82 on his wrist, with a note showing "STEPS TODAY 1355", indicating that the ambulation sensor 82 has recorded and transmitted that step count to the patient interface 50. FIG. 4 also generally illustrates the patient wearing the goniometer 84 on his right knee, with a note showing "KNEE ANGLE 72°", indicating that the goniometer 84 is measuring and transmitting that knee angle to the patient interface 50. FIG. 4 also generally illustrates a right side of one of the pedals 102 with a pressure sensor 86 showing "FORCE 12.5 lbs.," indicating that the right pedal pressure sensor 86 is measuring and transmitting that force measurement to the patient interface 50.

FIG. 4 also generally illustrates a left side of one of the pedals 102 with a pressure sensor 86 showing "FORCE 27 lbs.", indicating that the left pedal pressure sensor 86 is measuring and transmitting that force measurement to the patient interface 50. FIG. 4 also generally illustrates other patient data, such as an indicator of "SESSION TIME 0:04:13", indicating that the patient has been using the treatment device 70 for 4 minutes and 13 seconds. This session time may be determined by the patient interface 50 based on information received from the treatment device 70. FIG. 4 also generally illustrates an indicator showing "PAIN LEVEL 3". Such a pain level may be obtained from the patent in response to a solicitation, such as a question, presented upon the patient interface 50.

Figure 5:
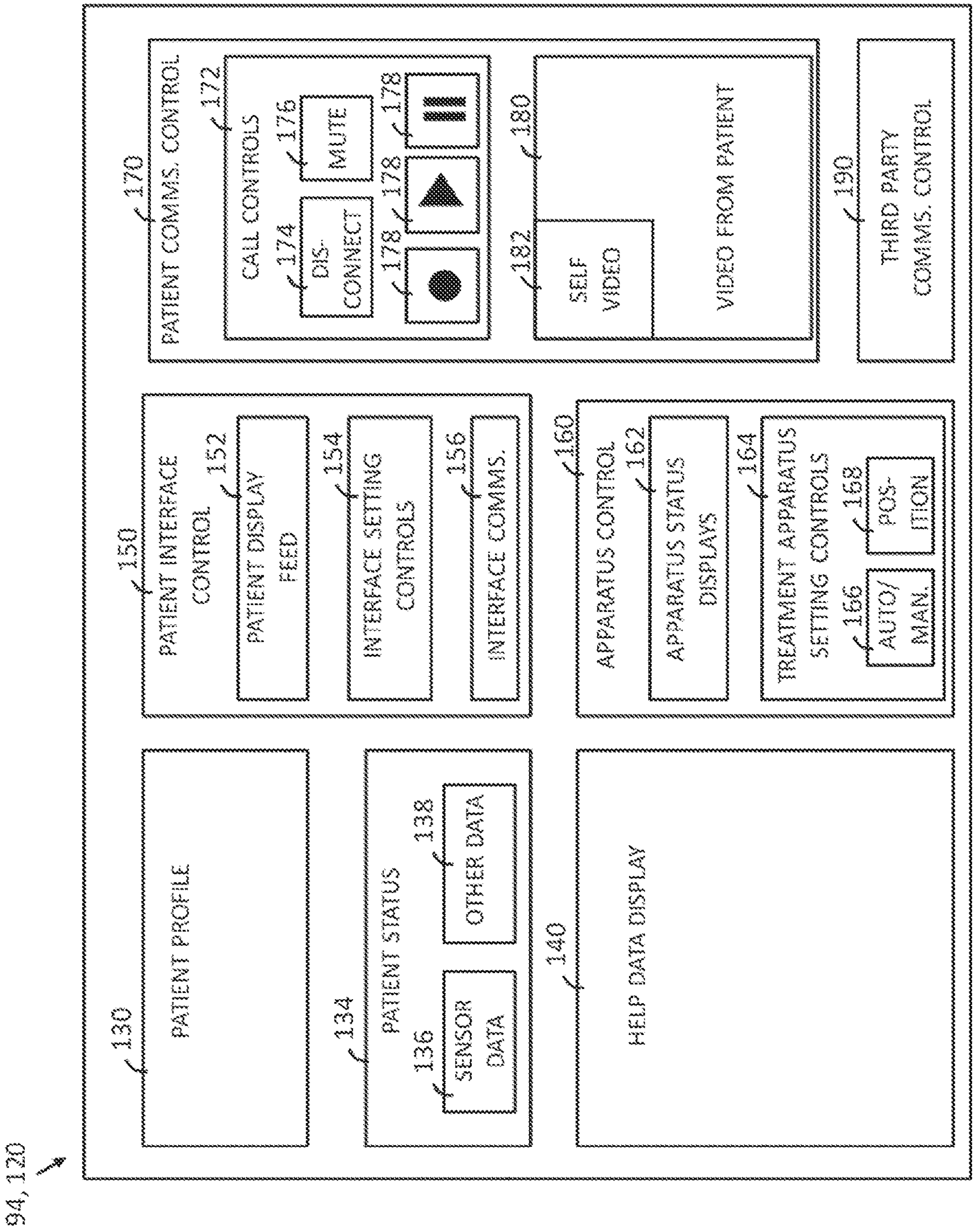
FIG. 5 generally illustrates an example embodiment of an overview display of an assistant interface according to the principles of the present disclosure.

FIG. 5 is an example embodiment of an overview display 120 of the assistant interface 94. Specifically, the overview display 120 presents several different controls and interfaces for the healthcare professional to remotely assist a patient with using the patient interface 50 and/or the treatment device 70. This remote assistance functionality may also be called telemedicine or telehealth.

Specifically, the overview display 120 includes a patient profile display 130 presenting biographical information regarding a patient using the treatment device 70. The patient profile display 130 may take the form of a portion or region of the overview display 120, as is generally illustrated in FIG. 5, although the patient profile display 130 may take other forms, such as a separate screen or a popup window.

In some embodiments, the patient profile display 130 may include a limited subset of the patient's biographical information. More specifically, the data presented upon the patient profile display 130 may depend upon the healthcare professional's need for that information. For example, a healthcare professional that is assisting the patient with a medical issue may be provided with medical history information regarding the patient, whereas a technician troubleshooting an issue with the treatment device 70 may be provided with a much more limited set of information regarding the patient. The technician, for example, may be given only the patient's name.

The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment device 70. Such treatment plan information may be limited to a healthcare professional. For example, a healthcare professional assisting the patient with an issue regarding the treatment regimen may be provided with treatment plan information, whereas a technician troubleshooting an issue with the treatment device 70 may not be provided with any information regarding the patient's treatment plan.

In some embodiments, one or more recommended treatment plans and/or excluded treatment plans may be presented in the patient profile display 130 to the healthcare professional. The one or more recommended treatment plans and/or excluded treatment plans may be generated by the artificial intelligence engine 11 of the server 30 and received from the server 30 in real-time during, inter alia, a telemedicine or telehealth session. An example of presenting the one or more recommended treatment plans and/or ruled-out treatment plans is described below with reference to FIG. 7.

The example overview display 120 generally illustrated in FIG. 5 also includes a patient status display 134 presenting status information regarding a patient using the treatment device. The patient status display 134 may take the form of a portion or region of the overview display 120, as is generally illustrated in FIG. 5, although the patient status display 134 may take other forms, such as a separate screen or a popup window.

The patient status display 134 includes sensor data 136 from one or more of the external sensors 82, 84, 86, and/or from one or more internal sensors 76 of the treatment device 70. In some embodiments, the patient status display 134 may include sensor data from one or more sensors of one or more wearable devices worn by the patient while using the treatment device 70. The one or more wearable devices may include a watch, a bracelet, a necklace, a headband, a wristband, an ankle band, any other suitable band, eyeglasses or eyewear (such as, without limitation, Google Glass) a chest or torso strap, a device configured to be worked on, attached to, or communicatively coupled to a body, and the like. While the user is using the treatment device 70, the one or more wearable devices may be configured to monitor, with respect to the user, a heartrate, a temperature, a blood pressure, an eye dilation, one or more vital signs, one or more metabolic markers, one or more biomarkers, and the like. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the healthcare professional/user's need for and/or qualifications to view that information.

The example overview display 120 generally illustrated in FIG. 5 also includes a help data display 140 presenting information for the healthcare professional to use in assisting the patient. The help data display 140 may take the form of a portion or region of the overview display 120, as is generally illustrated in FIG. 5. The help data display 140 may take other forms, such as a separate screen or a popup window. The help data display 140 may include, for example, presenting answers to frequently asked questions regarding use of the patient interface 50 and/or the treatment device 70.

The help data display 140 may also include research data or best practices. In some embodiments, the help data display 140 may present scripts for answers or explanations in response to patient questions. In some embodiments, the help data display 140 may present flow charts or walk-throughs for the healthcare professional to use in determining a root cause and/or solution to a patient's problem.

In some embodiments, the assistant interface 94 may present two or more help data displays 140, which may be the same or different, for simultaneous presentation of help data for use by the healthcare professional. for example, a first help data display may be used to present a troubleshooting flowchart to determine the source of a patient's problem, and a second help data display may present script information for the healthcare professional to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 generally illustrated in FIG. 5 also includes a patient interface control 150 presenting information regarding the patient interface 50, and/or to modify one or more settings of the patient interface 50. The patient interface control 150 may take the form of a portion or region of the overview display 120, as is generally illustrated in FIG. 5. The patient interface control 150 may take other forms, such as a separate screen or a popup window. The patient interface control 150 may present information communicated to the assistant interface 94 via one or more of the interface monitor signals 98*b*.

As is generally illustrated in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50.

In some embodiments, the display feed 152 may include abbreviated information regarding the display screen currently being presented by the patient interface 50, such as a screen name or a screen number. The patient interface control 150 may include a patient interface setting control 154 for the healthcare professional to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the healthcare professional to remotely view and/or control the patient interface 50. For example, the patient interface setting control 154 may enable the healthcare professional to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the healthcare professional to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the healthcare professional to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the healthcare professional to change the font size setting of the patient interface 50.

The example overview display 120 generally illustrated in FIG. 5 also includes an interface communications display 156 showing the status of communications between the patient interface 50 and one or more other devices 70, 82, 84, such as the treatment device 70, the ambulation sensor 82, and/or the goniometer 84. The interface communications display 156 may take the form of a portion or region of the overview display 120, as is generally illustrated in FIG. 5.

The interface communications display 156 may take other forms, such as a separate screen or a popup window. The interface communications display 156 may include controls for the healthcare professional to remotely modify communications with one or more of the other devices 70, 82, 84. For example, the healthcare professional may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 generally illustrated in FIG. 5 also includes an apparatus control 160 for the healthcare professional to view and/or to control information regarding the treatment device 70. The apparatus control 160 may take the form of a portion or region of the overview display 120, as is generally illustrated in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99*b*. The apparatus status display 162 may indicate whether the treatment device 70 is currently communicating with the patient interface 50. The apparatus status display 162 may present other current and/or historical information regarding the status of the treatment device 70.

The apparatus control 160 may include an apparatus setting control 164 for the healthcare professional to adjust or control one or more aspects of the treatment device 70. The apparatus setting control 164 may cause the assistant interface 94 to generate and/or to transmit an apparatus control signal 99 (e.g., which may be referred to as treatment plan input, as described) for changing an operating parameter and/or one or more characteristics of the treatment device 70, (e.g., a pedal radius setting, a resistance setting, a target RPM, other suitable characteristics of the treatment device 70, or a combination thereof).

The apparatus setting control 164 may include a mode button 166 and a position control 168, which may be used in conjunction for the healthcare professional to place an actuator 78 of the treatment device 70 in a manual mode, after which a setting, such as a position or a speed of the actuator 78, can be changed using the position control 168. The mode button 166 may provide for a setting, such as a position, to be toggled between automatic and manual modes.

In some embodiments, one or more settings may be adjustable at any time, and without having an associated auto/manual mode. In some embodiments, the healthcare professional may change an operating parameter of the treatment device 70, such as a pedal radius setting, while the patient is actively using the treatment device 70. Such "on the fly" adjustment may or may not be available to the patient using the patient interface 50.

In some embodiments, the apparatus setting control 164 may allow the healthcare professional to change a setting that cannot be changed by the patient using the patient interface 50. For example, the patient interface 50 may be precluded from changing a preconfigured setting, such as a height or a tilt setting of the treatment device 70, whereas the apparatus setting control 164 may provide for the healthcare professional to change the height or tilt setting of the treatment device 70.

The example overview display 120 generally illustrated in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one.

In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as is generally illustrated in FIG. 5. The patient communications control 170 may take other forms, such as a separate screen or a popup window.

The audio and/or audiovisual communications may be processed and/or directed by the assistant interface 94 and/or by another device or devices, such as a telephone system, or a videoconferencing system used by the healthcare professional while the healthcare professional uses the assistant interface 94. Alternatively or additionally, the audio and/or audiovisual communications may include communications with a third party. For example, the system 10 may enable the healthcare professional to initiate a 3-way conversation regarding use of a particular piece of hardware or software, with the patient and a subject matter expert, such as a healthcare professional or a specialist. The example patient communications control 170 generally illustrated in FIG. 5 includes call controls 172 for the healthcare professional to use in managing various aspects of the audio or audiovisual communications with the patient. The call controls 172 include a disconnect button 174 for the healthcare professional to end the audio or audiovisual communications session. The call controls 172 also include a mute button 176 to temporarily silence an audio or audiovisual signal from the assistant interface 94. In some embodiments, the call controls 172 may include other features, such as a hold button (not shown).

The call controls 172 also include one or more record/playback controls 178, such as record, play, and pause buttons to control, with the patient interface 50, recording and/or playback of audio and/or video from the teleconference session. The call controls 172 also include a video feed display 180 for presenting still and/or video images from the patient interface 50, and a self-video display 182 showing the current image of the healthcare professional using the assistant interface 94. The self-video display 182 may be presented as a picture-in-picture format, within a section of the video feed display 180, as is generally illustrated in FIG. 5. Alternatively or additionally, the self-video display 182 may be presented separately and/or independently from the video feed display 180.

The example overview display 120 generally illustrated in FIG. 5 also includes a third party communications control 190 for use in conducting audio and/or audiovisual communications with a third party. The third party communications control 190 may take the form of a portion or region of the overview display 120, as is generally illustrated in FIG. 5. The third party communications control 190 may take other forms, such as a display on a separate screen or a popup window.

The third party communications control 190 may include one or more controls, such as a contact list and/or buttons or controls to contact a third party regarding use of a particular piece of hardware or software, e.g., a subject matter expert, such as a healthcare professional or a specialist. The third party communications control 190 may include conference calling capability for the third party to simultaneously communicate with both the healthcare professional via the assistant interface 94, and with the patient via the patient interface 50. For example, the system 10 may provide for the healthcare professional to initiate a 3-way conversation with the patient and the third party.

Figure 6:
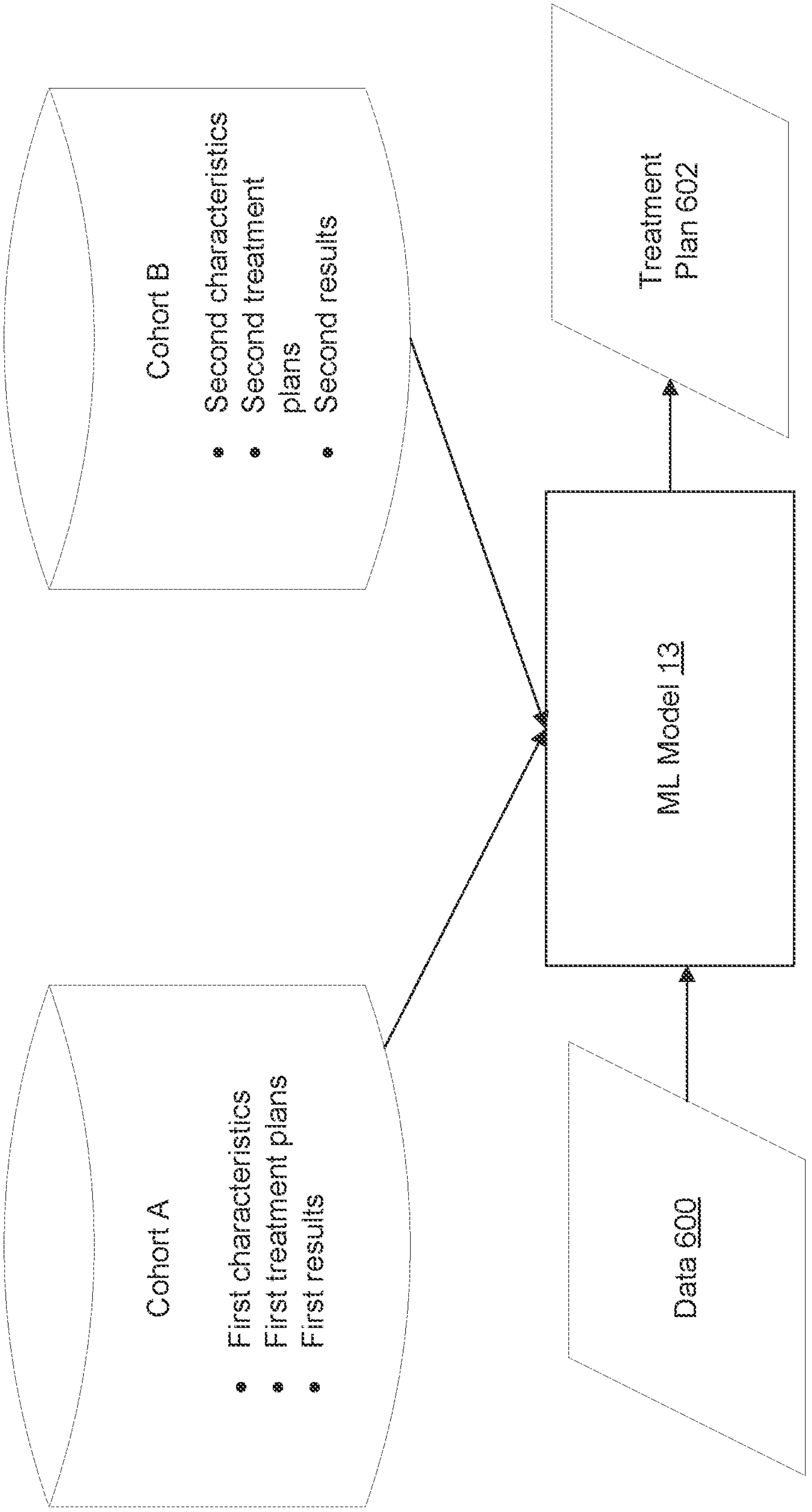
FIG. 6 generally illustrates an example block diagram of training a machine learning model to output, based on data pertaining to the patient, a treatment plan for the patient according to the principles of the present disclosure.

FIG. 6 generally illustrates an example block diagram of training a machine learning model 13 to output, based on data 600 pertaining to the patient, a treatment plan 602 for the patient according to the present disclosure. Data pertaining to other patients may be received by the server 30. The other patients may have used various treatment devices to perform treatment plans.

The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the treatment device 70 for 30 minutes 5 times a week for 3 weeks, wherein values for the properties, configurations, and/or settings of the treatment device 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan 602. In some embodiments, the machine learning model 13 may be trained to output one or more excluded treatment plans that should not be performed by the new patient.

Figure 7:
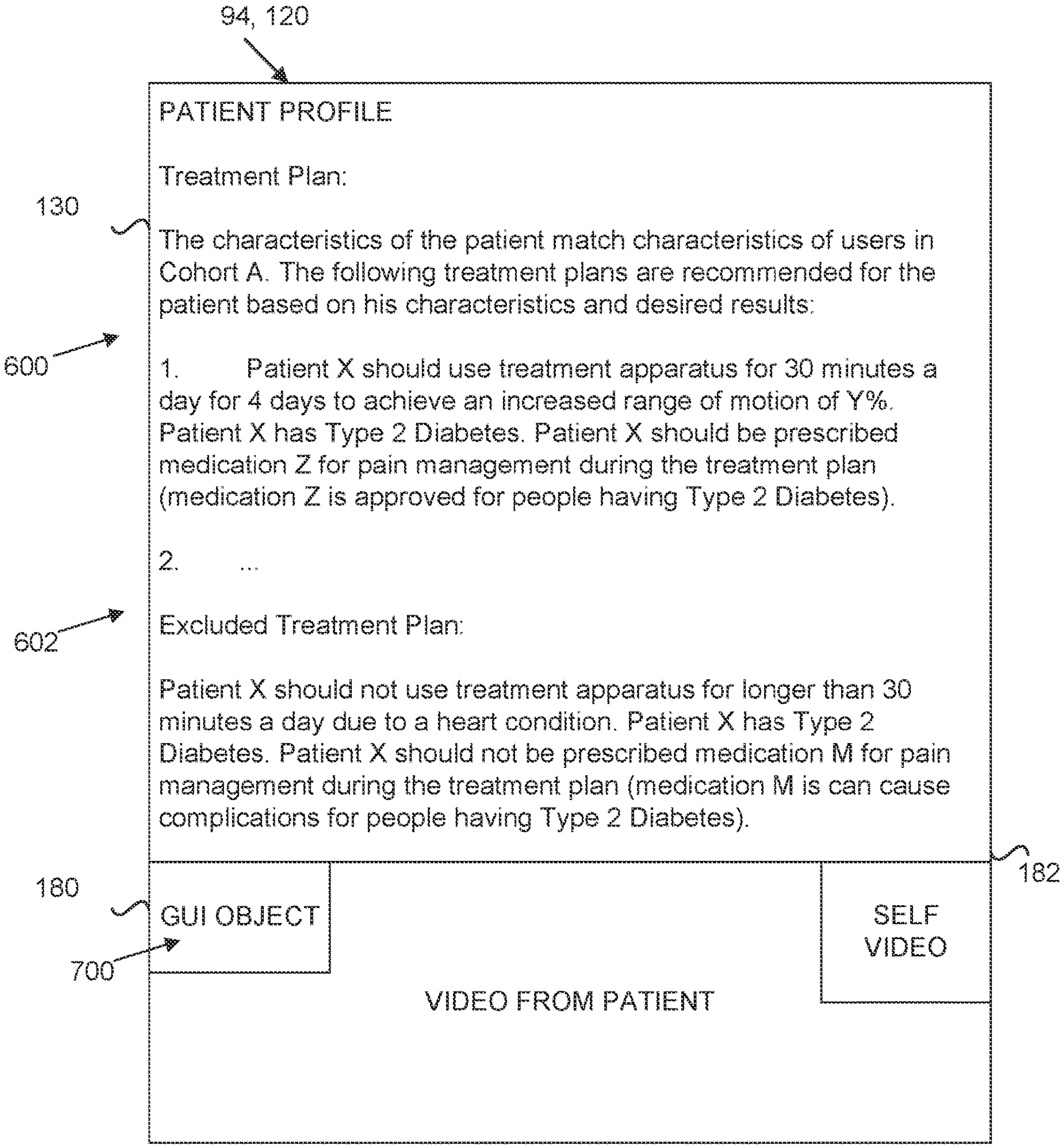
FIG. 7 generally illustrates an embodiment of an overview display of the assistant interface presenting recommended treatment plans and excluded treatment plans in real-time during a telemedicine session according to the principles of the present disclosure.

FIG. 7 generally illustrates an embodiment of an overview display 120 of the assistant interface 94 presenting recommended treatment plans and excluded treatment plans in real-time during a telemedicine session according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

The healthcare professional using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the healthcare professional to share, in real-time or near real-time during the telemedicine session, the recommended treatment plans and/or the excluded treatment plans with the patient on the patient interface 50. The healthcare professional may select the GUI object 700 to share the recommended treatment plans and/or the excluded treatment plans. As depicted, another portion of the overview display 120 includes the patient profile display 130.

The patient profile display 130 is presenting two example recommended treatment plans 600 and one example excluded treatment plan 602. As described herein, the treatment plans may be recommended in view of characteristics of the patient being treated. To generate the recommended treatment plans 600 the patient should follow to achieve a desired result, a pattern between the characteristics of the patient being treated and a cohort of other people who have used the treatment device 70 to perform a treatment plan may be matched by one or more machine learning models 13 of the artificial intelligence engine 11. Each of the recommended treatment plans may be generated based on different desired results.

For example, as depicted, the patient profile display 130 presents "The characteristics of the patient match characteristics of uses in Cohort A. The following treatment plans are recommended for the patient based on his characteristics and desired results." Then, the patient profile display 130 presents recommended treatment plans from cohort A, and each treatment plan provides different results.

As depicted, treatment plan "A" indicates "Patient X should use treatment device for 30 minutes a day for 4 days to achieve an increased range of motion of Y %; Patient X has Type 2 Diabetes; and Patient X should be prescribed medication Z for pain management during the treatment plan (medication Z is approved for people having Type 2 Diabetes)." Accordingly, the treatment plan generated achieves increasing the range of motion of Y %. As may be appreciated, the treatment plan also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome. This specific example and all such examples elsewhere herein are not intended to limit in any way the generated treatment plan from recommending multiple medications, or from handling the acknowledgement, view, diagnosis and/or treatment of comorbid conditions or diseases.

Recommended treatment plan "B" may specify, based on a different desired result of the treatment plan, a different treatment plan including a different treatment protocol for a treatment device, a different medication regimen, etc.

As depicted, the patient profile display 130 may also present the excluded treatment plans 602. These types of treatment plans are shown to the healthcare professional using the assistant interface 94 to alert the healthcare professional not to recommend certain portions of a treatment plan to the patient. For example, the excluded treatment plan could specify the following: "Patient X should not use treatment device for longer than 30 minutes a day due to a heart condition; Patient X has Type 2 Diabetes; and Patient X should not be prescribed medication M for pain management during the treatment plan (in this scenario, medication M can cause complications for people having Type 2 Diabetes). Specifically, the excluded treatment plan points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

The healthcare professional may select the treatment plan for the patient on the overview display 120. For example, the healthcare professional may use an input peripheral (e.g., mouse, touchscreen, microphone, keyboard, etc.) to select from the treatment plans 600 for the patient. In some embodiments, during the telemedicine session, the healthcare professional may discuss the pros and cons of the recommended treatment plans 600 with the patient.

In any event, the healthcare professional may select the treatment plan for the patient to follow to achieve the desired result. The selected treatment plan may be transmitted to the patient interface 50 for presentation. The patient may view the selected treatment plan on the patient interface 50. In some embodiments, the healthcare professional and the patient may discuss during the telemedicine session the details (e.g., treatment protocol using treatment device 70, diet regimen, medication regimen, etc.) in real-time or in near real-time. In some embodiments, the server 30 may control, based on the selected treatment plan and during the telemedicine session, the treatment device 70 as the user uses the treatment device 70.

Figure 8:
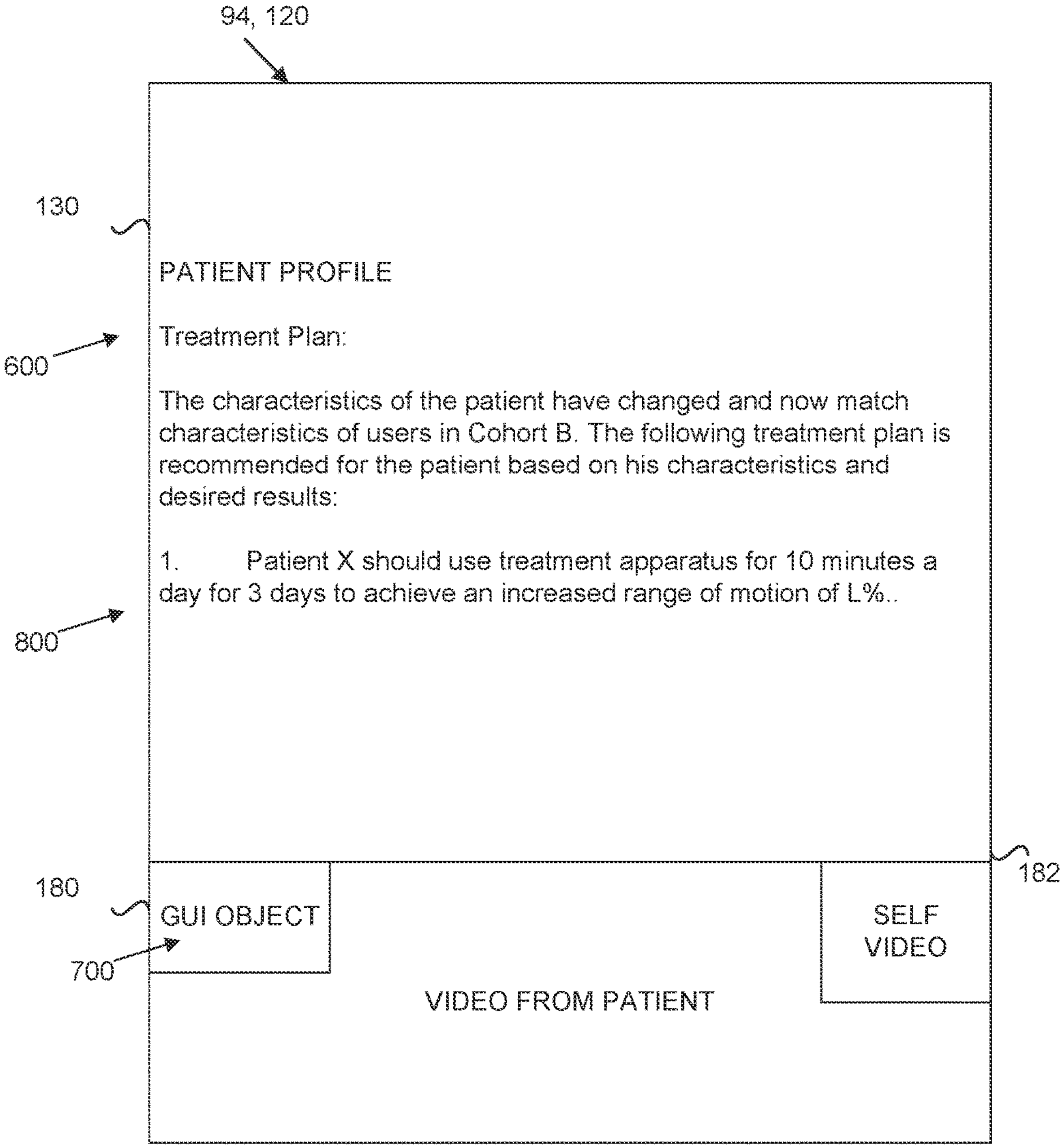
FIG. 8 generally illustrates an embodiment of the overview display of the assistant interface presenting, in real-time during a telemedicine session, recommended treatment plans that have changed as a result of patient data changing according to the principles of the present disclosure.

FIG. 8 generally illustrates an embodiment of the overview display 120 of the assistant interface 94 presenting, in real-time during a telemedicine session, recommended treatment plans that have changed as a result of patient data changing according to the present disclosure. As may be appreciated, the treatment device 70 and/or any computing device (e.g., patient interface 50) may transmit data while the patient uses the treatment device 70 to perform a treatment plan. The data may include updated characteristics of the patient and/or other treatment data. For example, the updated characteristics may include new performance information and/or measurement information. The performance information may include a speed of a portion of the treatment device 70, a range of motion achieved by the patient, a force exerted on a portion of the treatment device 70, a heartrate of the patient, a blood pressure of the patient, a respiratory rate of the patient, and so forth.

In some embodiments, the data received at the server 30 may be input into the trained machine learning model 13, which may determine that the characteristics indicate the patient is on track for the current treatment plan. Determining the patient is on track for the current treatment plan may cause the trained machine learning model 13 to adjust a parameter of the treatment device 70. The adjustment may be based on a next step of the treatment plan to further improve the performance of the patient.

In some embodiments, the data received at the server 30 may be input into the trained machine learning model 13, which may determine that the characteristics indicate the patient is not on track (e.g., behind schedule, not able to maintain a speed, not able to achieve a certain range of motion, is in too much pain, etc.) for the current treatment plan or is ahead of schedule (e.g., exceeding a certain speed, exercising longer than specified with no pain, exerting more than a specified force, etc.) for the current treatment plan.

The trained machine learning model 13 may determine that the characteristics of the patient no longer match the characteristics of the patients in the cohort to which the patient is assigned. Accordingly, the trained machine learning model 13 may reassign the patient to another cohort that includes qualifying characteristics the patient's characteristics. As such, the trained machine learning model 13 may select a new treatment plan from the new cohort and control, based on the new treatment plan, the treatment device 70.

In some embodiments, prior to controlling the treatment device 70, the server 30 may provide the new treatment plan 800 to the assistant interface 94 for presentation in the patient profile 130. As depicted, the patient profile 130 indicates "The characteristics of the patient have changed and now match characteristics of uses in Cohort B. The following treatment plan is recommended for the patient based on his characteristics and desired results." Then, the patient profile 130 presents the new treatment plan 800 ("Patient X should use the treatment device for 10 minutes a day for 3 days to achieve an increased range of motion of L %." The healthcare professional may select the new treatment plan 800, and the server 30 may receive the selection. The server 30 may control the treatment device 70 based on the new treatment plan 800. In some embodiments, the new treatment plan 800 may be transmitted to the patient interface 50 such that the patient may view the details of the new treatment plan 800.

In some embodiments, while the patient is using the treatment device 70 to perform the treatment plan, the server 30 may receive treatment data pertaining to a patient while the patient is using the treatment device 70 to perform the treatment plan. The patient may include a user or person using the treatment device 70 to perform various exercises. In some embodiments, the server 30 may receive the treatment data during a telemedicine session. Additionally, or alternatively, during the telemedicine session, the patient may use the treatment device 70.

As described, the treatment data may include various characteristics of the patient, various measurement information pertaining to the patient while the patient uses the treatment device 70, various performance measurement information pertaining to the use of the treatment device 70 by the patient, various characteristics of the treatment device 70, the treatment plan, other suitable data, or a combination thereof.

In some embodiments, while the patient uses the treatment device 70 to perform the treatment plan, at least some of the treatment data may include the sensor data 136 from one or more of the external sensors 82, 84, 86, and/or from one or more internal sensors 76 of the treatment device 70. In some embodiments, at least some of the treatment data may include sensor data from one or more sensors of one or more wearable devices worn by the patient while using the treatment device 70. The one or more wearable devices may include a watch, a bracelet, a necklace, a headband, a wristband, an ankle band, any other suitable band, eyeglasses or eyewear (such as, without limitation, Google Glass) a chest or torso strap, a device configured to be worked on, attached to, or communicatively coupled to a body, and the like. While the user is using the treatment device 70, the one or more wearable devices may be configured to monitor, with respect to the user, a heartrate, a temperature, a blood pressure, an eye dilation, one or more vital signs, one or more metabolic markers, biomarkers, and the like.

In some embodiments, the server 30 may be configured to receive URD pertaining to the patient. The URD may include at least baseline data (e.g., or previously captured or measured data) for the patient during engagement, by the patient, in at least one activity. The at least one activity may include walking, running, climbing, jumping, cycling, throwing, rolling, squatting, swimming, rowing, any other suitable activity or isometric, isotonic, plyometric, aerobic, anaerobic, or other exercise, or a combination thereof (e.g., including assisted activities (e.g., such as using a treadmill and the like) or unassisted activities). In some embodiments, the at least one activity may include at least one activity that the patient previously engaged in while using the treatment device 70. In some embodiments, the at least one activity may include at least one activity that the patient previously engaged in while not using the treatment device 70.

In some embodiments, while the patient engages in at least one activity, the server 30 may be configured to receive alignment data associated with the patient. The alignment data may include at least one of relative position data associated with at least one body part associated with the patient (e.g., which may indicate a position of the patient or a portion of the patient, such as a body part of the patient, relative to a reference point or plane), relative angle data associated with at least one body part associated with the patient (e.g., which may indicate an angle of the at least one body part of the patient relative to a reference point or plane), lateral motion data associated with at least one body part associated with the patient, pressure data associated with at least one body part associated with the patient (e.g., which may indicate an amount of pressure the body part of the patient is exerting on a component of the treatment device or other suitable device, mechanism, sensor, and the like), rotational motion data associated with at least one body part associated with the patient, other suitable alignment data, or a combination thereof.

In some embodiments, server 30 may identify, based on at least the treatment data, the URD, and the alignment data, at least one alignment characteristic associated with the patient. The at least one alignment characteristic may include one or more alignment delta values associated with at least one alignment aspect of the patient, one or more alignment scores associated with at least one alignment aspect of the patient, one or more alignment performance values associated with at least one alignment aspect of the patient, other suitable alignment characteristics associated with the patient, or a combination thereof.

The server 30 may determine a difference between the pedal pressure measurement corresponding to the at least one aspect of the treatment data and the pedal pressure measurement corresponding to the at least one aspect of the URD. The server 30 may generate delta information based on the difference between the at least one aspect of the treatment data and the at least one aspect of the URD.

The server 30 may generate, based on the delta information and the at least one aspect of the alignment data, the alignment delta value. For example, the server 30 may determine, based on the delta information, an expected alignment value for the at least one body part of the patient. The server 30 may determine, based on a difference between the expected alignment value and an alignment value corresponding to the at least one aspect of the alignment data, the alignment delta value. It should be understood that the server 30 may be configured to generate the alignment delta value using any suitable techniques in addition to or instead of those described herein. Additionally, or alternatively, using any suitable technique in addition to or instead of those described herein, the server 30 may be configured to identify any aspect of the at least one alignment characteristic of the patient.

In some embodiments, server 30 may provide, to a healthcare professional associated with the patient, the treatment data, the URD, the alignment data, and/or the at least one alignment characteristic. The server 30 may communicate with an interface, such as the assistant interface 94 or another suitable interface. The assistant interface 94 may be configured to receive the information associated with the at least one alignment characteristic. For example, the server 30 may store, at a memory, such as the memory 38 or other suitable memory, the treatment data, the URD, the alignment data, and/or the at least one alignment characteristic. The assistant interface 94 may be configured to retrieve, from the memory 38 or other suitable memory, the treatment data, the URD, the alignment data, and/or the at least one alignment characteristic.

The healthcare professional may use at least one artificial intelligence engine (e.g., such as the artificial intelligence engine 11 or other suitable artificial intelligence engine) configured to use at least one machine learning model (e.g., such as the machine learning model 13 or other suitable machine learning model) that generates, based on the at least one alignment characteristic, treatment plan input. The treatment plan input may include information indicating at least one alignment issue of the patient, information indicating at least one modification to the treatment plan, other suitable information indicating other suitable aspects of an analysis performed by the healthcare professional, or a combination thereof.

In some embodiments, the server 30 may modify at least one aspect of the treatment plan in response to receiving, from the healthcare professional, the treatment plan input, wherein the treatment plan input includes at least one modification to the at least one aspect of the treatment plan. For example, in some embodiments, the server 30 may be configured to perform, in response to receiving treatment plan input indicating at least one treatment action, the at least one treatment action indicated by the treatment plan input. The treatment plan input may also indicate the one or more alignment issues of the patient identified by the healthcare professional. The at least one treatment action may correspond to the one or more alignment issues of the patient and may include modifying at least one aspect of the treatment plan, controlling (e.g., while the patient uses the treatment device) at least one aspect of the treatment device 70, generating (e.g., based on the treatment plan input) a notification, transmitting (e.g., to at least one of the patient and an agent of the patient, such as a primary care physician, a physical therapist, a caregiver, any medical, healthcare, therapeutic, personal trainer or other professional, and/or other suitable agent of the user) the notification, any other suitable treatment action, or a combination thereof.

In some embodiments, transmitting the notification may include transmitting the notification to one or more mobile devices associated with the patient or the agent of the patient, to electronic mail addresses of the patient or the agent of the patient, to applications associated with the use of the treatment device 70 (including, without limitation, transmission to an application via an API (application user interface), to displays of the treatment device 70, or to other suitable locations. The notification may include at least an indication of the alignment issues associated with the patient and/or the at least one treatment action. Additionally, or alternatively, the notification may comprise an aspect that includes sound, an aspect that includes a visual display or projection, any other suitable aspect or sensorial aspect, or a combination thereof.

If the at least one treatment action includes modifying one or more aspects of the treatment plan and/or one or more characteristics of the treatment device 70, the server 30 may modify the one or more aspects of the treatment plan and/or the one or more characteristics of the treatment device 70. For example, the at least one treatment action may indicate an increase or decrease in the resistance setting of the treatment device 70, or other suitable modification to the one or more characteristics of the treatment device 70. Additionally, or alternatively, the at least one treatment action may indicate an increase or decrease in an amount of time the patient is required to use the treatment device according to the treatment plan, or other suitable modifications to the treatment plan.

The server 30 may be configured to provide, at the overview display 120, the at least one alignment characteristic and/or the at least one alignment issue. For example, the server 30 may store the at least one alignment characteristic and/or the at least one alignment issue for access by the overview display 120 and/or may communicate the at least one alignment characteristic and/or the at least one alignment issue to the overview display 120. In some embodiments, the server 30 may provide the at least one alignment characteristic and/or the at least one alignment issue to the patient profile display 130 or to other suitable section, portion, or component of the overview display 120, or to any other suitable display or interface.

In some embodiments, the server 30 may be configured to determine, using at least the at least one alignment characteristic, whether the at least one alignment characteristic correlates with at least one secondary condition of the patient. The server 30 may write to the memory 38 or other suitable memory, the at least one alignment characteristic. The server 30 may use the artificial intelligence engine 11, using the at least one machine learning model 13, to generate, using the at least one alignment characteristic, at least one of secondary condition output prediction.

In some embodiments, the artificial intelligence engine 11 may be configured to use the at least one machine learning model 13 to generate, further using secondary condition information associated with other patients, the at least one of secondary condition output prediction. At least some of the other patients may be associated with a cohort to which the patient belongs; alternatively, all of the other patients may be associated with the cohort of which the patient belongs; further alternatively, the other patients may be associated with other cohorts; or the other patients may not be associated with any identified cohort. In some embodiments, the other patients may have characteristics similar to those of the patient. In some embodiments, measurements pertaining to the other patients may include measurements similar to the at least one measurement pertaining to the patient.

The at least one secondary condition output prediction generated by the at least one machine learning model 13 may indicate one or more secondary conditions that may be associated with the patient. The server 30 may receive, from the artificial intelligence engine 11, the at least one secondary condition output prediction.

In some embodiments, server 30 may, in response to a determination that the at least one alignment characteristic is correlated with the at least one secondary condition of the patient, generate secondary condition information indicating at least the secondary condition. The server 30 may write, to the memory 38 or other suitable memory, for access at the computing device of the healthcare professional, the secondary condition information and/or the secondary condition output prediction.

In some embodiments, the server 30 may modify at least one aspect of the treatment plan in response to receiving, from a healthcare professional, treatment plan input, as described herein. The treatment plan input may include at least one modification to the at least one aspect of the treatment plan. The treatment plan input may be generated, by the healthcare professional, based on the secondary condition information.

Figure 9:
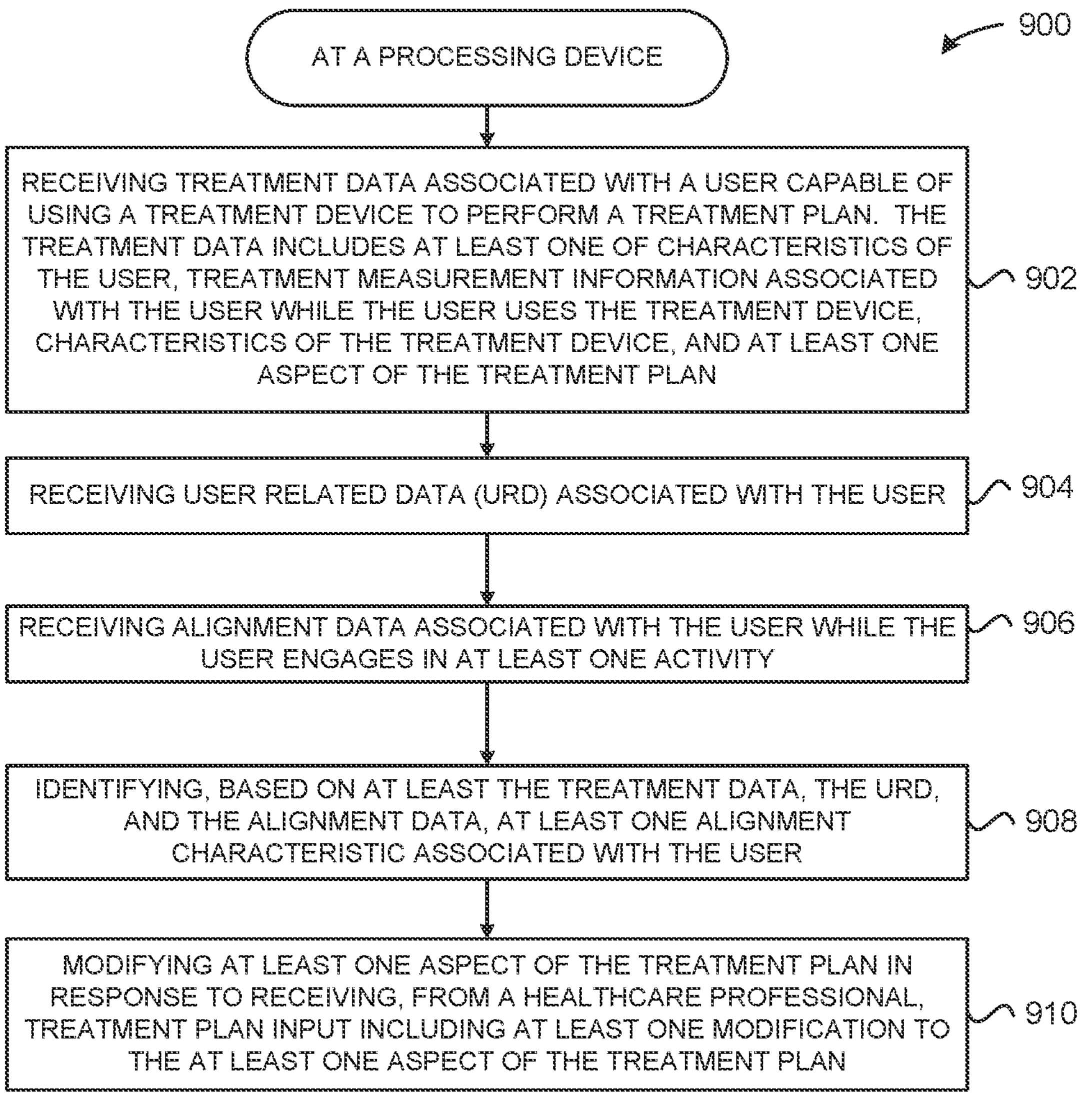
FIG. 9 is a flow diagram generally illustrating a method for detecting, based on treatment data received while a user uses the treatment device of FIG. 2, joint misalignment of the user according to the principles of the present disclosure.

FIG. 9 is a flow diagram generally illustrating a method 900 for detecting, based on treatment data received while a user uses a treatment device, joint misalignment of the user of the user, according to the present disclosure. The method 900 is performed by processing logic that may include hardware (circuitry, dedicated logic, etc.), software (such as is run on a general-purpose computer system or a dedicated machine), or a combination of both. The method 900 and/or each of its individual functions, routines, subroutines, or operations may be performed by one or more processors of a computing device (e.g., any component of FIG. 1, such as server 30 executing the artificial intelligence engine 11). In some embodiments, the method 900 may be performed by a single processing thread. Alternatively, the method 900 may be performed by two or more processing threads, each thread implementing one or more individual functions, routines, subroutines, or operations of the methods.

For simplicity of explanation, the method 900 is depicted and described as a series of operations. However, operations in accordance with this disclosure can occur in various orders and/or concurrently, and/or with other operations not presented and described herein. For example, the operations depicted in the method 900 may occur in combination with any other operation of any other method disclosed herein. Furthermore, not all illustrated operations may be required to implement the method 900 in accordance with the disclosed subject matter. In addition, those skilled in the art will understand and appreciate that the method 900 could alternatively be represented as a series of interrelated states via a state diagram or events.

At 902, the processing device may receive treatment data associated with a user capable of using a treatment device, such as the treatment device 70, to perform a treatment plan. The treatment data may include at least one of characteristics of the user, treatment measurement information associated with the user while the user uses the treatment device 70, characteristics of the treatment device 70, and at least one aspect of the treatment plan.

At 904, while the user engages in at least one activity, the processing device may receive URD associated with the user. At 906, the processing device may receive alignment data associated with the user.

At 908, the processing device may identify, based on at least the treatment data, the URD, and the alignment data, at least one alignment characteristic associated with the user.

At 910, the processing device may modify at least one aspect of the treatment plan in response to receiving, from a healthcare professional, treatment plan input including at least one modification to the at least one aspect of the treatment plan.

Figure 10:
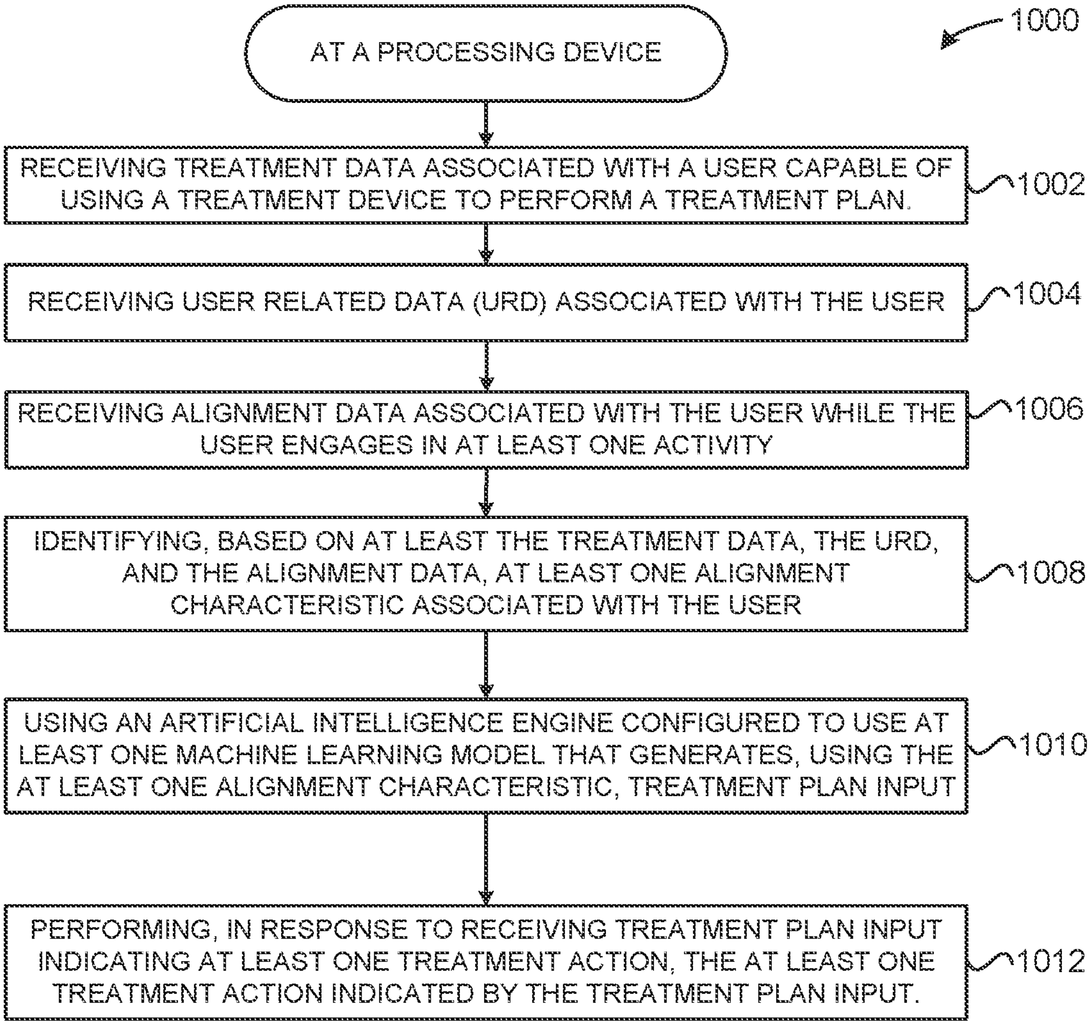
FIG. 10 is a flow diagram generally illustrating an alternative method for detecting, based on treatment data received while a user uses the treatment device of FIG. 2, joint misalignment of the user of the user according to the principles of the present disclosure.

FIG. 10 is a flow diagram generally illustrating an alternative method 1000 for detecting, based on treatment data received while a user uses a treatment device, joint misalignment of the user, according to the present disclosure. Method 1000 includes operations performed by processors of a computing device (e.g., any component of FIG. 1, such as server 30 executing the artificial intelligence engine 11). In some embodiments, one or more operations of the method 1000 are implemented in computer instructions stored on a memory device and executed by a processing device. The method 1000 may be performed in the same or a similar manner as described above in regard to method 900. The operations of the method 1000 may be performed in some combination with any of the operations of any of the methods described herein.

At 1002, to perform a treatment plan, the processing device may receive treatment data associated with a user capable of using a treatment device, such as the treatment device 70. The treatment data may include at least one of characteristics of the user, treatment measurement information associated with the user while the user uses the treatment device 70, characteristics of the treatment device 70, and at least one aspect of the treatment plan.

At 1004, while the user engages in at least one activity, the processing device may receive URD associated with the user. At 1006, the processing device may receive alignment data associated with the user.

At 1008, the processing device may identify, based on at least the treatment data, the URD, and the alignment data, at least one alignment characteristic associated with the user.

At 1010, the processing device may use an artificial intelligence engine (e.g., such as the artificial intelligence engine 11) configured to use at least one machine learning model (e.g., such as the machine learning model 13) that generates, using the at least one alignment characteristic, treatment plan input.

At 1012, the processing device may perform, in response to receiving treatment plan input indicating at least one treatment action, the at least one treatment action indicated by the treatment plan input.

Figure 11:
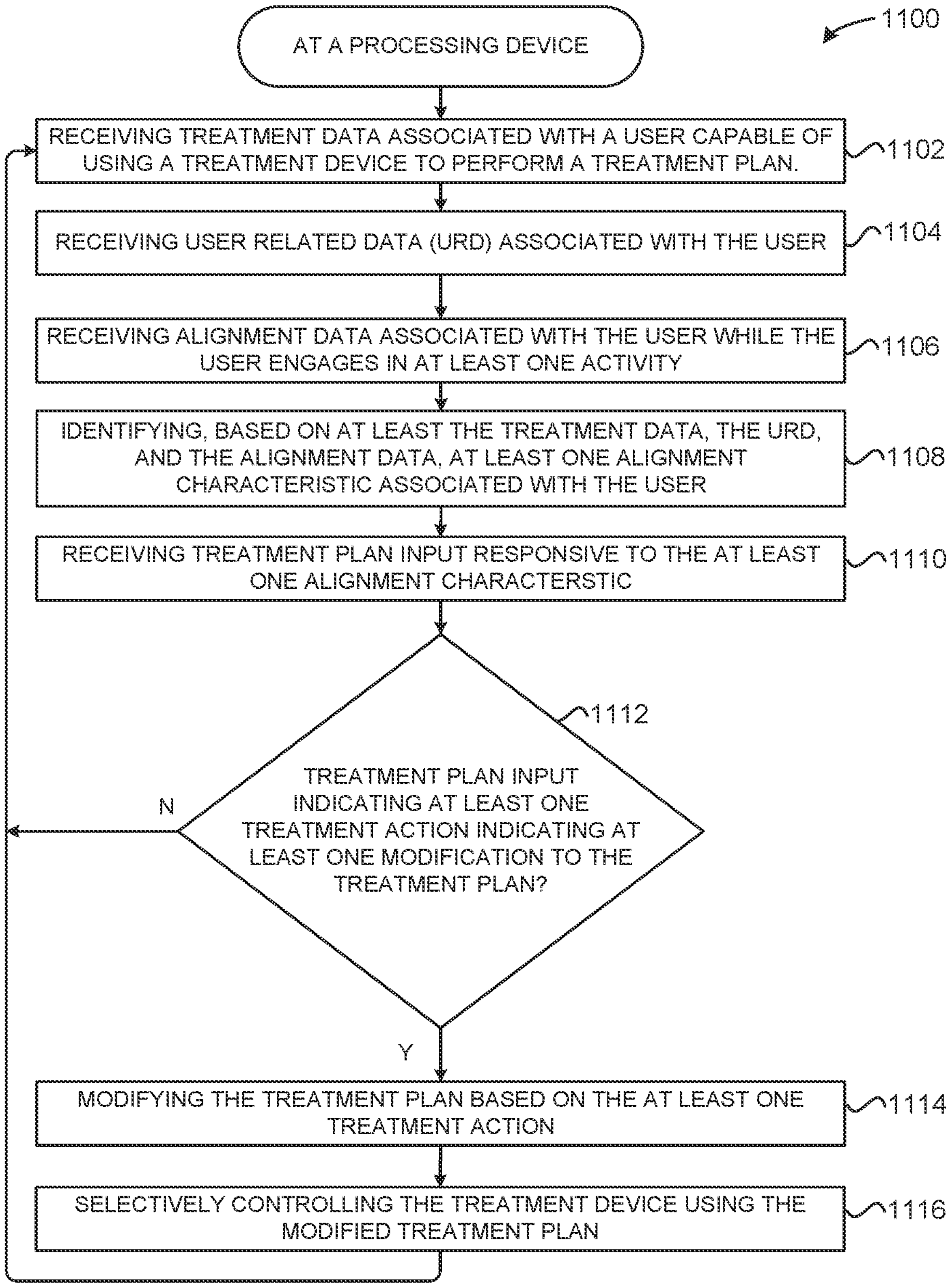
FIG. 11 is a flow diagram generally illustrating an alternative method for detecting, based on treatment data received while a user uses the treatment device of FIG. 2, joint misalignment of the user of the user according to the principles of the present disclosure.

FIG. 11 is a flow diagram generally illustrating an alternative method 1100 for detecting, based on treatment data received while a user uses a treatment device, joint misalignment of the user, according to the present disclosure. Method 1100 includes operations performed by processors of a computing device (e.g., any component of FIG. 1, such as server 30 executing the artificial intelligence engine 11). In some embodiments, one or more operations of the method 1100 are implemented in computer instructions stored on a memory device and executed by a processing device. The method 1100 may be performed in the same or a similar manner as described above in regard to method 900 and/or method 1000. The operations of the method 1100 may be performed in some combination with any of the operations of any of the methods described herein.

At 1102, to perform a treatment plan, the processing device may receive treatment data associated with a user capable of using a treatment device, such as the treatment device 70. The treatment data may include at least one of characteristics of the user, treatment measurement information associated with the user while the user uses the treatment device 70, characteristics of the treatment device 70, and at least one aspect of the treatment plan.

At 1104, while the user engages in at least one activity, the processing device may receive URD associated with the user. At 1106, the processing device may receive alignment data associated with the user.

At 1108, the processing device may identify, based on at least the treatment data, the URD, and the alignment data, at least one alignment characteristic associated with the user.

At 1110, the processing device may receive treatment plan input responsive to the at least one alignment characteristic. At 1112, the processing device may determine whether the treatment plan input indicates at least one treatment action indicating at least one modification to the treatment plan. If the processing device determines that the treatment plan input does not indicate at least one treatment action indicating at least one modification to the treatment plan, the processing device may continue at 1102. Conversely, if the processing device determines that the treatment plan input indicates at least one treatment action indicating at least one modification to the treatment plan, the processing device may continue at 1114.

At 1114, the processing device may modify the treatment plan based on the at least one treatment action. At 1116, using the modified treatment plan, the processing device may selectively control the treatment device 70.

Figure 12:
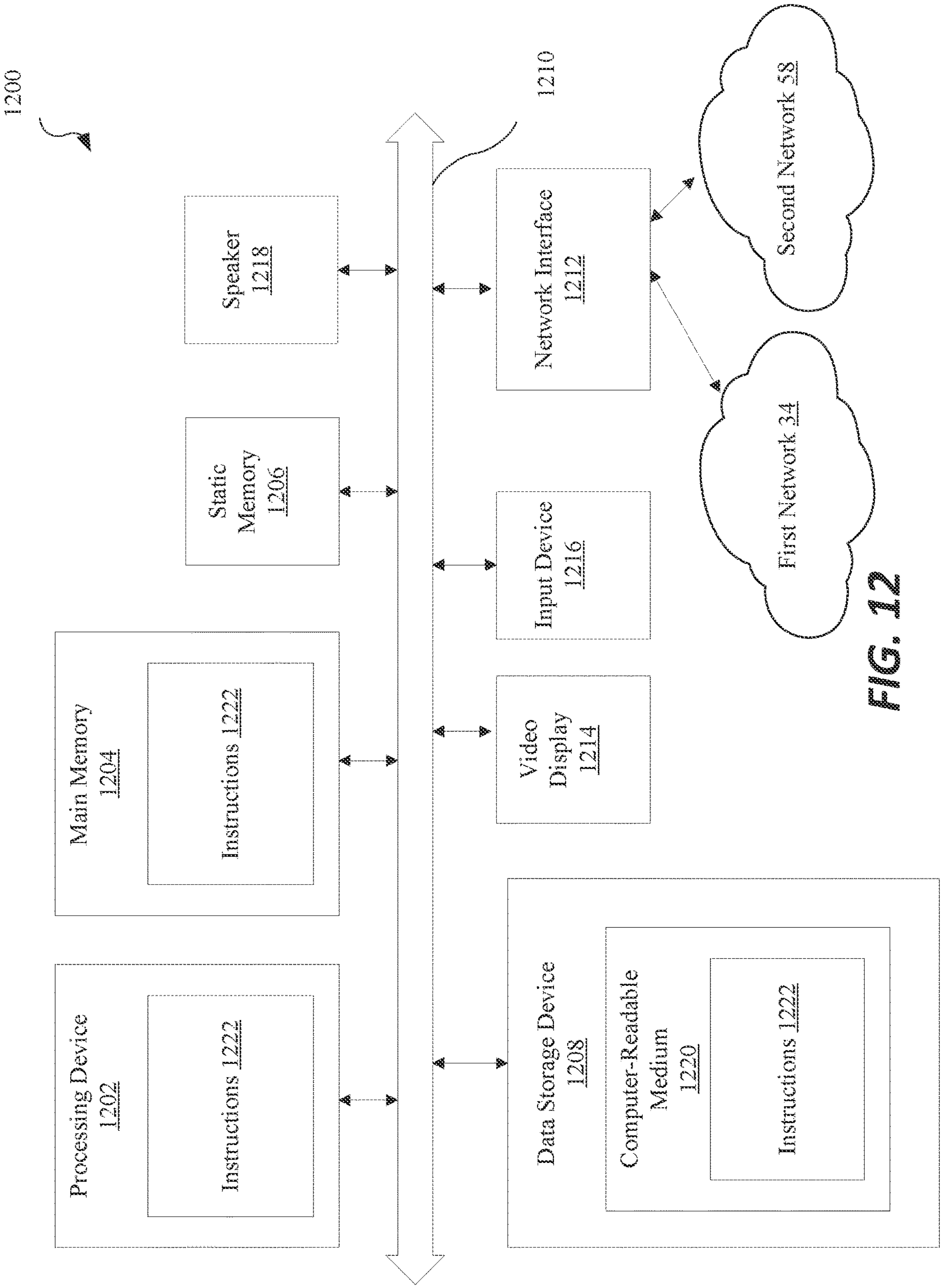
FIG. 12 generally illustrates a computer system according to the principles of the present disclosure.

FIG. 12 generally illustrates an example computer system 1200 which can perform any one or more of the methods described herein, in accordance with one or more aspects of the present disclosure. In one example, computer system 1200 may include a computing device and correspond to the assistant interface 94, reporting interface 92, supervisory interface 90, clinician interface 20, server 30 (including the AI engine 11), patient interface 50, ambulatory sensor 82, goniometer 84, treatment device 70, pressure sensor 86, or any suitable component of FIG. 1. The computer system 1200 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network.

The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1200 includes a processing device 1202, a main memory 1204 (e.g., read-only memory (ROM), flash memory, solid state drives (SSDs), dynamic random access memory (DRAM) such as synchronous DRAM (SDRAM)), a static memory 1206 (e.g., flash memory, solid state drives (SSDs), static random access memory (SRAM)), and a data storage device 1208, which communicate with each other via a bus 1210.

Processing device 1202 represents one or more general-purpose processing devices such as a microprocessor, central processing unit, or the like. More particularly, the processing device 1202 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1200 may further include a network interface device 1212. The computer system 1200 also may include a video display 1214 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1216 (e.g., a keyboard and/or a mouse or a gaming-like control), and one or more speakers 1218 (e.g., a speaker). In one illustrative example, the video display 1214 and the input device(s) 1216 may be combined into a single component or device (e.g., an LCD touch screen).

The data storage device 1216 may include a computer-readable medium 1220 on which the instructions 1222 embodying any one or more of the methods, operations, or functions described herein is stored. The instructions 1222 may also reside, completely or at least partially, within the main memory 1204 and/or within the processing device 1202 during execution thereof by the computer system 1200. As such, the main memory 1204 and the processing device 1202 also constitute computer-readable media. The instructions 1222 may further be transmitted or received over a network via the network interface device 1212.

While the computer-readable storage medium 1220 is generally illustrated in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A method comprising: receiving treatment data associated with a user capable of using a treatment device to perform a treatment plan, wherein the treatment data comprises at least one of characteristics of the user, treatment measurement information associated with the user while the user uses the treatment device, one or more characteristics of the treatment device, and at least one aspect of the treatment plan; receiving user related data (URD) associated with the user; receiving alignment data associated with the user while the user engages in at least one activity; identifying, based on at least the treatment data, the URD, and the alignment data, at least one alignment characteristic associated with the user; and modifying at least one aspect of the treatment plan in response to receiving, from a healthcare professional, treatment plan input including at least one modification to the at least one aspect of the treatment plan.

Clause 2. The method of clause 1, wherein the at least one activity includes at least one of using the treatment device and an activity other than using the treatment device.

Clause 3. The method of clause 1, wherein the healthcare professional uses at least one artificial intelligence engine configured to use at least one machine learning model that generates, based on the at least one alignment characteristic, the treatment plan input.

Clause 4. The method of clause 3, wherein the artificial intelligence engine is associated with at least one of the treatment device, a remotely located server computing device, and a computing device of a healthcare professional.

Clause 5. The method of clause 1, further comprising communicating with an interface, at a computing device of the healthcare professional, wherein the interface is configured to receive the information associated with the at least one alignment characteristic.

Clause 6. The method of clause 5, wherein the healthcare professional includes a human healthcare professional at least partially responsible for treatment of the user.

Clause 7. The method of clause 1, further comprising controlling, while the user uses the treatment device, and based on the modified the at least one of the at least one aspect and any other aspect of the treatment plan, the treatment device.

Clause 8. The method of clause 7, wherein the user uses the treatment device during a telemedicine session.

Clause 9. The method of clause 1, wherein the treatment measurement information includes, while the user uses the treatment device, at least one of a vital sign of the user, a respiration rate of the user, a heartrate of the user, a temperature of the user, an SpO2 measurement of the blood oxygen level of the user, and a blood pressure of the user.

Clause 10. The method of clause 1, wherein the alignment data includes at least one of relative position data associated with at least one body part associated with the user, relative angle data associated with at least one body part associated with the user, lateral motion data associated with at least one body part associated with the user, pressure data associated with at least one body part associated with the user; and rotational motion data associated with at least one body part associated with the user.

Clause 11. The method of clause 1, wherein at least some of the treatment data corresponds to at least some of the sensor data from a sensor associated with the treatment device.

Clause 12. The method of clause 1, wherein, while the user uses the treatment device, at least some of the treatment data corresponds to at least some of the sensor data from a sensor associated with a wearable device worn by the user.

Clause 13. The method of clause 1, wherein, while the user engages in the at least one activity, at least some of the alignment data corresponds to at least some sensor data from a one sensor associated with at least one wearable device worn by the user.

Clause 14. The method of clause 13, wherein the at least one wearable device includes at least one of a goniometer and a pedometer.

Clause 15. The method of clause 1, wherein, while the user engages in the at least one activity, at least some of the alignment data corresponds to at least some sensor data from at least one sensor associated with an image capturing device.

Clause 16. A tangible, non-transitory computer-readable medium storing instructions that, when executed, cause a processing device to: receive treatment data associated with a user capable of using a treatment device to perform a treatment plan, wherein the treatment data comprises at least one of characteristics of the user, treatment measurement information associated with the user while the user uses the treatment device, one or more characteristics of the treatment device, and at least one aspect of the treatment plan;

receive user related data (URD) associated with the user; receive alignment data associated with the user while the user engages in at least one activity; identify, based on at least the treatment data, the URD, and the alignment data, at least one alignment characteristic associated with the user; and modify at least one aspect of the treatment plan in response to receiving, from a healthcare professional, treatment plan input including at least one modification to the at least one aspect of the treatment plan.

Clause 17. The computer-readable medium of clause 16, wherein the at least one activity includes at least one of using the treatment device and an activity other than using the treatment device.

Clause 18. The computer-readable medium of clause 16, wherein the healthcare professional uses at least one artificial intelligence engine configured to use at least one machine learning model that generates, based on the at least one alignment characteristic, the treatment plan input.

Clause 19. The computer-readable medium of clause 18, wherein the artificial intelligence engine is associated with at least one of the treatment device, a remotely located server computing device, and a computing device of a healthcare professional.

Clause 20. The computer-readable medium of clause 16, wherein the instructions further cause the processor to communicate with an interface, at a computing device of the healthcare professional, wherein the interface is configured to receive the information associated with the at least one alignment characteristic.

Clause 21. The computer-readable medium of clause 20, wherein the healthcare professional includes a human healthcare professional at least partially responsible for treatment of the user.

Clause 22. The computer-readable medium of clause 16, wherein the instructions further cause the processor to control, while the user uses the treatment device, and based on the modified the at least one of the at least one aspect and any other aspect of the treatment plan, the treatment device.

Clause 23. The computer-readable medium of clause 22, wherein the user uses the treatment device during a telemedicine session.

Clause 24. The computer-readable medium of clause 16, wherein the treatment measurement information includes, while the user uses the treatment device, at least one of a vital sign of the user, a respiration rate of the user, a heartrate of the user, a temperature of the user, an SpO2 measurement of the blood oxygen level of the user, and a blood pressure of the user.

Clause 25. The computer-readable medium of clause 16, wherein the alignment data includes at least one of relative position data associated with at least one body part associated with the user, relative angle data associated with at least one body part associated with the user, lateral motion data associated with at least one body part associated with the user, pressure data associated with at least one body part associated with the user; and rotational motion data associated with at least one body part associated with the user.

Clause 26. The computer-readable medium of clause 16, wherein at least some of the treatment data corresponds to at least some of the sensor data from a sensor associated with the treatment device.

Clause 27. The computer-readable medium of cl clause 16, wherein, while the user uses the treatment device, at least some of the treatment data corresponds to at least some of the sensor data from a sensor associated with a wearable device worn by the user.

Clause 28. The computer-readable medium of clause 16, wherein, while the user engages in the at least one activity, at least some of the alignment data corresponds to at least some sensor data from a one sensor associated with at least one wearable device worn by the user.

Clause 29. The computer-readable medium of clause 28, wherein the at least one wearable device includes at least one of a goniometer and a pedometer.

Clause 30. The computer-readable medium of clause 16, wherein, while the user engages in the at least one activity, at least some of the alignment data corresponds to at least some sensor data from at least one sensor associated with an image capturing device.

Clause 31. A system comprising: a processor; and a memory including instructions that, when executed by the processor, cause the processor to: receive treatment data associated with a user capable of using a treatment device to perform a treatment plan, wherein the treatment data comprises at least one of characteristics of the user, treatment measurement information associated with the user while the user uses the treatment device, one or more characteristics of the treatment device, and at least one aspect of the treatment plan; receive user related data (URD) associated with the user; receive alignment data associated with the user while the user engages in at least one activity; identify, based on at least the treatment data, the URD, and the alignment data, at least one alignment characteristic associated with the user; and modify at least one aspect of the treatment plan in response to receiving, from a healthcare professional, treatment plan input including at least one modification to the at least one aspect of the treatment plan.

Clause 32. The system of clause 31, wherein the at least one activity includes at least one of using the treatment device and an activity other than using the treatment device.

Clause 33. The system of clause 31, wherein the healthcare professional uses at least one artificial intelligence engine configured to use at least one machine learning model that generates, based on the at least one alignment characteristic, the treatment plan input.

Clause 34. The system of clause 33, wherein the artificial intelligence engine is associated with at least one of the treatment device, a remotely located server computing device, and a computing device of a healthcare professional.

Clause 35. The system of clause 31, wherein the instructions further cause the processor to communicate with an interface, at a computing device of the healthcare professional, wherein the interface is configured to receive the information associated with the at least one alignment characteristic.

Clause 36. The system of clause 35, wherein the healthcare professional includes a human healthcare professional at least partially responsible for treatment of the user.

Clause 37. The system of clause 31, wherein the instructions further cause the processor to control, while the user uses the treatment device, and based on the modified the at least one of the at least one aspect and any other aspect of the treatment plan, the treatment device.

Clause 38. The system of clause 37, wherein the user uses the treatment device during a telemedicine session.

Clause 39. The system of clause 31, wherein the treatment measurement information includes, while the user uses the treatment device, at least one of a vital sign of the user, a respiration rate of the user, a heartrate of the user, a temperature of the user, an SpO2 measurement of the blood oxygen level of the user, and a blood pressure of the user.

Clause 40. The system of clause 31, wherein the alignment data includes at least one of relative position data associated with at least one body part associated with the user, relative angle data associated with at least one body part associated with the user, lateral motion data associated with at least one body part associated with the user, pressure data associated with at least one body part associated with the user; and rotational motion data associated with at least one body part associated with the user.

Clause 41. The system of clause 31, wherein at least some of the treatment data corresponds to at least some of the sensor data from a sensor associated with the treatment device.

Clause 42. The system of clause 31, wherein, while the user uses the treatment device, at least some of the treatment data corresponds to at least some of the sensor data from a sensor associated with a wearable device worn by the user.

Clause 43. The system of clause 31, wherein, while the user engages in the at least one activity, at least some of the alignment data corresponds to at least some sensor data from a one sensor associated with at least one wearable device worn by the user.

Clause 44. The system of clause 43, wherein the at least one wearable device includes at least one of a goniometer and a pedometer.

Clause 45. The system of clause 31, wherein, while the user engages in the at least one activity, at least some of the alignment data corresponds to at least some sensor data from at least one sensor associated with an image capturing device.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A method comprising:

receiving treatment data associated with a user capable of using a treatment device to perform a treatment plan, wherein the treatment data comprises one or more characteristics of the treatment device and at least one characteristic of the user, treatment measurement information associated with the user while the user uses the treatment device, and at least one aspect of the treatment plan;

receiving, from one or more sensors of the treatment device while the user uses the treatment device, user related data (URD) associated with the user, wherein the URD includes at least one pedal pressure measurement corresponding to a pressure applied by the user to at least one pedal of the treatment device;

receiving alignment data associated with a component of the treatment device that is configured to physically engage with at least one body part of the user while the user engages in at least one activity, wherein the alignment data comprises, with respect to the at least one body part, at least one of relative position data, relative angle data, or rotational motion data associated with the component of the treatment device;

identifying, based on at least the treatment data, the URD, and the alignment data, at least one alignment characteristic associated with the user, wherein the at least one alignment characteristic includes at least one alignment delta value that indicates a difference between at least some of the alignment data and at least one of (i) at least some of the treatment data, and (ii) at least some of the URD; and modifying at least one aspect of the treatment plan in response to receiving, from a healthcare professional, treatment plan input including at least one modification to the at least one aspect of the treatment plan, wherein the at least one modification to the at least one aspect of the treatment plan is determined, at least in part, based on the at least one alignment characteristic, and wherein the at least one modification comprises a modification to: a diet regimen, a medication regimen, a sleep regimen, a medical procedure, an amount of time to perform an exercise, an exercise parameter of the treatment device, a schedule for performing the exercise, or a frequency of occurrence corresponding to the exercise comprising (a) numbers of repetitions, (b) intervals, and (c) minimum or maximum thresholds.

2. The method of claim 1, wherein the at least one activity includes at least one of using the treatment device and an activity other than using the treatment device.

3. The method of claim 1, wherein the healthcare professional uses at least one artificial intelligence engine configured to use at least one machine learning model that generates, based on the at least one alignment characteristic, the treatment plan input.

4. The method of claim 3, wherein the artificial intelligence engine is associated with at least one of the treatment device, a remotely located server computing device, and a computing device of a healthcare professional.

5. The method of claim 1, further comprising communicating with an interface, at a computing device of the healthcare professional, wherein the interface is configured to receive the information associated with the at least one alignment characteristic.

6. The method of claim 5, wherein the healthcare professional includes a human healthcare professional at least partially responsible for treatment of the user.

7. The method of claim 1, further comprising controlling, while the user uses the treatment device, and based on the modified the at least one of the at least one aspect and any other aspect of the treatment plan, the treatment device.

8. The method of claim 7, wherein the user uses the treatment device during a telemedicine session.

9. The method of claim 1, wherein the treatment measurement information includes, while the user uses the treatment device, at least one of a vital sign of the user, a respiration rate of the user, a heartrate of the user, a temperature of the user, an SpO2 measurement of the blood oxygen level of the user, and a blood pressure of the user.

10. The method of claim 1, wherein the alignment data includes at least one of lateral motion data associated with the at least one body part or pressure data associated with the at least one body part.

11. The method of claim 1, wherein at least some of the treatment data corresponds to at least some of sensor data from a sensor associated with the treatment device.

12. The method of claim 1, wherein, while the user uses the treatment device, at least some of the treatment data corresponds to at least some of sensor data from a sensor associated with a wearable device worn by the user.

13. The method of claim 1, wherein, while the user engages in the at least one activity, at least some of the alignment data corresponds to at least some sensor data from a sensor associated with at least one wearable device worn by the user.

14. The method of claim 13, wherein the at least one wearable device includes at least one of a goniometer and a pedometer.

15. The method of claim 1, wherein, while the user engages in the at least one activity, at least some of the alignment data corresponds to at least some sensor data from at least one sensor associated with an image capturing device.

16. A tangible, non-transitory computer-readable medium storing instructions that, when executed, cause a processing device to:

receive treatment data associated with a user capable of using a treatment device to perform a treatment plan, wherein the treatment data comprises one or more characteristics of the treatment device and at least one of characteristics of the user, treatment measurement information associated with the user while the user uses the treatment device, and at least one aspect of the treatment plan;

receive, from one or more sensors of the treatment device while the user uses the treatment device, user related data (URD) associated with the user, wherein URD includes at least one pedal pressure measurement corresponding to a pressure applied by the user to at least one pedal of the treatment device;

receive alignment data associated with a component of the treatment device that is configured to physically engage with at least one body part of the user while the user engages in at least one activity, wherein the alignment data comprises, with respect to the at least one body part, at least one of relative position data, relative angle data, or rotational motion data associated with the component of the treatment device;

identify, based on at least the treatment data, the URD, and the alignment data, at least one alignment characteristic associated with the user, wherein the at least one alignment characteristic includes at least one alignment delta value that indicates a difference between at least some of the alignment data and at least one of (i) at least some of the treatment data, and (ii) at least some of the URD; and modify at least one aspect of the treatment plan in response to receiving, from a healthcare professional, treatment plan input including at least one modification to the at least one aspect of the treatment plan, wherein the at least one modification to the at least one aspect of the treatment plan is determined, at least in part, based on the at least one alignment characteristic, and wherein the at least one modification comprises a modification to: a diet regimen, a medication regimen, a sleep regimen, a medical procedure, an amount of time to perform an exercise, an exercise parameter of the treatment device, a schedule for performing the exercise, or a frequency of occurrence corresponding to the exercise comprising (a) numbers of repetitions, (b) intervals, and (c) minimum or maximum thresholds.

17. The computer-readable medium of claim 16, wherein the at least one activity includes at least one of using the treatment device and an activity other than using the treatment device.

18. The computer-readable medium of claim 16, wherein the healthcare professional uses at least one artificial intelligence engine configured to use at least one machine learning model that generates, based on the at least one alignment characteristic, the treatment plan input.

19. The computer-readable medium of claim 18, wherein the artificial intelligence engine is associated with at least one of the treatment device, a remotely located server computing device, and a computing device of a healthcare professional.

20. A system comprising:

a processor; and a memory including instructions that, when executed by the processor, cause the processor to:

receive treatment data associated with a user capable of using a treatment device to perform a treatment plan, wherein the treatment data comprises one or more characteristics of the treatment device and at least one of characteristics of the user, treatment measurement information associated with the user while the user uses the treatment device, and at least one aspect of the treatment plan;

receive, from one or more sensors of the treatment device while the user uses the treatment device, user related data (URD) associated with the user, wherein URD includes at least one pedal pressure measurement corresponding to a pressure applied by the user to at least one pedal of the treatment device;

receive alignment data associated with a component of the treatment device that is configured to physically engage with at least one body part of the user while the user engages in at least one activity, wherein the alignment data comprises, with respect to the at least one body part, at least one of relative position data, relative angle data, or rotational motion data associated with the component of the treatment device;

identify, based on at least the treatment data, the URD, and the alignment data, at least one alignment characteristic associated with the user, wherein the at least one alignment characteristic includes at least one alignment delta value that indicates a difference between at least some of the alignment data and at least one of (i) at least some of the treatment data, and (ii) at least some of the URD; and modify at least one aspect of the treatment plan in response to receiving, from a healthcare professional, treatment plan input including at least one modification to the at least one aspect of the treatment plan, wherein the at least one modification to the at least one aspect of the treatment plan is determined, at least in part, based on the at least one alignment characteristic, and wherein the at least one modification comprises a modification to: a diet regimen, a medication regimen, a sleep regimen, a medical procedure, an amount of time to perform an exercise, an exercise parameter of the treatment device, a schedule for performing the exercise, or a frequency of occurrence corresponding to the exercise comprising (a) numbers of repetitions, (b) intervals, and (c) minimum or maximum thresholds.

* * * * *